United States Patent [19]

Yamauchi et al.

[11] Patent Number: 5,723,345
[45] Date of Patent: Mar. 3, 1998

[54] METHOD AND DEVICE FOR SPECIFIC BINDING ASSAY

[75] Inventors: Tadakazu Yamauchi; Hideyuki Terasawa, both of Saitama, Japan

[73] Assignee: Mochida Pharmaceutical Co., Ltd., Tokyo, Japan

[21] Appl. No.: 495,028

[22] Filed: Jun. 27, 1995

[30] Foreign Application Priority Data

Jun. 28, 1994 [JP] Japan .................... 6-146865

[51] Int. Cl.$^6$ .............. G01N 33/543; G01N 33/558; G01N 33/536
[52] U.S. Cl. .............. 436/518; 204/400; 204/403; 422/57; 422/58; 422/82.01; 422/82.05; 422/82.08; 422/82.09; 435/7.1; 435/7.72; 435/7.9; 435/7.91; 435/7.92; 435/287.1; 435/287.2; 435/817; 436/169; 436/514; 436/531; 436/535; 436/536; 436/538; 436/805; 436/806
[58] Field of Search ............... 422/56–58, 68.1, 422/82.01, 82.05, 82.06–82.09; 435/7.1, 7.72, 7.9, 7.91, 7.92–7.94, 817, 962, 967, 969–971, 287.1, 287.2; 436/518, 531, 535–541, 169, 805, 806, 904, 514; 204/400, 403

[56] References Cited

U.S. PATENT DOCUMENTS

| 5,194,133 | 3/1993 | Clark et al. | 204/299 |
| 5,281,539 | 1/1994 | Schramm | 436/518 |
| 5,491,095 | 2/1996 | Bepko et al. | 436/518 |

FOREIGN PATENT DOCUMENTS

| 0525723 | 2/1993 | European Pat. Off. . | |
| 5-264552 | 10/1993 | Japan . | |
| WO91/16630 | 10/1991 | WIPO . | |

OTHER PUBLICATIONS

Patent Abstracts of Japan, vol. 18, No. 31, JP-A-5-264552 (Jan. 18, 1994).

*Primary Examiner*—Christopher L. Chin
*Attorney, Agent, or Firm*—Birch, Stewart, Kolasch & Birch, LLP

[57] ABSTRACT

The present invention provides a general purpose specific binding assay method which has the advantages of highly accurate and quick measurements which exclude the effects of various factors that decrease reliability of the measured values, such as non-specific reactants in test samples, assay conditions and inactivation and the like changes in the activity of reagents. The present invention is further drawn to a specific binding assay device suitable for the practice thereof. The binding assay of the present invention is achieved by allowing a signal substance generator which takes part in a specific binding reaction and generates a signal substance, together with a liquid sample, to flow through a predetermined channel in a predetermined direction, thereby effecting generation of the specific binding reaction of a substance to be assayed to form a distribution of the signal substance generator in the channel in response to the concentration of the substance to be assayed, allowing the signal substance generator distributed in the channel to generate the signal substance, detecting the generated signal substance by a plurality of detection means arranged at different positions in the liquid flow direction, and arithmetically processing the plural detection results to minimize influence of other factors than the concentration of the substance to be assayed upon the assay result.

9 Claims, 29 Drawing Sheets

FIG. 29 additive influences examples of measurement error factors:
sample-derived oxidation reduction substances
sample-derived peroxidase activities proportional influences examples of measurement error factors:
inactivation of labeling enzymes in time
reaction temperature
sample-derived substances which inhibit
a signal substance or generator thereof

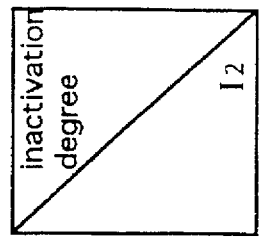

in this case,
inactivation
degree ratio is
estimated 50%

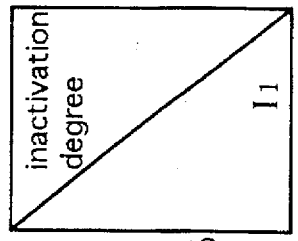

specific-reaction
-derived components
of signal (signal)

non-specific components
of signal (noise)

METHOD AND DEVICE FOR SPECIFIC BINDING ASSAY

FIELD OF THE INVENTION

This invention relates to a specific binding assay method by which substances to be assayed in test samples can be measured simply, quickly and accurately without undergoing influences of non-specific reactions and contaminants, making use of a specific binding reaction of a substance to be assayed with another substance (specific binding substance) which binds specifically to the substance to be assayed, and to a specific binding assay device suitable for the practice of the method.

More particularly, this invention relates to a specific binding assay method, as well as a device suitable for the practice of the method, in which (1) a specific binding reaction-related substance which binds to a specific binding substance in competition with a substance to be assayed or binds specifically to the substance to be assayed and can generate a signal substance directly or indirectly is used as a label (signal substance generator), (2) a distance distribution of the signal substance generator correlative to a detection means is formed in response to the concentration of the substance to be assayed, in a channel where the specific binding substance is immobilized, making use of at least one specific binding reaction of the substance to be assayed with the specific binding substance, (3) the signal substance generated by the signal substance generator is detected at the detection means and then (4) the substance to be assayed is measured making use of a property in which the signal strength observed at the detection means is modulated in response to the distance between the signal substance generator and the detection means (that is, diffusion length of the signal substance), wherein a plurality of the detection means are arranged at different positions in the flow direction in order to realize accurate assay by excluding influences of contaminants, temperature and the like.

BACKGROUND OF THE INVENTION

There are a number of known specific binding assay methods such as an immunoassay in which an antigen-antibody reaction is employed, a receptor assay in which a receptor is used and a nucleic acid probe assay in which hybridization of complementary nucleic acid sequences is employed. Because of the high specificity, these assay methods are used frequently in various fields including clinical inspection and the like.

In general, these methods are divided into a heterogeneous method which requires a step, so-called B/F (bound/free) separation, for the isolation of unreacted substances after specific binding reactions and a homogeneous method that does not require the B/F separation step.

The heterogeneous method is useful for the measurement of samples with relatively high sensitivity and can be regarded as a general purpose method, because it can detect degree of the specific binding reaction without receiving interference of unreacted substances and samples by carrying out the B/F separation. This method, however, requires complex handling for the separation of unreacted substances and, in some cases, requires special tools or instruments such as a washing apparatus. Because of this, it is still necessary to improve this method in terms of its simplicity and quickness.

On the other hand, various types of homogeneous type assay methods, including an agglutination method, an EMIT method, a proximal linkage immunoassay such as an enzyme channeling technique, an immunochromatography and the like, have been developed with the aim of improving handling simplicity. These techniques, however, are still inferior to the heterogeneous method in terms of performance and general purpose use.

Particularly, in comparison with the heterogeneous method in which a detection reaction is carried out after B/F separation, the homogeneous method in which its detection reaction is carried out in the presence of a sample has another disadvantage in that it is apt to cause errors due to sample interference and measuring conditions.

In order to minimize such errors, measured values are generally corrected using authentic samples in the specific binding assays. That is, the amount of a substance to be assayed in an unknown sample is determined by a method in which the unknown sample is analyzed together with an authentic sample whose content of the substance to be assayed is already known, and the thus obtained signal strength of the unknown sample is compared with that of the authentic sample.

In a generally and frequently used method, a relational curve between the signal strength and the concentration of a substance to be assayed (standard curve) is prepared from an authentic sample which is serially diluted into known concentrations over the measurable range of each assay method, and the signal strength of each unknown sample is converted to the concentration of the substance to be assayed based on the standard curve. In consequence, such an assay method requires simultaneous analysis of a number of authentic samples even when only one unknown sample is to be assayed, so that the assay handling becomes complex which is economically wasteful.

With the recently enriching domestic and regional medical care and increasing demands for emergency clinical inspections, great concern has been directed toward the development of a specific binding assay method by which a substance to be assayed can be measured quickly, easily and accurately by persons who have no knowledge about clinical inspection.

In general, domestic and emergency inspections of samples to be tested must be carried out quickly but one at a time. In consequence, the simultaneous authentic sample analysis which requires additional assay steps, time and reagents is not applicable to such a field of inspections that, on the contrary, must be carried out with a particularly high measuring reliability.

With the aim of overcoming such problems, the inventors of the present invention have conducted intensive studies and succeeded in developing a specific binding assay method, so-called MEDIA (mediator diffusion-controlled immunoassay), in which a distance distribution of a signal substance generator correlative to a detection means is formed in response to the concentration of a substance to be assayed in a liquid sample, making use of a specific binding reaction of the substance to be assayed in the liquid sample, and the distribution is detected at the detection means as a mass transfer of a signal substance generated by the signal substance generator, namely as a signal strength which is rate-determined by the diffusion length [cf. JP-A-5-264552 (the term "JP-A" as used herein means an "unexamined published Japanese patent application") and European Patent 0,525,723 A2]. According to this method, substances to be assayed in test samples can be measured easily and quickly with a high sensitivity without requiring a step for the removal of unreacted substances.

However, similar to the case of the other homogeneous assay methods, even this assay method sometimes causes measuring errors of the substance to be assayed in a test sample, because interference of the sample, measuring conditions such as reaction temperature and the like or changes in the reagents used in the assay system exert an influence upon the signal strength to be detected at the detection means in some cases.

SUMMARY OF THE INVENTION

A primary object of the present invention, which has been accomplished with the aim of overcoming the aforementioned problems involved in the prior art, is to provide a simple and general purpose specific binding assay method which is based on a principle of the specific binding assay but does not require a step for the separation of unreacted substances (washing step) and can perform highly accurate and quick measurement effected by the exclusion of various factors that decrease reliability of the measured values, such factors including non-specific influence of test samples upon the measurement, assay conditions such as reaction temperature and the like and changes in the activity of reagents used in the assay caused for example by their inactivation. It also provides a specific binding assay device suitable for the practice of the specific binding assay method.

According to a first aspect of the present invention, there is provided a method for specific binding assay in which a substance to be assayed in a liquid sample is measured based on its specific binding reaction, which comprises allowing a liquid sample and a specific binding reaction-related signal substance generator that generates a signal substance to flow through a predetermined channel in a predetermined direction, generating a specific binding reaction of the substance to be assayed, forming a distribution of the signal substance generator in the channel in response to the concentration of the substance to be assayed in the liquid sample making use of the specific binding reaction, allowing the signal substance generator distributed in the channel to generate the signal substance, detecting the generated signal substance by a plurality of detection means arranged at different positions in the flow direction, and then arithmetically processing the plural detection results to minimize influence of other factors than the concentration of the substance to be assayed upon the assay result.

According to a second aspect of the present invention, there is provided a specific binding assay device useful for the practice of the assay method of the first aspect of the present invention, which comprises (1) a liquid sample-introducing means, (2) a liquid sample-flowing channel connected thereto and (3) a plurality of detection means arranged at different positions in the liquid flow direction by which a distribution of a signal substance generator, formed in the channel in response to the concentration of a substance to be assayed in a liquid sample by a specific binding reaction of the substance to be assayed with a specific binding substance capable of binding specifically thereto, is detected as a signal strength which is rate-limited by diffusion mass transfer to detection means of a signal substance generated from the signal substance generator.

The detection means are preferably electro-chemical detective systems, preferably, the plural detection means in the inventive specific binding assay device are electrochemical electrodes.

Also preferably, the plural detection means in the inventive specific binding assay device are arranged at a distance of 10 μm or more in the flow direction.

Other objects and advantages of the present invention will be made apparent as the description progresses.

BRIEF DESCRIPTION OF THE DRAWINGS

FIG. 29 is a schematic view showing the influences which measuring error factors affect to the signal intensities $I_1$, $I_2$ measured at two detection means.

Figure 1:
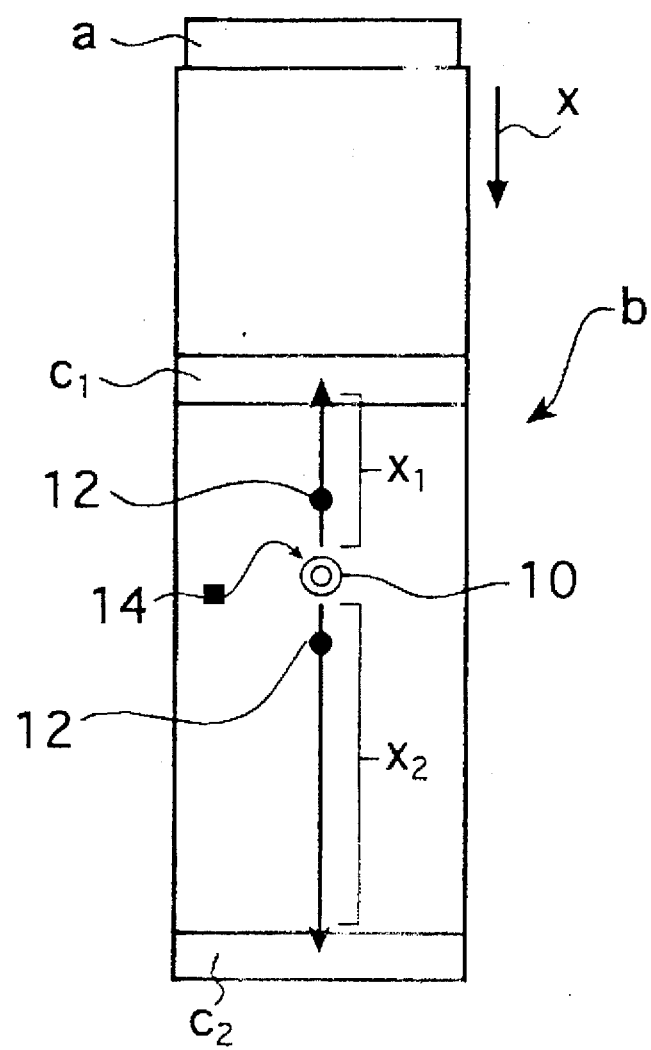
FIG. 1 is a conceptual graph showing a principle of the specific binding assay method of the present invention.

In these figures, each character means as follows: 1, liquid sample; 2, antigen; 3, enzyme; 4, enzyme labeled antibody; 5, immobilized antigen; 6, detection means 1; 7, detection means 2; 10, signal substance generator; 12, signal substance; 14, substance related to the generation of signal substance; 50, upper cover; 50a, sample-introducing means; 52, filter; 54, first impregnation portion; 56, second impregnation portion; 56a and 64a, sealing means; 58, communication means; 60, electrode portion; 61, electrode base plate; 62, channel (matrix); 64, absorption means; 66, base cover; 68, through hole; 70, counter/reference electrode; 70a, counter/reference electrode; 74, insulating layer; 76, first working electrode (detection means 1); 76a, first working electrode terminal; 78, second working electrode (detection means 2); 78a, second working electrode terminal; 80, third working electrode (detection means 3); 80a, third working electrode terminal; a, sample-introducing means; b, channel; and c, detection means.

DETAILED DESCRIPTION OF THE INVENTION

Firstly, technical terms used in the specification of this invention are explained.

The term "substance to be assayed" as used herein means a substance which is measured by the method or the device of the present invention.

Examples of such substances include those which are antibodies or functionally capable of acting as antigen molecules, such as proteins, polypeptides, glycoproteins, polysaccharides, complex glycolipids and the like; or nucleic acids, effector molecules, receptor molecules, enzymes, inhibitors and the like.

More illustratively, such substances include: tumor markers such as α-fetoprotein, carcinoembryonic antigen (CEA), CA 125, CA 19-9 and the like; various proteins such as $\beta_2$ microglobulin ($\beta_2$ m), ferritin and the like; various hormones such as estradiol ($E_2$), estriol ($E_3$), human chorionic gonadotropin (hCG), luteinizing hormone (LH), human placental lactogen (hPL) and the like; various virus-related antigens or antibody molecules such as HBs antigen, anti-HBs antibody, HBe antigen, anti-HBe antibody, anti-HBc antibody, anti-HCV antibody, anti-HIV antibody and the like; various allergens and their corresponding IgE antibody molecules; narcotic drugs, medical drugs and metabolic products thereof; and nucleic acids having virus- and disease-related polynucleotide sequences.

The term "analogue of a substance to be assayed" as used herein means a substance which shows similar behavior to the substance to be assayed in a binding reaction with a specific binding substance which will be described later.

For example, it means a substance structurally analogous to the substances to be assayed, which includes various types of structural analogues of the substances to be assayed. In the present invention, it is used as a composing element of a signal substance generator which will be described later, mainly when a specific binding reaction is effected by a competitive method. When the substance to be assayed is a low molecular weight steroid hormone, drug compound or the like, its structural analogue is the same substance to be assayed or a modified compound thereof. When the substance to be assayed is a protein, a nucleic acid or a polysaccharide, its structural analogue means a partial peptide, a partial oligonucleotide, a partial oligosaccharide or the like.

Also, when the substance to be assayed is an antibody or the like, illustrative examples of its analogues include those which can bind to a specific antigen as a specific binding substance in competition with the substance to be assayed, namely various functional analogues of antibodies, receptors, lectins and the like substances to be assayed.

The term "liquid sample" as used herein means a liquid material which contains or probably contains a substance to be assayed. Illustrative examples of the liquid sample include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extracts, solutions and the like.

The term "specific binding substance" as used herein means a substance which has a specific affinity for a certain substance such as a substance to be assayed, that is, a substance which is capable of undergoing a specific binding reaction with a specific substance.

Examples of combinations of the specific substance with its corresponding specific binding substance include: antigens with corresponding antibody molecules, a nucleic acid sequence with its complementary sequence, effector molecules with receptor molecules, enzymes with inhibitors, enzymes with cofactors, enzymes with substrates, sugar chain-containing compounds with lectins, an antibody molecule with another antibody molecule specific for the former antibody, receptor molecules with corresponding antibody molecules and the like combinations.

In the above descriptions, the combination of, for example, antigen-antibody shows the both types of combinations, namely, specific substance—specific binding substance and specific binding substance—specific substance (reverse type).

Other examples of the specific binding substances include a specific binding substance which has been chemically modified to such a degree that its specific binding activity still remains intact and a complex body of a specific binding substance bound to other component. Examples of such types of specific binding substances include a chemically biotin-modified antibody molecule or polynucleotide, an avidin-covalent antibody molecule and the like. Also included are antibody-enzyme, antibody-receptor and the like fusion proteins prepared by recombinant DNA techniques.

In the specification of the present invention, a substance which has a portion that acts as a specific binding substance may also be used as a specific binding substance, such as the following signal substance generator.

The term "signal substance generator" as used herein means a substance which takes part in the specific binding reaction, such as a substance which binds to a specific binding substance in competition with a substance to be assayed or a substance that specifically binds to the substance to be assayed, and can generate a signal substance directly or indirectly.

As will be described later, the signal substance generator forms its distribution in a channel, depending on the amount of the substance to be assayed. In other words, the signal substance generator is a labeled specific binding substance consisting of a portion which acts as a specific binding substance and another portion that contributes to the formation of a signal substance which will be described later.

In this instance, the portion which acts as a specific binding substance has a structure as a specific binding substance for a substance to be assayed, or has a structure of the substance to be assayed or its analogue, and the other portion that contributes to the formation of a signal substance is composed of various types of enzymes or the like which are conventionally used as labeling agents in immunological reactions and the like.

That is, the signal substance generator is a substance which, on the one hand, takes part in the specific binding reaction of a substance to be assayed with a corresponding specific binding substance, thereby changing its distribution in a channel in response to the amount of the substance to be assayed, and, on the other hand, contributes to the formation of a signal substance.

The term "signal substance" as used herein means a substance which is formed by the signal substance generator-contributing reaction and which generates a certain signal by itself or causes other substance to generate a signal at the detecting means described below.

The term "substance related to the generation of a signal substance" as used herein may include the aforementioned signal substance generator when the term is interpreted literally. According to the present invention, however, it means a substance other than the signal substance generator, such as a precursor of a signal substance or a substance which contributes to the conversion of the precursor into its corresponding signal substance. Examples of such a type of substance include an electron mediator or a substance which generates the electron mediator, an enzyme substrate, an enzyme cofactor, a hydrogen donor and the like which will be described later.

The term "substance related to the generation of a signal" means a substance which contributes to the generation of a signal, excluding the signal substance, when the signal substance does not generate a signal directly but causes other substance to generate a signal, or when the signal substance generates a signal in conjunction with other substance.

Examples of signals include electron transfer which is measurable by electrochemical means, fluorescence which is measurable using a fluorophotometer, luminescence which is measurable using an luminometer and coloring which is measurable by visual judgment or using a reflect-meter. The electrochemical means is most preferable, because it can measure signals even in total blood and the like samples which contain blood cell components, hemoglobin and the like.

The specific binding substance, the signal substance generator, the substance related to the generation of a signal substance and the substance related to the generation of a signal may be included in the assay device in advance or introduced into the assay device prior to, at the same time of or after the introduction of a liquid sample.

When these substances are included in the assay device in advance, they may be distributed evenly in the assay device or arranged on specified positions in the assay device so that they are dissolved when a liquid sample or a developing solution other than the sample is introduced.

The term "channel" as used herein means a passage of the flow of a liquid sample introduced through a sample-introducing means, where a substance to be assayed and a signal substance generator are developed to generate the specific binding reaction.

The liquid sample introduced through the sample-introducing means is introduced into the channel by an external pressure such as of a pump, an external force such as gravity, or, a spontaneous permeation.

In order to enable reproducible introduction of the liquid sample into the channel using a simple device, it is desirable to introduce the liquid sample by its own spontaneous permeation by constructing the channel with a capillary or a narrow gap or with a porous member.

For example, it is an area in which a specific binding substance is immobilized on the channel-constituting capillary or a porous member and where a specific binding reaction occurs to form a distribution along the flow direction of a liquid sample when the liquid sample and a signal substance generator flow in a predetermined direction. In an illustrative example of such an area, a substance to be assayed and a signal substance generator perform specific binding to a specific binding substance in a competitive manner, or the substance to be assayed binds to the specific binding substance and then the signal substance generator specifically binds to the substance to be assayed in a sandwich or the like manner, so that the specific binding reaction occurs having a distribution along the flow direction of the liquid sample and a distribution of the signal substance generator is formed in response to the concentration of the substance to be assayed in the liquid sample.

The channel where the specific binding reaction and the like occur having a distribution along the flow direction of a liquid sample is not limited to the case in which a specific binding substance is immobilized, but may be an area where changes in the molecular weight, particle size and the like caused by the specific binding reaction are used as a distribution.

The term "detection means" as used herein means an area where a signal generated by the signal substance is detected and a degree of signal modulation is measured by visual judgment or using an appropriate external measuring instrument depending on the signal properties.

According to the present invention, a plurality of the detection means are arranged at different positions along the liquid sample flowing direction in the channel, in order to enable accurate assay by minimizing influences of other factors than the concentration of the substance to be assayed, such as contaminants, viscosity and the like sample properties, reaction (development) temperature and the like environmental conditions and enzyme activity reduction, substrate decomposition and the like changes in the reagents used in the assay system.

The term "absorption means" as used herein means a part which comprises a water-absorbable material and where, when required, the aforementioned substance related to the generation of a signal substance and the like are maintained. This means also contributes to the absorption and keeping of the introduced liquid test sample.

The following describes the present invention in detail making use of the thus defined terms.

In this connection, basic concepts of the method and device of the specific binding assay of the present invention are disclosed in detail in JP-A-5-264552 and European Patent 0,525,723 A2 which are referenced herein and incorporated in the present specification. All modes disclosed in these patents, therefore, can be applied to the present invention.

As conceptually shown in FIG. 1, the specific binding assay of the present invention is carried out using a device which comprises a sample-introducing means "a" from which a liquid sample is introduced, a liquid sample-flowing channel "b" connected thereto and a plurality (2 in the drawing) of detection means arranged at different positions in the liquid sample flow direction (direction of an arrow "x" in FIG. 1), namely a first detection means $c_1$ and a second detection means $c_2$ (both means will altogether be referred to as "c" hereinafter).

In the example shown in FIG. 1, a liquid sample containing unknown amount of a substance to be assayed is introduced from the sample-introducing means "a" into the device, a distribution of a signal substance generator 10 is formed in a channel "b" in response to the amount of the substance to be assayed in the liquid sample making use of at least one specific binding reaction of the substance to be assayed with a specific binding substance, followed, if necessary, by additional reaction with a substance 14 which is related to the generation of a signal substance, thereby effecting generation of the signal substance 12 by the signal substance generator 10 which is distributed in the channel "b", and then a signal generated by the signal substance 12 is measured at a detection means "c" when the signal substance reaches the detection means after its diffusion through the channel.

Though a single signal substance generator 10 is shown in FIG. 1, the signal to be measured at the detection means "c" is rate-determined by the diffusion mass transfer of the signal substance 12 continuously generated from a number of the signal substance generator 10 distributed in the channel "b". In other words, the signal is dependent on a distance $x_1$ or $x_2$ between the signal substance generator 10 as the source of the signal substance 12 and the detection means $c_1$ or $c_2$, a distance in which the signal substance 12 must be transferred by diffusion in the channel.

As will be described later, distribution of the signal substance generator 10 is dependent on the amount of the substance to be assayed in the liquid sample. In consequence, when the amount of the substance to be assayed in the liquid sample introduced from the sample-introducing means "a" into the channel "b" is varied, diffusion distance distribution of the signal substance 12 between the signal substance generator 10 and the detection means "c" varies depending on the amount of the substance to be assayed. As the result, a difference in the distribution of the signal substance generator 10 can be detected as a difference in the signal generated by the signal substance 12 which reached the detection means "c".

Accordingly, the specific binding assay method and the specific binding assay device of the present invention, effected by the application of such a design, are characterized in that the amount of a substance to be assayed in a liquid sample is measured based on the signals which are generated by the signal substance 12 and detected at a plurality of the detection means "c".

As described in the foregoing, the term "specific binding reaction" means a reaction of a substance to be assayed with a specific binding substance (including the signal substance generator 10) which has a specific affinity for the substance to be assayed or a reaction of the specific binding substance with the signal substance generator 10.

Accordingly, the present invention has rendered possible highly accurate and quick assay by minimizing influences on the assay results caused by various factors other than the concentration of the substance to be measured, such factors including assay conditions such as reaction (development) temperature and the like, contaminants in liquid samples and changes in the activity of reagents used in the assay caused for example by their inactivation, which has been effected on the basis of the basic concepts that:

(1) signals observed at the detection means "c" can be modulated in response to the distance between a label (signal substance generator 10) and the detection means "c" (that is, diffusion length of the signal substance 12), in the case of the use of the signal substance 12 which is generated by the label of the signal substance generator 10 and directly or indirectly generates signals that are detectable only at the detection means "c";

(2) positional distributions in the channel of the signal substance generators 10 (labels) can be changed in response to the concentration of a substance to be assayed in a liquid sample, through at least one specific binding reaction of the substance to be assayed with a specific binding substance; and (3) the signals detected at the detection means "c" therefore correspond to the concentration of the substance to be assayed in the liquid sample, and further supported by an improvement in that: the above signals are detected by a plurality of the detection means "c" arranged at different positions in the liquid sample flowing direction, such as the first detection means $c_1$ and the second detection means $c_2$ as shown in FIG. 1.

The present inventors have found the above basic concepts and proposed specific binding assay method and device making use thereof (cf. JP-A-5-264552 and European Patent 0,525,723 A2). This assay method is called MEDIA (mediator diffusion-controlled immunoassay). According to this assay method (device), substances to be assayed in test samples can be measured quickly with a high sensitivity without requiring a step for the removal of unreacted substances.

Even this method, however, sometimes causes errors when the amount of substances to be assayed in unknown samples are measured, because influences of contaminant interference, measuring conditions such as reaction temperature and the like and changes in the activity of reagents used in the assay system cannot be eliminated completely.

In order to resolve such problems, the present inventors have conducted intensive studies and found, as will be described later in detail, that there is a certain relationship between plural signals detected by a plurality of detection means arranged at different positions in the flow direction of a liquid sample and also between these plural signals and the amount of a substance to be assayed in an unknown sample (namely distribution of a signal substance generator) in the aforementioned specific binding reaction-applied assay method, so-called MEDIA (mediator diffusion-controlled immunoassay).

Thereafter, the present inventors have examined this relationship by experiments and experiences and found arithmetic expressions which can minimize influences of various factors other than the concentration of substances to be assayed (amount of substances in test samples) upon the signals, for example, contaminants, environmental conditions such as reaction (development) temperature and inactivation of reagents used in the assay caused such as decrease in the enzyme activity. The present invention has been accomplished based on a finding that more accurate specific binding assay can be made when results of the measurement of signals are arithmetically processed using this arithmetic expression.

The present invention has been accomplished on the basis of the following technical ideas.

That is, as will be described later in detail in EXAMPLES, according to the assay method (device) of the present invention, the signals measured at a plurality of the detection means arranged at different positions in the flow direction are derived from the same signal substance generator, but become different functions against the concentration of a substance to be assayed in a liquid sample. The reason for this is that the distance distribution between the signal substance generator and each detection means varies depending on each detection means, because positions of the detection means differ from one another in the flow direction of the liquid sample, namely in the direction of the formation of the signal substance generator distribution. This means that the specific signal strength component which is dependent on the amount of the substance to be assayed substantially varies at each detection means.

The signal measured at each detection means is originated from completely the same signal generation mechanism in which the generated signal is measured when a specified signal substance reaches the detection means by means of diffusion, so that the signal also undergoes influences of contaminants in the liquid sample, environmental conditions such as reaction (development) temperature and inactivation of reagents used in the assay caused such as decrease in the enzyme activity in the same manner.

Figure 27:
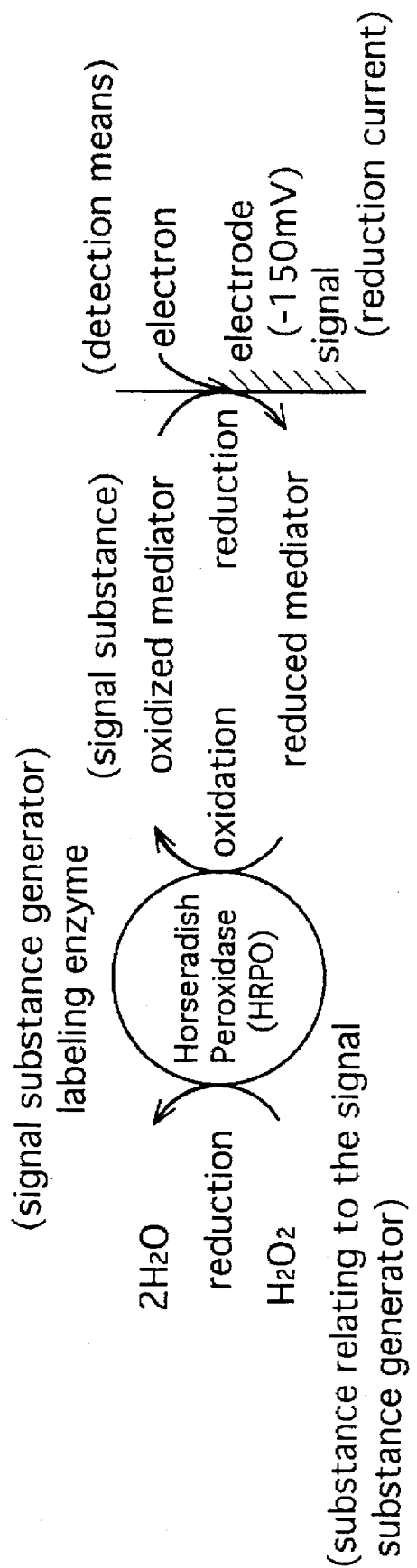
FIG. 27 is a schematic view showing a system of detecting signals of this invention.

The signal measured at each detection means is a mixture consisting of the specific signal strength component which is dependent on the amount of the substance to be assayed and non-specific signal strength components. The non-specific signal strength components are mixtures of the additive components which influence additively to the specific signal strength and proportional components which influence proportionally to the specific signal strength, as shown in FIG. 27. The present inventors have examined relationships between signals measured at plural detection means, which seemingly have different tendencies in the response to the amount of the substance to be assayed in the liquid sample, and between these signals and the amount of the substance to be assayed, and found arithmetic expressions (relational expressions) which can reduce influences of various factors other than the concentration of substances to be assayed from the data measured at a plurality of detection means arranged at different positions in the flow direction of the liquid sample. The accurate specific binding assay method which can minimize influences of samples, assay environment, periodical changes in the assay device and the like was realized by calculating the amount of the substance to be assayed from a plurality of detection results using this relational expression.

Accordingly, the specific binding assay method (device) of the present invention provides a novel, so-called standardless assay technique by which the amount of a substance to be assayed can be calculated by merely measuring an unknown sample. Such a technical idea is completely different from the prior art signal correction method in which a specific binding reaction with a standard substance or a standard signal generation reaction is carried out separately or simultaneously in the same device, and the signal of an unknown substance to be assayed is judged using the standard signal.

Positional gaps among a plurality of detection means in the flow direction are not particularly limited, but, according to an examination conducted by the present inventors, it is preferable to arrange plural detection means with a geometric distance of 10 μm or more, more preferably 100 μm or more, in the liquid flow direction of the channel "b" in the case of the present invention in which a specific binding reaction is employed. Such an arrangement renders possible the detection of significantly different signals at a plurality of the detection means, which are rate-determined by the mass transfer (diffusion) of the signal substance 12 in response to the formed distribution of the signal substance generator 10 by the specific binding reaction, and the realization of accurate assay by preparing an arithmetic expression which can minimize influences of other factors than the concentration of the substance to be assayed upon the assay results.

When two detection means are positioned with a distance of 10 μm or more, the influences to the non-specific signal strength including additive factors and proportional factors can be detected and deleted by using proper relation formulae derived from the detected data.

According to the specific binding assay of the present invention, distribution of the signal substance generator 10 in the channel "b" is changed by the specific binding reaction in response to the amount of a substance to be assayed in a liquid sample, and the distribution changes are measured at a plurality of the detection means arranged at different positions in the flow direction of the liquid sample.

There are many methods to change distribution of the signal substance generator 10 in the channel in response to the amount of a substance to be assayed in a liquid sample, and the method described below is merely an example thereof.

As an illustrative example of the specific binding reaction of the method of the present invention in which a binding substance specific for a substance to be assayed is used, the following describes some immunological reactions (specific binding reactions) in the channel "b" in the case of a substance to be assayed which is a component of an immunological reaction system.

A first example is a competitive method which is carried out by immobilizing the same substance to be assayed or an analogous substance thereof.

In this case, the same substance to be assayed or an analogous substance thereof is immobilized on the channel "b", and a combined body of an anti-substance to be assayed antibody as a specific binding substance and a label (for example, an enzyme which takes part in the generation reaction of the signal substance 12) is used as the signal substance generator 10.

A substance to be assayed in a liquid sample and the same but immobilized substance to be assayed (or an analogue thereof) are allowed to react with the antibody moiety (specific binding substance) of the signal substance generator 10 in a competitive manner, by mixing the liquid sample with the signal substance generator 10 in advance and introducing the mixture into the channel "b" or by mixing the liquid sample with the signal substance generator 10 at an impregnation portion containing the signal substance generator 10, located on an upstream area of the channel "b", and allowing the mixture to flow into the channel "b". As the results, distribution of the signal substance generator 10 shifts to more downstream side in the channel "b" when the amount of the substance to be assayed is large.

This method can be used suitably for either of low molecular weight substances to be assayed such as haptens and high molecular weight substances to be assayed. When the substance to be assayed is a hapten, the same hapten as the substance to be assayed or other hapten with which a specific binding substance can undergo a cross reaction may be immobilized on the channel "b" in such a manner that the specific binding substance can be bonded thereto. When the substance to be assayed is a high molecular weight substance such as a protein, the protein itself or a peptide sequence of an epitope to which the specific binding substance can be bonded may be immobilized on the channel "b".

A second example is a sandwich method which is useful when the substance to be assayed is a high molecular weight compound that can bind simultaneously to a plurality of antibody molecules.

In this case, an antibody specific for an epitope A as a first specific binding substance of a substance to be assayed is immobilized on the channel "b" and a combined body of a label with an antibody specific for an epitope B which is a second specific binding substance of the substance to be assayed is used as the signal substance generator 10, and the reaction with the substance to be assayed is effected by mixing the liquid sample with the signal substance generator 10 in advance and introducing the mixture into the channel "b" or by mixing the liquid sample with the signal substance generator 10 at an impregnation portion containing the signal substance generator 10, located on an upstream area of the channel "b", and allowing the mixture to flow into the channel "b". That is, the substance to be assayed in the liquid sample is allowed to react in a sandwich type fashion. As the results, distribution of the signal substance generator 10 shifts to more upstream side in the channel "b" when the amount of the substance to be assayed is large.

When the substance to be assayed is an antibody, an antigen to be used as a specific binding substance is immobilized on the channel "b", and a combined body of an anti-(antibody) antibody with a label is used as the signal substance generator 10 and allowed to react with the substance to be assayed.

A third example is a competitive method which is carried out by immobilizing a binding substance specific for a substance to be assayed.

In this case, an anti-substance to be assayed antibody to be used as a specific binding substance is immobilized on the channel "b" and a combined body of a label with the same substance to be assayed or an analogue thereof, which competes with the substance to be assayed for the immobilized specific binding substance, is used as the signal substance generator 10, and the substance to be assayed in a liquid sample and the signal substance generator 10 are allowed to react with the immobilized specific binding substance in a competitive manner, by mixing the liquid sample with the signal substance generator 10 in advance and introducing the mixture into the channel "b" or by mixing the liquid sample with the signal substance generator 10 at an impregnation portion containing the signal substance generator 10, located on an upstream area of the channel "b", and allowing the mixture to flow into the channel "b". As the results, distribution of the signal substance generator 10 shifts to more downstream side in the channel "b" when the amount of the substance to be assayed is large.

When the substance to be assayed is an antibody, an antigen or an epitope moiety to be used as a specific binding substance is immobilized on the channel "b", and a combined body of a label with another antibody which competes with the antibody to be assayed for the immobilized specific binding substance is used as the signal substance generator 10.

In the above description, antibody or antigen molecules were immobilized on the channel "b", and the signal substance generator 10 or a substance to be assayed was allowed to bind to the antibody directly or indirectly. However, it is possible to change distribution of the signal substance generator 10 in the channel "b" in response to the amount of the substance to be assayed without allowing the signal substance generator 10 or the substance to be assayed to bind on the channel "b", that is, without immobilizing the antibody or antigen on the channel "b". Such a case is also included in the scope of the assay method of the present invention.

For example, when the substance to be assayed is a microorganism (a pathogenic fungus or the like for example) and the signal substance generator 10 is a labeled specific binding substance obtained by binding a labeling agent to an anti-microorganism antibody (anti-pathogenic fungus antibody or the like), travel speed or reaching point of a combined body of the substance to be assayed and the signal substance generator 10 in the channel "b" is considerably different from that of the free-state signal substance generator 10, because the size of the substance to be assayed (microorganism) is fairly large in comparison with the signal substance generator 10.

Such a difference in the reaching point becomes more clear when a porous material is used as the channel "b" and its mesh (pore) size is correctly selected or when a gel or sol carrier is used and its viscosity is selected correctly in response to the size of the microorganism.

In consequence, the substance to be assayed is not bound to the channel "b" but its distribution in the channel "b" is localized, and the signal substance generator 10 which is capable of undergoing a specific binding reaction with the substance to be assayed is distributed in the channel "b" in response to the amount of the substance to be assayed.

As another example, the measurement may be effected making use of the formation (so-called gel immunoprecipitation reaction) of a spontaneous precipitation complex (immunoprecipitate) of a free labeled antibody and a free substance to be assayed.

In such a case, the amount of the formed immunoprecipitate changes in response to the amount of the substance to be assayed and the formed immunoprecipitate is trapped in an upper area of the channel "b" which comprises a porous material and/or a gel carrier, but the free-state labeled antibody which did not take part in the immunoprecipitation reaction can travel downward in the channel "b". As the results, distribution of the signal substance generator 10 changes in response to the amount of the substance to be assayed in a test sample.

In the same manner, changes in the size of aggregated fine particles resulting from a specific binding aggregation reaction of a specific binding substance-immobilized fine particle carrier with a substance to be assayed can be used as changes in the distribution of the signal substance generator 10.

Next, generation of signals in the assay method of the present invention is described in detail.

The following describes a typical example in which an enzyme-labeled specific binding substance is used as the signal substance generator, based on FIG. 1 and Table 1.

TABLE 1

Reaction types of signal generation

Type 1 (signal, electron; detection means, electrode)

Signal-related substance *1 $\xrightarrow{\text{Signal substance generator}}$ Signal substance $\xrightarrow{\text{Electrode}}$ Product + Signal p-Aminophenyl α-D-galactoside (substrate) $\xrightarrow[\text{α-Galactoside-labeled specific binding substance}]{\text{Hydrolysis}}$ p-Aminophenol $\xrightarrow[\text{Electrode}]{\text{Oxidation-reduction}}$ p-Benzoquinone + 2H$^+$ + 2e$^-$ monoimine *2

Type 2 (signal, electron; detection means, electrode)

Signal-related substance *1 $\xrightarrow{\text{Signal substance generator}}$ Product + Signal substance $\xrightarrow{\text{Electrode}}$ Product + Signal Glucose (substrate) + Ferricinium ion (Fe$^{III}$) (electron mediator) $\xrightarrow[\text{Glucose oxidase-labeled specific binding substance}]{\text{Oxidation-reduction}}$ Glucono-lactone + Ferrocene (Fe$^{II}$) Ferrocene (Fe$^{II}$) $\xrightarrow[\text{Electrode}]{\text{Oxidation-reduction}}$ Ferricinium + e$^-$ ion (Fe$^{III}$)

Type 3 (signal, electron; detection means, electrode)

Signal-related substance *1 $\xrightarrow{\text{Signal substance generator}}$ Product + Signal substance $\xrightarrow{\text{Electrode}}$ Product + Signal H$_2$O$_2$ (substrate) + 2 Reduction type electron mediator (hydrogen donor) $\xrightarrow[\text{Peroxidase-labeled specific binding substance}]{\text{Oxidation-reduction}}$ 2H$_2$O + 2 Oxidation type electron mediator $\xrightarrow[\text{Electrode}]{\text{Oxidation-reduction}}$ 2 Reduction − 2e$^-$ type electron mediator

Type 4 (signal, electron; detection means, enzyme electrode)

Signal-related substance *1 $\xrightarrow{\text{Signal substance generator}}$ Product + Signal substance Signal substance $\xrightarrow{\text{Enzyme electrode}}$ Product + Signal Glucose + O$_2$ (substrates) $\xrightarrow[\text{Glucose oxidase-labeled specific binding substance}]{\text{Oxidation-reduction}}$ Gluconolactone + H$_2$O$_2$ H$_2$O$_2$ $\xrightarrow[\text{Peroxidase electrode (and electron mediator)}]{\text{Oxidation reduction}}$ 2H$_2$O − 2e$^-$

Type 5 (signal, fluorescence or emission; detection means, immobilized enzyme or substrate)

Signal-related substance *1 $\xrightarrow{\text{Signal substance generator}}$ Product + Signal substance + Signal-related Signal substance substance *1 $\xrightarrow{\text{Enzyme}}$ Product + Signal Glucose + O$_2$ (substrates) $\xrightarrow[\text{Glucose oxidase-labeled specific binding substance}]{\text{Oxidation-reduction}}$ Gluconolactone + H$_2$O$_2$ H$_2$O$_2$ (substrate) + Luminol $\xrightarrow[\text{Peroxidase}]{\text{Oxidation-reduction}}$ 2-Amino- + hν phthalate

Type 6 (signal, color; detection means, immobilized enzyme or substrate)

Signal-related substance *1 $\xrightarrow{\text{Signal substance generator}}$ Product + Signal substance + Signal-related Signal substance substance *1 $\xrightarrow{\text{Enzyme}}$ Signal Urate + O$_2$ (substrates) $\xrightarrow[\text{specific binding substance}]{\text{Uricase-labeled}}$ Allantoin + H$_2$O$_2$ H$_2$O$_2$ (substrate) + Orthodianisidine $\xrightarrow[\text{Peroxidase}]{\text{Oxidation-reduction}}$ Colored body (coloration)

*1, Substance related to signal substance generation;
*2, 4-imino-2,5-cyclohexadien-1-one Table 1 shows six typical examples of the signal generation in the assay method of the present invention. In each column of the table, the upper row shows reaction steps using the aforementioned terminology of this invention, and the lower row explains illustrative examples thereof.

The type 1 is an example in which an electrode is used as the detection means "c" and electron transfer is used as the signal. The following describes this type of signal generation with reference to FIG. 1.

In this case, when a substance 14 related to the generation of a signal substance (p-aminophenyl-α-D-galactoside) reaches a signal substance generator (α-galactosidase-labeled specific binding substance) 10 in a channel "b", the substance 14 related to the generation of a signal substance is converted into a signal substance (p-aminophenol) 12. When the signal substance 12 reaches an detection means c$_1$ or c$_2$ (electrode, set at an electric potential of +400 mV (vs. Ag/AgCl)) by diffusion, the signal substance 12 is converted into p-benzoquinone monoimine by oxidation and, at the same time, generates oxidation current (electron transfer) as a signal at each detection means "c". Thereafter, values related to the electron transfer signal are measured as the quantity of electricity or current values.

The type 2 is an example in which an electrode is used as the detection means "c", electron transfer is used as the signal and an electron mediator is used for the transfer of electron. The following describes this type of signal generation with reference to FIG. 1.

The term "electron mediator" as used herein means, in accordance with the present invention, a generic name of oxidation-reduction compounds which mediate between an enzyme reaction and an electrode reaction, thereby rendering possible electron transfer between the two reactions. Such compounds include a substance which does not form substantially irreversible by-products both in the two reactions and is capable of undergoing cycling between the two reactions.

In this case, when a substance 14 related to the generation of a signal substance (a combination of glucose and ferricinium ion as an oxidation type electron mediator) reaches a signal substance generator (glucose oxidase-labeled specific binding substance) 10 in a channel "b", the ferricinium ion is converted into ferrocene which is a reduction type electron mediator to be used as the signal substance 12. When the signal substance 12 reaches an detection means $c_1$ or $c_2$ (electrode, set at an electric potential of +400 mV (vs. Ag/AgCl)) by diffusion, the signal substance 12 is oxidized and reversed into the oxidized state ferricinium ion as the oxidation type electron mediator and, at the same time, generates oxidation current (electron transfer) as a signal at each detection means "c".

In this instance, diffusion transfer of the electron itself between electron mediators by electron hopping or the like and measurement of the resulting signal (electron transfer) generated at the detection means "c" may also be applicable.

In the case of the type 3, when a substance 14 related to the generation of a signal substance (a combination of hydrogen peroxide and a reduction type electron mediator) reaches a signal substance generator (peroxidase-labeled specific binding substance) 10 in a channel "b", the reduction type electron mediator is converted into an oxidation type electron mediator to be used as the signal substance 12. When the signal substance 12 reaches an detection means $c_1$ or $c_2$ (electrode, set at an electric potential of −150 mV (vs. Ag/AgCl)) by diffusion, the signal substance 12 is reduced and reversed into the reduction type electron mediator and, at the same time, generates reduction current (electron transfer) as a signal at each detection means "c".

Illustrative examples of the reduction type electron mediator which becomes the substance 14 related to the generation of a signal substance include hydroquinone, p-phenylenediamine (PPD), N,N-dimethyl-p-phenylenediamine (DMPD), N,N,N',N'-tetramethyl-p-phenylenediamine (TMPD), N,N,N',N'-tetraethyl-p-phenylenediamine (TEPD), N,N,N',N'-tetrakiscarboxymethyl-p-phenylenediamine (TCPD), N,N,N',N'-tetrakis-(2-hydroxyethyl)-p-phenylenediamine (THEPD), N,N,N',N'-tetrakis-(2,3-dihydroxypropyl)-p-phenylenediamine (TDHPD) and the like, of which TDHPD, TCPD and THEPD are particularly preferred.

The type 4 is an example in which an enzyme electrode is used as the detection means "c" and electron transfer is used as the signal.

In this case, it is possible to include an electron mediator and/or an electrically conductive high molecular compound (polypyrrole, polythiophene or the like) as composing elements in the enzyme electrode portion, in order to improve performance of the enzyme electrode. Reaction of a signal substance with a detection means "c" (enzyme electrode) and resulting direct or indirect generation of a signal (electron transfer) are not affected by these composing elements. Preferred examples of the signal substance include a substrate, a cofactor, a coenzyme and the like which correspond to the enzyme electrode.

When the signal substance generates a signal in concert with other substance, that is, when the enzyme electrode generates a signal in the presence of the signal substance and other substance which takes part in the signal generation, the signal generation-related substance may be located on the detection means "c" and/or in an area close to the detection means "c".

In this case, when a substance 14 related to the generation of a signal substance (a combination of glucose and dissolved oxygen) reaches a signal substance generator (glucose oxidase-labeled specific binding substance) 10 in a channel "b", a signal substance (hydrogen peroxide) 12 is formed. When the signal substance 12 reaches an detection means $c_1$ or $c_2$ (peroxidase electrode, set at an electric potential of −150 mV (vs. Ag/AgCl)), the signal substance 12 receives electron from the electrode, mediated or not mediated by an electron mediator, and reacts with a substance 15 related to the generation of a signal (hydrogen ion). In this way, the signal substance 12 is reduced and, at the same time, a signal (electron transfer) is generated at the detection means "c" (peroxidase electrode).

The type 5 is an example in which the detection means "c" is a part where an enzyme (peroxidase) is substantially immobilized and luminescence is used as the signal. Also in this example, a signal substance 12 itself does not generates the signal so that a substance related to the generation of signal is used.

In this case, when a substance 14 related to the generation of a signal substance (a combination of glucose and dissolved oxygen) reaches a signal substance generator (glucose oxidase-labeled specific binding substance) 10 in a channel "b", a signal substance (hydrogen peroxide) 12 is formed.

When the signal substance 12 reaches an detection means $c_1$ or $c_2$ (peroxidase-immobilized part) it changes a substance related to the generation of a signal (luminol) 15 to generate a signal (luminescence).

In consequence, luminescence strength after or until a predetermined period of time is measured at the detection means "c".

The type 6 is an example in which the detection means "c" is a part where an enzyme (peroxidase) is substantially immobilized and coloration is used as the signal. In this example, a signal substance 12 itself also does not generates the signal so that a substance related to the generation of signal is used.

In this case, when a substance 14 related to the generation of a signal substance (a combination of urate and dissolved oxygen) reaches a signal substance generator (uricase-labeled specific binding substance) 10 in a channel "b", a signal substance (hydrogen peroxide) 12 is formed. When the signal substance 12 reaches an detection means $c_1$ or $c_2$ (peroxidase-immobilized part) it changes a substance related to the generation of a signal (orthodianisidine) to generate a signal (coloration).

Thereafter, coloration after or until a predetermined time elapse is measured at each detection means "c" by detecting absorbance or reflected light of the color or visually observing the color.

In the above types 1 to 6, it is possible to exchange the substance 14 related to the generation of a signal substance (corresponds to an enzyme reaction substrate, but not the dissolved oxygen) and the labeling substance (enzyme) which constitutes the signal substance generator 10. In that instance, however, it is preferable to use the enzyme as the labeling substance in view of excellent reaction efficiency.

The following Table 2 shows an example of the combination of an enzyme (a label, a composing element of the signal substance generator in Table 1), which is suitable for use in the generation of a signal substance, with its substrate (a substance related to the generation of the signal substance in Table 1).

the like. Also included are compounds which take part in enzyme reactions as hydrogen donors.

Typical examples of electron mediators are shown in Table 3, though chemically modified products of these examples or other suitable electron mediators can also be used. In addition, electron mediators are not limited to those which change from the oxidation state to the reduction state by the action of the signal substance generator 10, but those having the function to change from the reduction state to the oxidation state may also be used. In the case of horseradish peroxidase for example, a hydrogen donor shown in Table 2, namely a reduction type mediator, is used. Such a mediator can effect the reaction shown in Table 1 in which the signal

TABLE 2

| Enzyme | Substrate | Signal substance to be generated |
|---|---|---|
| Uricase | Urate, $O_2$ | $H_2O_2$ |
| Choline oxidase | Choline, $O_2$ | $H_2O_2$ |
| Cholesterol oxidase | Cholesterol, $O_2$ | $H_2O_2$ |
| Oxalate oxidase | Oxalate, $O_2$ | $H_2O_2$ |
| Sarcosine oxidase | Sarcosine, $O_2$ | $H_2O_2$ |
| Superoxide dismutase | Pyrogallol | $H_2O_2$ |
| Xanthine oxidase | Xanthine, $O_2$ | $H_2O_2$ |
| Glucose oxidase | Glucose, $O_2$ | $H_2O_2$ |
| Horseradish peroxidase | Hydrogen donor (reduction type), $H_2O_2$ | Hydrogen donor (oxidation type) |
| α-Galactosidase | p-Aminophenyl-α-D-galactoside | p-Aminophenol |
| β-Galactosidase | p-Aminophenyl-β-D-galactoside | p-Aminophenol |
| Alkaline phosphatase | p-Aminophenyl phosphate | p-Aminophenol |
| Phosphodiesterase | Bis-p-aminophenyl phosphate | p-Aminophenol |
| Lactate dehydrogenase | Lactate, NAD | NADH |
| Formate dehydrogenase | Formate, NAD | NADH |
| β-Galactose dehydrogenase | Galactose, NAD | NADH |
| 3-Hydroxybutyrate dehydrogenase | 3-Hydroxy butyrate, NAD | NADH |
| Glucose-6-phosphate dehydrogenase | Glucose-6-phosphate, NADP | NADPH |
| 6-Phosphogluconate dehydrogenase | Gluconate-6-phsophate, NADP | NADPH |
| Pyruvate kinase | Phosphoenol pyruvate, ADP | ATP |
| α-Galactosidase | Raffinose | Galactose |
| β-Galactosidase | Lactose | Galactose, glucose |
| Citrate lyase | Citric acid | Oxaloacetatic acid |
| Pyruvate kinase | Phosphoenol pyruvate, ADP | Pyruvate |
| Phosphotglucomutase | Glucose-1-phosphate Glucose-1,6-diphosphate | Glucose-6-phosphate |

Each of the combinations shown in Table 2 can be applied to the signal generation types 1, 4, 5 and 6 described in Table 1.

However, in the case of the type 1 in which a signal is generated by an oxidation-reduction reaction of the signal substance 12 on an electrode, it is preferable to use such a combination that p-aminophenol, hydroquinone, p-cresol or the like is generated as the signal substance 12. Sufficient electron transfer from such a signal substance to an electrode occurs when an electric potential of +several hundred mV is applied based on a silver-silver chloride electrode.

In the case of the signal generation type 2 in Table 1, an oxidation-reduction substance (oxidation state) known as an electron mediator is used as a substrate of Table 2 instead of $O_2$. By the use of such a substance, the reaction shown in Table 1 is effected in which the signal substance 12 (an electron mediator in the reduction state) is generated, electrons are released from the signal substance 12 to an electrode charged with an electric potential corresponding to the electron mediator in the same manner as the case of the type 1, and the electron mediator itself returns to its oxidation state.

A number of substances are known as electron mediators which include metal ions, metal complexes, ruthenium complex compounds, ferrocene compounds, quinone compounds, viologen compounds, porphyrin derivatives and substance 12 (an electron mediator in the oxidation state) is generated, the signal substance 12 accept electrons from electrode at an electrode charged with an electric potential corresponding to the electron mediator in the same manner as the case of the type 1, and the electron mediator itself returns to its reduction state.

TABLE 3

| Typical electron mediator |
|---|
| Ferrocene |
| Vinyl ferrocene |
| Ferrocene aceate |
| Ferrocene monocarboxylate |
| 1,1'-bishydroxymethylferrocene (BHMF) |
| Ru(bpy)$_3$ |
| Os(bpy)$_3$ |
| Fe(bpy)$_3$ |
| Fe(phen)$_3$ |
| Ru(bpy)$_2$(im)$_2$ |
| Mo(CN)$_8$ |
| K$_2$Fe(phen)(CN)$_4$ |
| Co(phen)$_3$Cl$_2$ |
| K$_4$Fe(CN)$_6$ or K$_3$Fe(CN)$_6$ |
| Hydroquinone |
| p-Benzoquinone |
| Catechol |
| p-Quinone-dioxime |

TABLE 3-continued

Typical electron mediator p-Methylphenol
Hydroquinone sulfonate
Hydroxyhydroquinone
p-Phenylenediamine (PPD)
N,N-Dimethyl-p-phenylenediamine (DMPD)
N,N,N',N'-Tetramethyl-p-phenylenediamine (TMPD)
N,N,N',N'-Tetraethyl-p-phenylenediamine (TEPD)
N,N,N',N'-Tetrakiscarboxymethyl-p-phenylenediamine (TCPD)
N,N,N',N'-Tetrakis-(2'-hydroxyethyl)p-phenylenediamine (THEPD)
N,N,N',N'-Tetrakis-(2',3'-dihydroxypropyl)-p-phenylenediamine (TDHPD)
2,6-Dichlorophenolindophenol
1,2-Naphthoquinone
Phenazine methosulfate (PMS)
5-Hydroxy-1,4-naphthoquinone
Pyocyanine
2-Amino-6,7-dihydro-4-pteridone
2-Amino-1,4-naphthoquinone
Anthraquinone-2-sulfate
2-Amino-4-pteridone
Methylviologen ($MV^{2+}$)
Benzylviologen ($BV^{2+}$)
Metal porphyrin Note: bpy, bipyridyl; phen, o-phenanthroline; im, imidazole The following describes substances which take part in the second stage reaction of the two stage enzyme reactions in the signal generation types 4 to 6 shown in Table 1 in which the signal substance 12 formed by the first stage enzyme reaction reacts with other substance to generate a signal.

The type 4 in Table 1 shows an example in which an enzyme electrode is used as the detection means "c". In this case, types of the enzyme used in the enzyme electrode are limited depending on the types of the signal substance 12 generated by the first stage reaction.

For example, when the signal substance 12 generated by the first stage reaction is hydrogen peroxide, an enzyme electrode to which a peroxidase such as horseradish peroxidase or the like has been immobilized may be used as the detection means "c" (cf. J. E. Frew et al., *J. Electoanal. Chem.*, vol. 201, pp. 1–10, 1986; R. M. Paddock and E. F. Bowden, *J. Electoanal. Chem.*, vol. 260, pp. 487–494, 1989; and Ulla Wollenberger et al. *Analytical Letters*, vol. 23, pp. 1795–1808, 1990). When the signal substance 12 is $NAD^+$ or NADH, an enzyme electrode to which diaphorase I of a thermophilic bacterium origin has been immobilized (cf. K. Miki et al., *Analytical Sciences*, vol. 5, pp. 269–274, 1989) may be used as the detection means "c".

When these enzyme electrodes are used as the detection means "c", an electron mediator may be used as a substance related to the generation of a signal in some cases as shown in Table 1. In that case, the electron mediator generates an electron transfer as a signal at the detection means via an enzyme reaction and an electrode reaction.

Examples of the electron mediator are already shown in Table 3.

Chemically modified electrodes are known as analogous means of the enzyme electrode, which are disclosed for instance by R. W. Murray (Chemically Modified Electrode, *Electroanalytical Chemistry*, vol. 13, pp. 191–368, Marcel Dekker, Inc., New York, 1084), by K. Nakamura, M. Aizawa and O. Miyawaki (*Electroenzymology Coenzyme Regeneration*, Springer-Verlag, Berlin, 1988) and by V. J. Razumas, J. J. Jasaitis and J. J. Kulys, *Bioelectrochemistry and Bioenergetics*, vol. 12, pp. 297–322, 1984).

When the signal is fluorescence or luminescence like the case of the type 5 signal generation system shown in Table 1, substances which take part in the second stage reaction (an enzyme and a fluorescence or luminescence substance as a substrate of the enzyme) are restricted depending on the types of the signal substance 12 formed by the first stage reaction.

For example, when the signal is fluorescence and the signal substance 12 is hydrogen peroxide, a typical combination of the substances related to the second stage reaction may be peroxidase with 4-hydroxyphenyl acetate or 3-(4-hydroxyphenyl) propionate.

When the signal is luminescence, the following combinations may be used. That is, when the signal substance 12 is ATP, a typical combination of the substances related to the second stage reaction may be firefly luciferase with luciferin and $Mg^{2+}$. When the signal substance 12 is NADH, the combination of the substances related to the second stage reaction may be NAD(P)H:FMN oxidoreductase and a luciferase of luminescent bacterium origin with FMN and a saturated long chain aliphatic aldehyde such as tetradecanal.

In these examples, each of the detection means $c_1$ and $c_2$ may be constructed by immobilizing at least one of the substances which take part in the second stage reaction, but preferably an enzyme from a reaction efficiency point of view.

When fluorescence or luminescence is used as a signal, it is possible to generate the signal from the signal substance 12 itself, like the case of the type 1 signal generation system shown in Table 1.

For example, luciferin is formed as the signal substance 12 when a luciferin derivative such as D-luciferin-o-phosphate is used as the substance related to the generation of the signal substance 12 and alkaline phosphatase is used as a labeling agent which constitutes the signal substance generator 10, and luminescence (signal) is generated when luciferin is treated with luciferase in the presence of ATP and $Mg^{2+}$.

In this instance, each of the detection means $c_1$ and $c_2$ may be constructed by immobilizing at least one of ATP, $Mg^{2+}$ and luciferase, but preferably luciferase from a reaction efficiency point of view.

When the signal is coloration like the case of the type 6 signal generation system shown in Table 1, substances which take part in the second stage reaction (an enzyme and a precursor of a coloring body as a substrate of the enzyme) are also restricted depending on the types of the signal substance 12 formed by the first stage reaction.

For example, when the signal substance 12 is hydrogen peroxide, a typical combination of the substances related to the second stage reaction may be peroxidase with a coloring substance precursor such as 5-aminosalicylic acid, o-dianisidine, 2,2'-azino-di-(3-ethylbenzothiazoline-6-sulfonate) diammonium salt (ABTS), 3-methyl-2-benzothiazolinehydrazone (MBTH) and 3-(dimethylamino) benzoic acid (DMAB), or o-tolidine, 3,3'-diaminobenzidine ((DAB), 1,2-phenylenediamine, 3,3',5,5'-tetramethylbenzidine or the like.

When the signal substance is NADH, the combination of the substances related to the second stage reaction may be diaphorase with a coloring substance precursor such as iodonitrotetrazolium violet.

In these examples, each of the detection means $c_1$ and $c_2$ may be constructed by immobilizing at least one of the substances which take part in the second stage reaction, but preferably an enzyme from a reaction efficiency point of view.

Thus, though not particularly limited, illustrative examples of the signal generation mechanism in the assay method of the present invention have been described.

As described in the foregoing, the assay device for use in the specific binding assay of the present invention basically comprises a sample-introducing means "a", a channel "b" and a plurality of detection means "c". When required, a substance related to the generation of a signal substance and/or a substance related to the generation of a signal may be located at an appropriate liquid sample-flowing part of the assay device.

The sample-introducing means "a" is an entrance connected to the channel "b" for use in the introduction of liquid samples and the like into the channel "b" from its predetermined site.

Though the sample-introducing means "a" is generally used as a liquid sample-introducing entrance connected to the channel "b", it may be used also as a space where a liquid sample necessary for the assay is temporarily stored. As occasion demands, the sample-introducing means "a" may be equipped with a filter capable of removing contaminants and the like.

Also, an impregnation portion may be arranged between the sample-introducing means "a" and the channel "b", which is impregnated with various substances required for the reaction, such as the signal substance generator 10, the substance 14 related to the signal substance generation, a substance related to the signal generation, a specific binding substance and the like.

The channel "b" is a portion connected to the downstream side of the sample-introducing means "a", where an introduced liquid sample is allowed to flow and a distribution of the signal substance generator 10 is formed in response to the amount (concentration) of a substance to be assayed in the liquid sample.

According to the present invention, it is desirable to allow the liquid sample to flow spontaneously on the channel "b" without applying an external force such as of a pump, in order to simplify the assay operation. Because of this, it is desirable to construct the channel "b" with a capillary or narrow gaps or a porous member. Construction of the channel "b" with a capillary or porous member will provide additional effects such as increase in the efficiency of the specific binding reaction and formation of clear distribution of the signal substance generator.

As occasion demands, an absorption means may be connected to the downstream side of the channel "b", in order to enhance spontaneous flow of the liquid sample and to increase volume of the liquid sample passing through the channel "b".

The channel "b" is prepared from for example a porous carrier or a gel carrier. In the case of a gel carrier, it is preferable to use a material which becomes the state of gel or sol when contacted with a test sample. A porous carrier is preferably in any case.

Alternatively, a porous carrier may be impregnated with a water soluble high molecular compound and then dried to use as the channel "b". A material in which a solid substance is kept in the porous carrier or the like may also be used as the channel "b".

Illustrative examples of the porous carrier include: porous membranes made of cellulose acetate, cellulose nitrate, nylon and the like; filter papers made of glass fibers, cellulose fibers and the like; and porous ceramics and the like. Illustrative examples of the gel carrier include agar, agarose, dextran, polyacrylamide and the like. Illustrative examples of the aforementioned water soluble high molecular compound include starch and derivatives thereof, mannan, galactan, agar, sodium alginate, gum arabic, dextran, gelatin, casein, collagen, methyl cellulose (MC), ethyl cellulose (EC), hydroxyethyl cellulose (HEC), carboxymethyl cellulose (CMC), polyvinyl alcohol (poval), sodium polyacrylate and the like. Illustrative examples of the solid substance described above include porous particles such as of dextran and the like, latexes made of polystyrene and the like, and fine particles such as of glass and the like or modified products thereof produced by adding active groups for binding use.

Since the channel "b" is a site where a specific binding reaction is carried out as described in the foregoing, constitution of this part exerts a great influence on the detection results.

In consequence, it is desirable to constitute the channel "b" in such a manner that it can show appropriate properties in response to the kind of substances to be assayed, the type of specific binding reactions (for example, competitive type and sandwich type) and the like conditions. That is, distribution conditions of a signal substance generator and diffusion velocities of a signal substance and the like are optionally controlled by selecting appropriate construction material of the channel "b" and adjusting its size (thickness), pore size and viscosity (consistency) when changed to the state of gel.

Also, properties of the channel "b" can be controlled minutely when it is constructed from a plurality of structures and materials, such as a laminated body or the like.

For example, difference in the distribution of a signal substance generator after a specific binding reaction in response to the amount of a substance to be assayed can be detected more clearly when a construction material having a small pore size is used in the vicinity of the detection means $c_1$ and $c_2$ and another construction material having a large pore size is used in its sample-introducing means "a" side. Such an effect may be realized by the use of a polyacrylamide gradient gel or a laminated porous membranes having different pore sizes.

When a specific binding substance for a substance to be assayed is included or immobilized in the channel "b", it may be included or immobilized uniformly in the entire area of the channel, or localized in a part of the channel "b". Alternatively, a density gradient may be effected by including or immobilizing the specific binding substance in a large amount in the upstream area of the channel and in a small amount in its downstream area.

Immobilization of a specific binding substance for a substance to be assayed in the channel "b" may be attained by immobilizing it in a porous carrier or a gel carrier through covalent bonding or adsorption. In addition, when the channel "b" is constructed from a plurality of members, from a porous carrier and a water soluble high molecular compound or from a porous carrier or the like and a solid state substance to be kept therein, immobilization of the specific binding substance may be applied to all of the channel-composing elements or to a part of them.

Length of the channel "b" in the sample flow direction of the assay device of the present invention may be generally in the range of from about 10 μm to several tens in mm, because necessary amount of a liquid test sample can be minimized by reducing the channel length, but changes in the distribution of a signal substance generator in response to the amount of a substance to be assayed in the test sample become unclear when the channel length is too small.

The detection means "c" is a portion by which a signal generated by a signal substance gotten thereto can be measured as its degree of modulation with the naked eye or using an external instrument appropriately selected depending on the type of each signal, which is arranged in the direction of the liquid sample flow in plural numbers at different positions where they can receive the signal substance 12 from the channel "b".

At least one of the plural detection means "c" may be arranged at a position where the signal modulation generated from the positional distribution of the signal generator 10 in the channel "b" is large. In general, such a position is the most downstream or upstream side in the channel "b".

The other detection means may be arranged also at a position where the signal modulation generated from the positional distribution of the signal generator 10 in the channel "b" is large or at a position where it can hardly receive the signal modulation generated from the positional distribution of the signal generator 10 in the channel "b".

However, the inventive assay method making use of a plurality of detection means cannot be effected when the plural detection means are completely the same with each other with regard to the changes in the positional distribution of the signal substance generator in the channel "b" so that a difference in the signal modulation cannot be observed between these detection means.

In consequence, according to the present invention, a plurality of the detection means are arranged at different positions in the liquid flow direction of the channel "b". Since changes in the distribution of the signal substance generator in the channel "b" in response to the amount of a substance to be assayed occur basically in the flow direction of the liquid sample, signal modulations detected at a plurality of detection means do not become equal when they are arranged at different positions in the liquid flow direction in the channel "b".

Detection methods at the detection means are not particularly limited, and various known methods can be applied depending on each signal generated by a signal substance (or a signal generated by the detection means via a signal substance). Particularly preferred are electrochemical measuring methods.

For example, when the signal is electrochemical, various types of working and reference electrodes can be used as the detection means, such as a platinum electrode, a gold electrode, a carbon electrode and the like, of which a carbon print electrode is particularly preferred from a production point of view. In this case, a liquid-impermeable plate such as a PET film, a vinyl chloride plate, a glass plate or the like or a liquid-permeable sheet such as a filter paper or the like may be used as an electrode base. When a minute electrode constitution is required, a microarray electrode may be constructed.

An Ag/AgCl electrode or the like may be used as a reference electrode of the above electrode, which can be produced making use of printing techniques and the like.

Specificity and sensitivity of the electrode reaction can be improved when an enzyme electrode is used as the detection means "c". In that instance, a signal substance functions as a substrate or a cofactor of the enzyme electrode, and a signal is detected when electron transfer is effected on the electrode. Various types of the enzyme electrode are known in the fields of biochemical analysis and analytical chemistry.

When the signal is fluorescence, luminescence, coloring or the like, the detection means "c" is actually an luminescence generation part where a substance which takes part in at least one signal generation necessary for the luminescence reaction is substantially immobilized, a fluorescence generation part where a substance which takes part in at least one signal generation necessary for the fluorescence reaction is substantially immobilized or a color generation part where a substance which takes part in at least one signal generation necessary for the coloring reaction is substantially immobilized.

When the detection means "c" is a site where fluorescence, luminescence, coloring or the like is detected, the detection means "c" may be prepared by immobilizing the aforementioned signal generation-related substance in an area of the aforementioned channel "b" or of a portion of an absorption means which will be described later, or on a base when the base is arranged in the downstream side of the detection means "c". In that instance, the immobilization may be effected by various means, for example, by binding an enzyme of interest using glutaraldehyde to the surface of a glass base which has been treated with 3-aminopropyltriethoxysilane.

In addition to the aforementioned composing elements, the assay device of the present invention may have a support (or base) and a cover.

Figure 2:
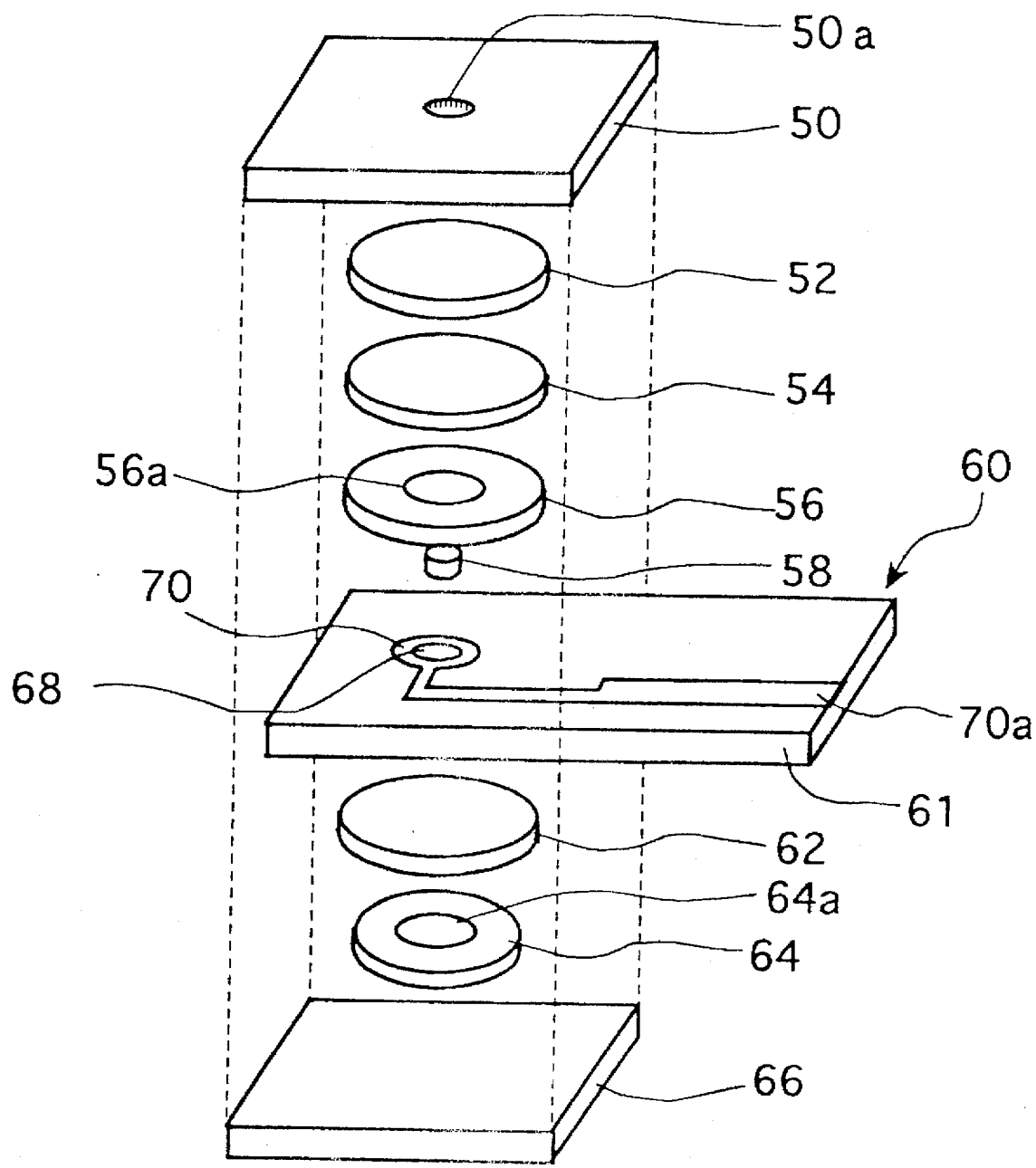
FIG. 2 is a graph showing a schematic exploded perspective view of the specific binding assay device of the present invention.
Figure 3:
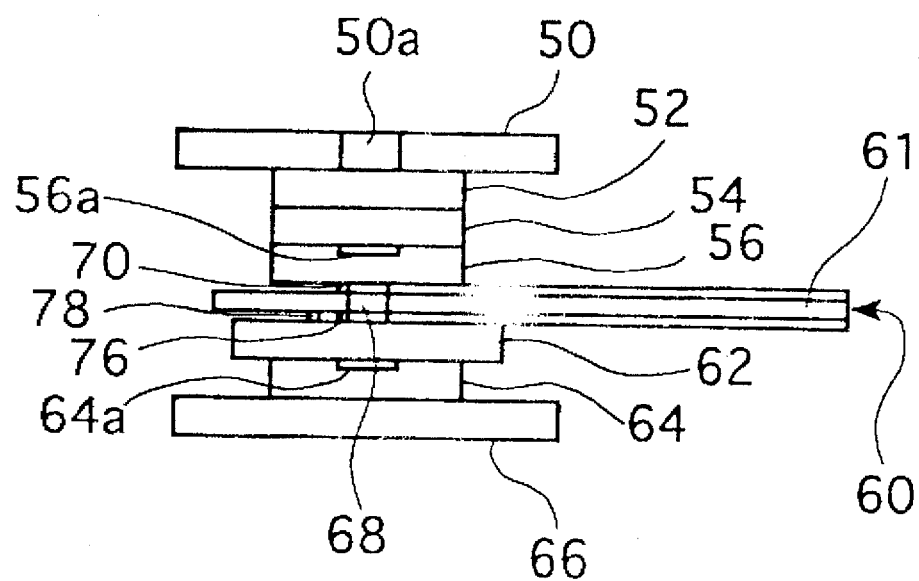
FIG. 3 is a graph showing a schematic sectional drawing of the assembled specific binding assay device shown in FIG. 2.

FIG. 2 shows an exploded perspective view of an example of the specific binding assay device of the present invention in which the measurement is carried out based on an electrochemical signal, and FIG. 3 shows its sectional view when assembled.

The assay device shown in FIG. 2 is composed of an upper cover 50, a filter 52, a first impregnation portion 54, a second impregnation portion 56, a communication means 58, an electrode portion 60 having a plurality of detection means, a channel (matrix) 62, an absorption means 64 and a lower base 66 in that downward order, and these members are assembled by superposing them upon one another in such order as shown in FIG. 3.

In the illustrated device, a sample-introducing means is composed of the upper cover 50 (its sample-introducing hole 50a), the filter 52, the first impregnation portion 54, the second impregnation portion 56 and the communication means 58.

In this instance, the filter 52, the first impregnation portion 54, the second impregnation portion 56 and the communication means 58 are arranged as occasion demands or as a preferred mode in response to the specific binding substance to be used in the assay or the construction of the device, so that the present invention is not restricted by these members. In other words, according to the present invention, the sample-introducing means may be formed by using only the sample-introducing hole 50a through which a liquid sample is introduced directly into a channel 62 or by combining it with other optionally selected members depending on each purpose.

The upper cover 50 is formed from various materials as described in the foregoing, and its central portion has the sample-introducing hole 50a for use in the injection of a liquid sample.

The filter 52 is generally made of woven fabric, non-woven fabric or the like and, in case of need, the filter 52 may be used for the purpose of removing solid materials (interfering materials) which are contained in test samples and unnecessary for the assay and of effecting uniform introduction of the test sample.

Each of the first impregnation portion 54 and the second impregnation portion 56 is optionally arranged depending on the type of the liquid sample, the substance to be assayed, the specific binding reaction to be applied and the like, and prepared by impregnating a piece of glass fiber filter paper, cellulose fiber filter paper, non-woven fabric or the like with various substances and then drying the impregnated piece. Examples of such impregnating substances include a signal substance generator, a substance related to the generation of a signal substance, a substance related to the generation of a signal, an electron mediator and its stabilizing or protecting agent, a salt component for use in the adjustment of ionic strength and/or pH, a buffer solution, a liquid sample flow-smoothing agent such as a surface active agent or the like.

As a liquid sample passes through the first impregnation portion 54 and the second impregnation portion 56, a signal substance generator and the like are eluted and mixed with the liquid sample or the reaction starts.

As a matter of course, a plurality of substances may be kept in one impregnation portion, or the first impregnation portion 54 and the second impregnation portion 56 may be made into a single impregnation portion.

On the other hand, the use of the first impregnation portion 54 and the second impregnation portion 56 renders possible prolongation of the flowing time of test samples to obtain sufficient reaction time.

In the example shown in the drawing, a water-impermeable sealing means 56a is formed on the central portion of the upper surface of the second impregnation portion 56 as a preferred mode.

By the use of the sealing means 56a, the sample flow originally vertical in direction can be changed to the horizontal direction, which renders possible prolongation of the flowing time of test samples to obtain sufficient reaction time and simultaneous improvement of the reaction efficiency through the mixing effect, hence resulting in the realization of more accurate measurement. Materials and methods for the formation of the sealing means 56a are not particularly limited, and it may be formed by adhering a water-impermeable material selected from various sources such as vinyl chloride, cellulose acetate, polyester and the like to the central portion of the second impregnation portion 56 using an adhesive such as an acrylic adhesive or the like.

As described in the foregoing, the first impregnation portion 54, the second impregnation portion 56 and the like are not essential elements of the assay device (assay method) of the present invention, and when these members are not used (when they are not impregnated with a signal substance generator and the like), the signal substance generator and the like essential substances may be introduced into the reaction system for example by mixing them in advance with a liquid sample or injecting them from the sample-introducing hole 50a before or after injection of the liquid sample.

The communication means 58 is used to introduce the liquid sample and the like which passed through the second impregnation portion 56 into the channel 62 via a through hole 68 of an electrode portion 60, which is formed from glass fiber filter paper, cellulose fiber filter paper or the like.

As occasion demands, the communication means 58 is arranged by inserting it into the through hole 68 of the electrode portion 60 which will be described later. This means may not be required when thickness of an electrode substrate 61 is not large.

The electrode portion 60 is composed of a plurality of detection means "c" which are essential elements of the present invention. In the device shown in the drawing, the electrode portion 60 is arranged by forming a reference electrode on the upside of the insulating substrate 61 made of PET (polyethylene terephthalate) or the like, and a working electrode to be used as a detection means on its backside, and an electric signal generated in response to a signal substance generator distribution formed in the channel 62 is detected by the working electrode.

Figure 4:
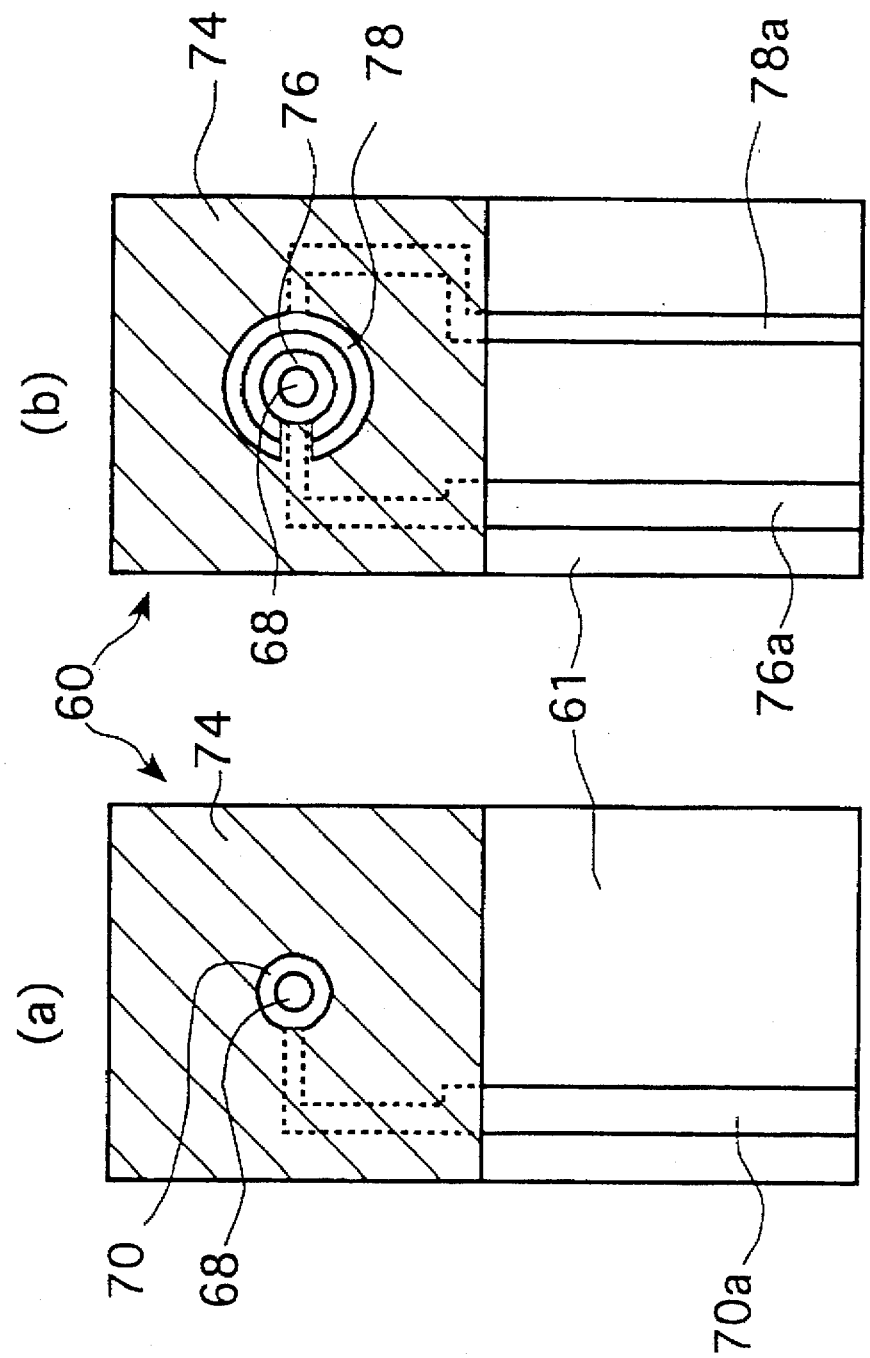
FIGS. 4A and 4B are graphs showing upside (FIG. 4A) and downside (FIG. 4B) of the electrode portion of the specific binding assay device shown in FIG. 2.

The upside of the electrode portion 60 is shown in FIG. 4(a), and its backside in FIG. 4(b).

On the upside of the electrode portion 60 shown in the drawing, a circular counter electrode (reference electrode) 70 and its terminal 70a are formed, as well as an insulating layer 74 shown by a shaded portion excluding the counter electrode 70.

On the backside of the electrode portion 60, on the other hand, a circular first working electrode 76 and its terminal 76a are formed similar to the case of the upside, in addition to a roughly circular second working electrode 78 having the same center with and a larger size than those of the first working electrode 76, as well as its terminal 78a. Also formed on the backside is an insulating layer 74 shown by a shaded portion excluding the first working electrode 76, the second working electrode 78 and a gap between them. That is, the first working electrode 76 in the illustrated example corresponds to the first detection means $c_1$ of FIG. 1, and the second working electrode 78 to the second detection means $c_2$.

In addition, a through hole 68 is formed in the insulating substrate 61 penetrating the inside of the counter electrode 70 and the first working electrode 76.

As described in the foregoing, a liquid sample is introduced into the channel 62 which will be described later, through the through hole 68 or, as occasion demands, through a communication means 58 inserted into the through hole 68.

Because of this, according to the illustrated device, the liquid sample in the channel 62 flows radially in outside directions from the center of the through hole 68, namely the first working electrode 76. In consequence, as shown in the illustrated example, the first working electrode 76 and the second working electrode 78 are arranged at different positions in the liquid sample flowing direction, by making the electrodes (detection means) into circular forms having the same center but different sizes so that the liquid sample flows from the center. Though not particularly limited, the first working electrode 76 and the second working electrode 78 may preferably have a gap of 10 μm or more as described in the foregoing.

The first working electrode 76 and the second working electrode 78 to be used as the detection means are formed from the aforementioned various materials. The counter electrode 70 is formed as a silver electrode, a silver/silver chloride electrode or the like.

The substrate 28 is formed from various known insulating materials such as PET, polyvinyl chloride, polyimide, polyester and the like.

The insulating layer 36 is formed from various known insulating ink materials such as acrylic resins, polyesters and the like.

Each of the working electrodes, the counter electrode (reference electrode) and the insulating layer in the illustrated device can be formed by known film forming techniques such as screen printing, doctor knife and the like thick film forming techniques or sputtering, CVD and the like thin film forming techniques.

Figure 5:
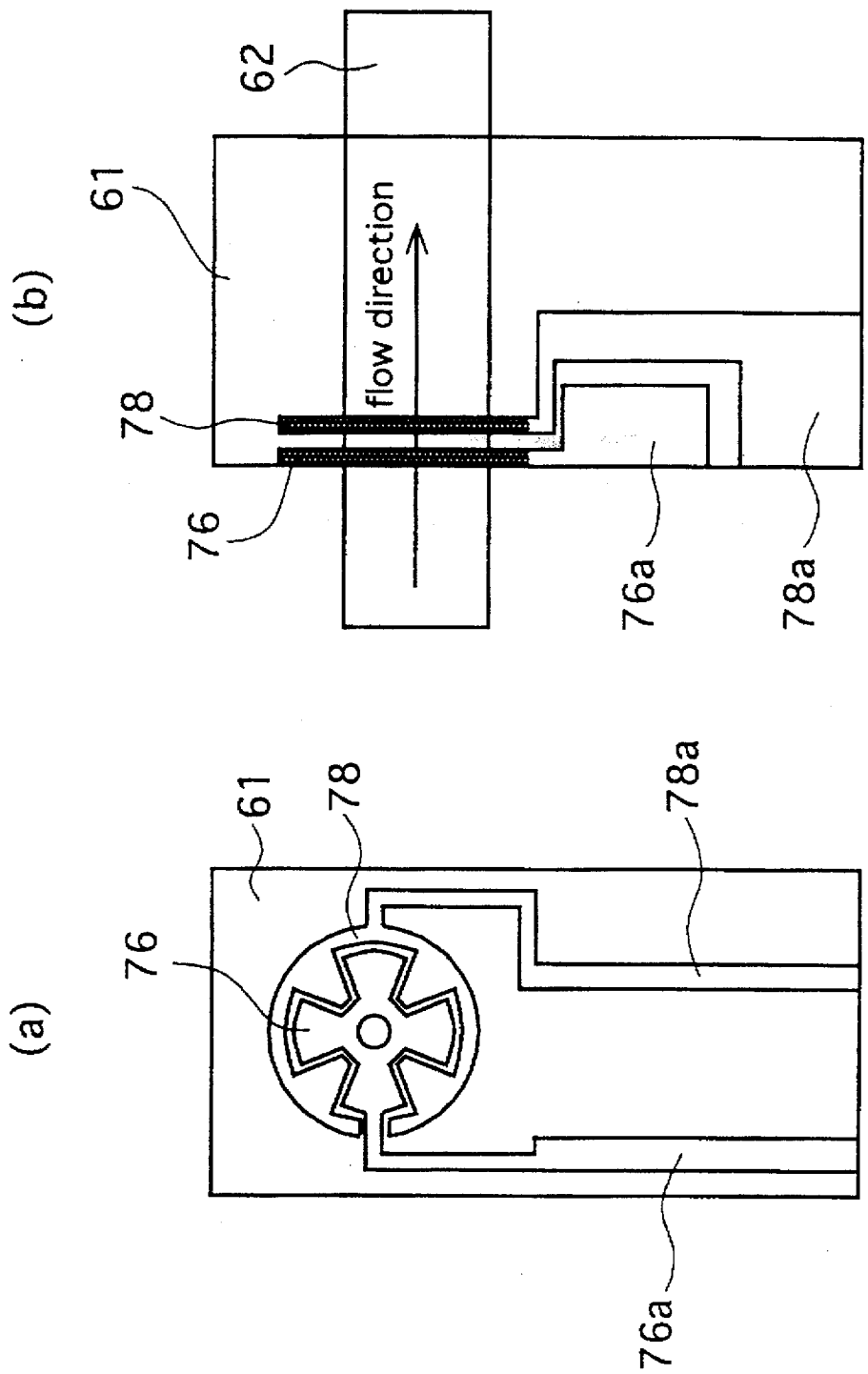
FIGS. 5A and 5B are graphs showing (FIG. 5A) the down side of an electrode portion having two electrodes to be used in the specific binding assay device shown in FIG. 2 and (FIG. 5B) the downside of an electrode portion having two electrodes on one strip-type channel (matrix) to be used in another type device of the present specific binding assay.

According to the present invention, the first working electrode 76, the second working electrode 78 and the like are not particularly limited to the illustrated circular shape and can be made into various shapes such as those shown in FIGS. 5A and 5B, provided that they are arranged at different positions (preferably with a certain distance) in the flow direction of a liquid sample.

Figure 6:
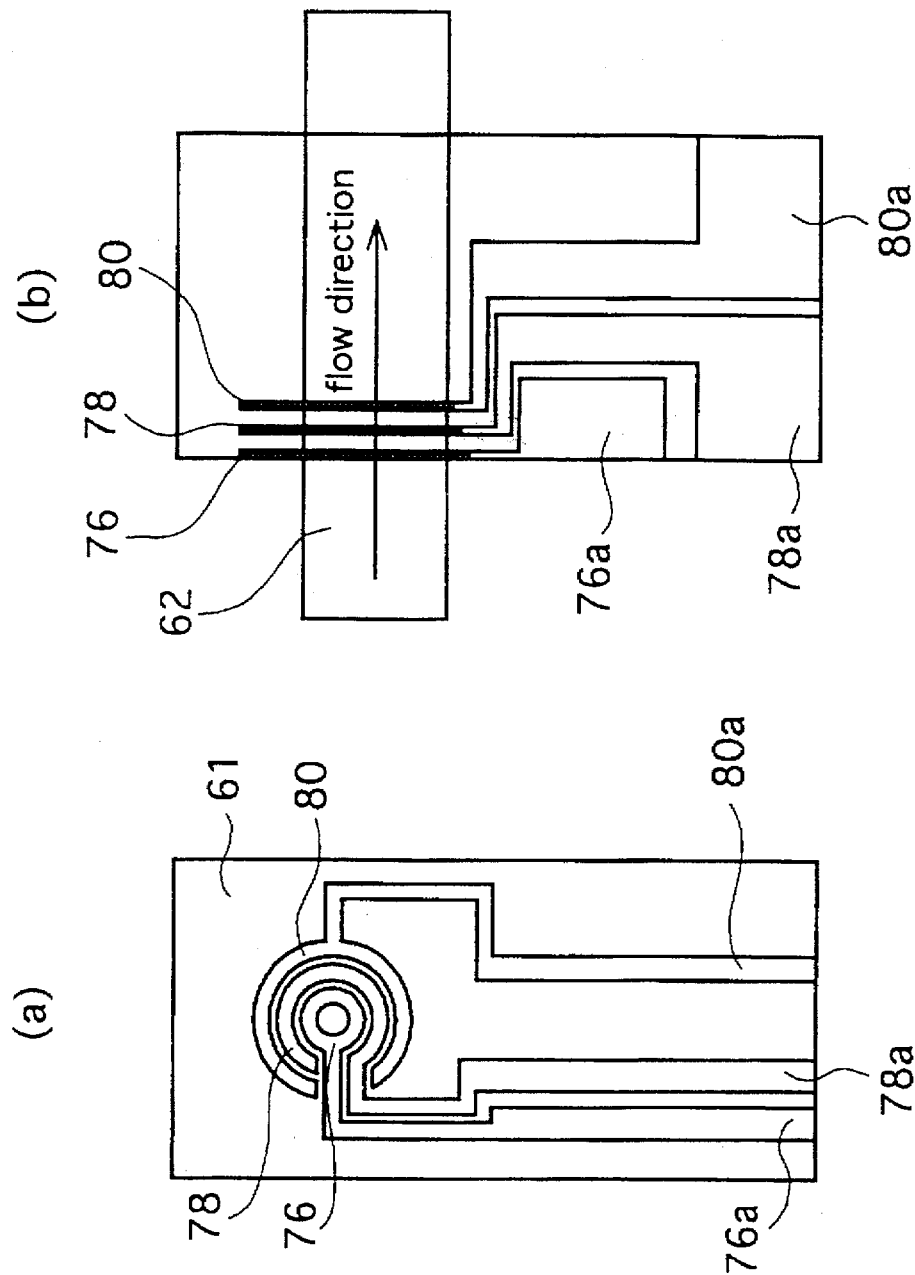
FIGS. 6A and 6B are graphs showing (FIG. 6A) still another example of the down side of an electrode portion having three electrodes to be used in the specific binding assay device shown in FIG. 2 and (FIG. 6A) the downside of an electrode portion having three electrodes on one strip-type channel (matrix) to be used in another type device of the present specific binding assay.

Also, according to the present invention, the plural detection means are not limited to two, and three, or even more, working electrodes may be formed as shown in FIGS. 6A and 6B.

In addition, though detection is carried out within the peripheral area of the central position where a liquid sample is introduced into the channel 62 in the illustrated example of the device, the working electrodes may also be arranged at different positions in a linear of one direction as shown in FIGS. 5(b) and 6(b).

The channel 62 functions as the channel "b" of the specific binding assay device of the present invention, where, for example, a substance to be assayed and an antibody capable of binding specifically to a signal substance generator are fixed by immobilization, and a distribution of the signal substance generator is formed in response to the amount of the substance to be assayed in a liquid sample via a specific binding reaction of the substance to be assayed and the like. Positional distributions of the signal substance generator from the first working electrode 76 and the second working electrode 78 are measured as current values via the signal substance.

The channel 62 is formed in the same manner as the case of the aforementioned channel "b", for example by a method in which antibody, antigen, nucleic acid or the like molecules for use in the specific binding reaction are fixed to a porous membrane by immobilization and then dried.

Excess amount of a liquid sample passed through the channel 62 is absorbed by an absorption means 64.

The absorption means 64 absorbs excess amount of a liquid sample passed through the channel 62 as described above and is formed from for example a cellulose filter paper such as a chromatography filter paper or the like or a polymer having high water absorbing capacity. The absorption means 64 may be impregnated in advance with a substance related to the generation of a signal substance and/or a signal.

In the illustrated example of the assay device, a water impermeable sealing means 64a is formed on the central portion of the upper surface of the absorption means 64 as a preferred mode of the present invention.

Similar to the case of the aforementioned sealing means 56a, the use of the sealing means 64a renders possible alteration of the sample flow originally vertical in direction to the horizontal direction, so that the flowing time of test samples can be prolonged to improve the reaction efficiency and more accurate measurement can be made due to the clear distribution of signal substance generator (labeled body) in the channel.

In the example of the assay device shown in FIG. 2, when the two detection means 76 (see FIG. 4) and 78 (see FIG. 4) are positioned within the width of the sealing means 64a, both specific signal intensity components and non-specific signal intensity components can be detected at the respective detection means 76 and 78. When the detection means 76 is positioned within the width of the sealing means 64a and the other detection means 78 is positioned far from the width of the sealing means 64a, the detected signal at the detection means 78 has less specific signal intensity components. If the detection means 78 is positioned far enough from the sealing means 64a, specific signal intensity components are hardly detected at the detection means 78.

The sealing means 64a can be formed in the same manner as the case of the aforementioned sealing means 56a.

The illustrated example of the assay device can be prepared by superposing these members one upon another in the order shown in FIGS. 2 and 3 on a lower base cover 66, and fixing these laminated members between the upper cover 50 and the lower base cover 66 using screws, bolts and nuts and the like.

In such a type of assay device, a liquid sample is injected through the sample introducing hole 50a formed in the upper cover 50 as described in the foregoing.

The liquid sample injected through the sample introducing hole 50a passes through the filter 52 where contaminants and the like are removed, flows into the first impregnation portion 54 and then into the second impregnation portion 56. By the flow of the liquid sample into these impregnation portions, dried and fixed signal substance generator and the like are eluted and mixed with the test sample or the specific binding reaction of the substance to be assayed starts.

In the illustrated example, the sealing means 56a is formed on the upper surface of the second impregnation portion 56, so that the flow direction of a liquid sample changes from vertical to horizontal to ensure sufficient reaction time as described in the foregoing.

The liquid sample passed through the second impregnation portion 56 then passes through the through hole 68 of the electrode portion 60 via the communication means 58 and flows into the channel 62.

When the liquid sample flows into the channel 62, distribution of the signal substance generator is formed in response to the specific binding reaction of the substance to be assayed in the liquid sample, the signal substance generated by the action of the signal substance generator reaches the first working electrode 76 or the second working electrode 78 by diffusion, and distribution of the signal substance generator in the radial direction of each working electrode in the channel 62 is detected as an electrochemical signal in response to the reaction.

Excess amount of the liquid sample passes through the channel 62 to be absorbed by the absorption means 64.

The output from the first working electrode 76 or the second working electrode 78 (not only an electric signal but also other output from various detection means) is measured by adding a predetermined amount of the liquid sample to the sample introducing means and reading the output after a predetermined lapse of time or continuously until a predetermined lapse of time.

Measurement of signals at a plurality of detection means may be carried out either simultaneously or separately. When measurement of signals at a plurality of detection means is carried out separately, each detection means may be measured repeatedly in turn.

The data may be read for example as an output strength (for example, current value) after a predetermined lapse of time, as an average of output strength values within a predetermined period, as a time until the output reaches a predetermined strength, as an integrated value of continuous output (for example, charge quantity), or as a time until the charge reaches a predetermined value.

As described in the foregoing, according to the assay method of the present invention in which a specific binding reaction is used, more accurate specific binding assay can be achieved by arithmetically processing measured results of signals, making use of an arithmetic expression by which the influence of various non-specific factors other than the amount of a substance to be assayed contained in a liquid sample can be minimized from the signals detected at a plurality of detection means arranged at different positions in the flow direction of the liquid sample.

In this connection, when the amount of a substance to be measured in a liquid sample is C, the amount of contaminants in the sample which exerts influence upon the signal strength of the detection means is Z and signal strengths of a plurality of the detection means are $I_1, I_2, \ldots I_n$, the following formulae $$I_1 = f_1(C,Z) \therefore Z = g_1(I_1,C) \quad \text{formula (1)-1}$$

$$I_2 = f_2(C,Z) \therefore Z = g_2(I_2,C) \quad \text{formula (1)-2}$$

$$\vdots$$

$$I_n = f_n(C,Z) \therefore Z = g_n(I_n,C) \quad \text{formula (1)-n}$$

are obtained, and the term Z can be eliminated from at least two optional formulae.

For example, the following formula (2) can be obtained from the formulae (1)-1 and (1)-2.

$$g_1(I_1, C) - g_2(I_2, C) = 0$$

$$\therefore h_1(I_1, I_2, C) = 0 \quad \text{formula (2)}$$

Since the formula (2) is just an equation for use in the calculation of the unknown amount C of a substance to be assayed from the measured signal strength $I_1$ and the measured signal strength $I_2$, the amount C of the substance to be assayed can be obtained from the following formula (3) which is the solution of the equation.

$$C = k_1(I_1, I_2) \quad \text{formula (3)}$$

In consequence, it is possible to obtain the amount C of the substance to be assayed, which is free from the influence of the amount Z of contaminants in the test sample, from the measured results of at least two detection means. In addition, when measured results of more than two detection means are obtained, the amount C can be obtained with more high accuracy by stochastic treatment.

However, the amount C cannot be obtained when signals detected by two detection means are the same, namely when the formula (1) is as follows.

$$I_1 = f(C, Z)$$

$$I_2 = f(C, Z)$$

$$\therefore I_1 = I_2$$

According to the specific binding assay method of the present invention, a distribution of a signal substance generator is formed in the channel in response to the amount of a substance to be assayed, by at least one specific binding reaction with the substance to be assayed in a liquid sample, to measure a signal which is rate-determined by the diffusion of a signal substance that travels by diffusion from the signal substance generator to the detection means to generate the signal. In general, therefore, the signal strengths of two detection means become different functions against the amount C of the substance to be assayed when a plurality of detection means are arranged at different positions in the liquid flow direction.

In general, the term "different positions in the liquid flow direction" means that detection means are respectively positioned upstream and downstream of the liquid flow direction. However, there is a possibility that the plural detection means have a positional overlap in the liquid flow direction when the electrode size is large or depending on the shape of the electrode. Even such a case of plural detection means can be regarded as those which are arranged at different positions in the liquid flow direction, because a difference in the signal strength can be expected when geometric centers of electrodes or their edges are different from each other. In a preferred mode, geometric centers of electrodes or their edges are arranged having a distance of 10 μm or more.

Thus, according to the specific binding assay method and device of the present invention, the use of a plurality of detection means renders possible minimization of various non-specific influences which do not substantially take part in the distribution of a signal substance generator in the channel formed by a specific binding reaction with a substance to be assayed.

The following itemizes examples of main measurement error factor Z which can be minimized in the specific binding assay method and device of the present invention.

I. Non-specific factors due to contaminants in and properties of test samples including:

sample-derived activities analogous to a signal substance generator, such as a sample-derived peroxidase activity when the signal substance generator is horseradish peroxidase;

sample-derived substances which inhibit a signal substance generator or a signal substance, such as ascorbic acid, uric acid and the like oxidation-reduction substances and a catalase activity when a substance related to the generation of a signal substance is hydrogen peroxide; and sample properties such as a sample viscosity which exerts influence upon the diffusion constant of a signal substance, pH, ionic strength and cofactor concentration, which exert influence upon the activity of a signal substance generator and hematocrit value and the like of total blood samples.

II. Assay environments such as reaction temperature and the like.

III. Changing degrees of reagent component activities, caused by inactivation and the like, such as changes in the activity of a signal substance generator, changes in the activity of a substance related to the generation of a signal substance and changes in the activity of a substance related to the generation of a signal.

Though some of these factors have a possibility of substantially exerting influence upon distribution of a signal substance generator in the channel formed by a specific binding reaction with a substance to be assayed, the specific binding assay method and device of the present invention can minimize their non-specific influential portions which do not substantially take part in the distribution of the signal substance generator in the channel formed by the specific binding reaction with the substance to be assayed.

That is, though Z was defined in the above description of mathematical formulae as the amount of contaminants in a test sample which exert influence upon the signal strength of the detection means, the same explanation can generally be made when Z is the non-specific factor of the above described item I due to contaminants in and properties of test samples, the assay environment factor of the item II or the reagent component inactivation factor of the item III.

Since these factors Z have given values in any assay of any test sample, the same explanation can be made when these factors are defined as a synthetic parameter.

In other words, in the signal detecting system of the present invention, as exemplified in FIG. 27, a signal substance (electron mediator, etc.) is generated by a signal substance generator (labeling enzyme, etc.), and the generated signal substance is detected as a signal (electric current, etc.) by use of suitable detection means (electrode, etc.). Accordingly, the intensity of signal detected is dependent largely on the distance of diffusion, or substantially on the distribution of distances to the detection means, or, the distribution of numerous molecules of signal substance generator in the channel (namely, the positional distribution of signal substance generator).

Figure 28:
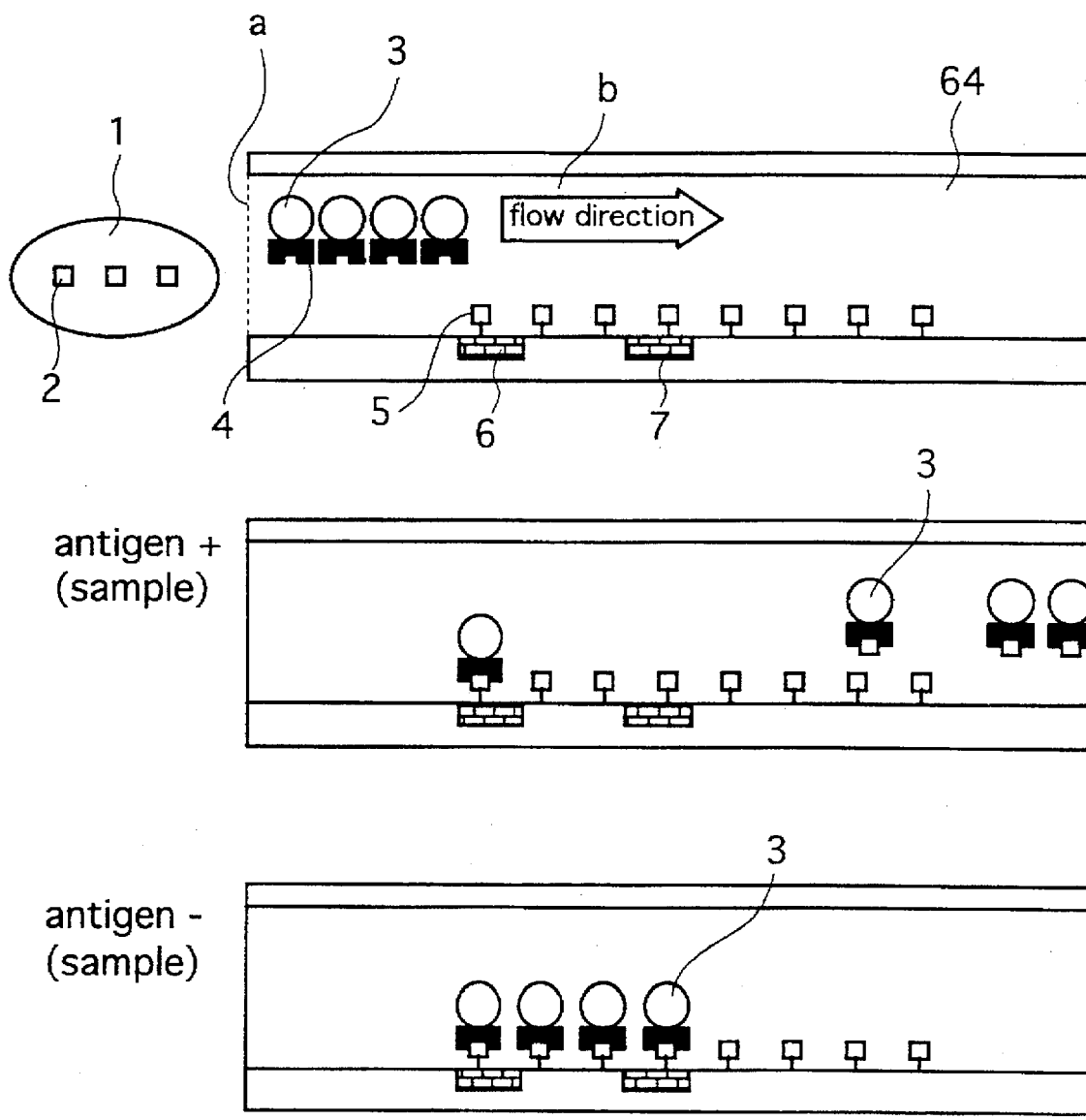
FIG. 28 is a schematic view showing the relation between whether antigens are present or not in a sample and the distribution of the labeling enzymes (signal substance generators) in a channel by competitive type MEDIA method of the invention.

As exemplified in FIG. 28 for a competitive assay reaction, a distribution of signal substance generators is formed in a flow of a liquid sample by use of specific binding reactions in accordance with the concentration of substance to be assayed, and the aforementioned signal detection is conducted by two detection means 6 and 7 located at different positions along the flow direction in the channel b. At this occasion, though the detection means are measuring the signal depending on the distribution of signal substance generators formed corresponding to the concentration of specific substances to be assayed, different signal intensities are measured due to difference in the distribution of distances between the signal substance generators and detection means coming from relative positions different to the distribution of the signal substance generator. Namely, signal intensities of two detection means show different response curves with regard to the concentration of the substance to be assayed in the liquid sample. Respective response curve can be approximated by a mathematical function having some of coefficients. When the responses of two detection means are expressed in a linear function, for example, the relation between the signal intensity I and concentration C of substance to be assayed is expressed by $I=a \cdot C+b$, in which coefficients a and b may differ in the respective electrodes.

As exemplified by FIG. 27, since the signal detecting system for the two detection means is the same, the signals at two detection means are affected identically by the non-specific measuring error factor Z in the liquid sample. The effect of the measuring error factors on signal intensities can be classified into an additive influence and a proportional influence as mentioned in FIG. 29, however, both influences exist in both signals as a mixture. Therefore, the calibration widely used in this field for calibrating additive influence by subtracting control or reference value from the measured value, which is called as the blank calibration method, is not enough to give a result of accuracy. In conventional blank calibration methods, since detection means for the control or reference must be settled at equivalent positions of those for the measuring, and further must be so arranged as to indicate no response to the concentration of the substance to be assayed, the method is restrictive and the mechanism of assay device is complicated. In the present assay method, because of the presence of the flow in which the distribution of signal substance generator is formed in accordance with the concentration of substance to be assayed, the detection means settled at any position of the flow direction respond to the concentration of the substance to be assayed (signal from specific binding reaction of the test sample) even though the response degree is very small in some cases. Then, the detection means of the invention does not respond independently to the noise signal (error factors from non-specific influence of the test sample) but respond both the signal and the noise signal. In spite of the responses including the signal and the noise signal at each of the plural detection means of the invention, present method can provide a precise calibration method. Further, in the present assay method, it is possible to minimize the effect of the non-specific measuring error factor Z containing simultaneously additive and proportional influences from consideration of its affecting evenly on a plurality of detection means.

In other words, according to the present assay method, it is possible to derive a relation formula for obtaining the concentration of substance to be assayed under minimized effects of measuring error factors, based on the response relationship between signal intensities in a plural detection means and concentration of substance to be assayed as well as on the relationship between signal intensities in a plurality of detection means and the non-specific measuring error factor Z. Several methods are available for the derivation, and the undermentioned ones are preferred due to the simplicity and high precision.

Method-1 Usage of a parameter minimizing effects of non-specific measuring error factor Z:

In the method, forecast a measuring error factor foreseeable for the objective assay, elect a parameter (the function of signal intensities at plural detection means) and a formula thereof to minimize the effect of the error factor, and optimize the parameter by conducting assay in the presence of the measuring error factors foreseeable. Generally, the additive influence can be eliminated through differences between signal intensities of a plurality of detection means, and the proportional influence is eliminated through calculating ratios, and the parameters P, G and R shown afterward are exemplified accordingly. Any formula is usable if the parameter enables to minimize the effect of measuring error factors.

Method-2 Estimating an approximate equation for response curve, and using the formula relating the measuring error factors as the coefficients of the equation:

In the method, the effect of the measuring error factor Z on coefficients of an approximate equation for concentrations of substance to be assayed in a plurality of detection means is approximated by functional relations, and a final formula for obtaining concentrations of substance to be assayed is derived from the approximate equation and the functional relations. In the method, the effect of the measuring error factor Z on coefficients of an approximate equation may be expressed as a functional relation more precisely by conducting assays under conditions of foreseeable measuring error factor Z to enable more accurate assay.

In consequence, the present invention has rendered possible provision of a simple and easy specific binding assay method and a specific binding assay device suitable for the practice of the assay method, which does not require a separation step (washing step) of unreacted substances, is excellent in general purpose performance and can be used for quick measurement and also can minimize measurement errors caused by the non-specific influence of the specific binding assay without requiring additional assay handling.

The method for the determination of a substance to be assayed in a liquid sample based on signals of a plurality of detection means is described in the following further in detail.

The function f of the aforementioned formula (1) is defined by the substance to be assayed, specific binding substance, signal substance generator, signal substance, type of the specific binding reaction, type of the signal substance generation, arrangement of detection means, assay device constitution and the like. However, since the function f varies depending on these factors, it is difficult in general to make the function itself into a mathematical formula.

As a method to obtain the aforementioned relation formula (3) to determine the concentration C of a substance to be assayed, a plurality of samples having the same amount of a substance to be assayed but with varied Z are selected and assayed, a relational formula between signal strengths $I_1$ and $I_2$ with the same amount C of the substance to be assayed is estimated and then relationship between the relational formula and the concentration C of the substance to be assayed is estimated. This method will be described later in inventive Example 2 in detail.

This method, however, requires many preliminary examinations to obtain the relation formula.

In a more simple method, an parameter which can minimize influence of Z is introduced on an assumption that the formula (3) is materialized.

The parameter can be used as a function of $I_1$ and $I_2$ and is determined by various factors such as substance to be assayed, specific binding substance, signal substance generator, signal substance, type of the specific binding reaction, type of the signal substance generation, arrangement of detection means, assay device constitution and the like.

parameter $P=u(I_1, I_2)$

In consequence, the amount C of the substance to be assayed becomes a function of the parameter P, which therefore is used as an relation formula.

$C=v(P)$

The parameter can be applied to any functional formula, provided that it is a functional formula of $I_1$ and $I_2$ which can minimize influence of Z. In general, the following formula parameter $P=I_1-a\cdot I_2$ or parameter $Q=(I_1-a)/(I_2-b)$ is preferred in which a and b are constants.

As will be illustrated later in Inventive Example 3, each of these parameters P and Q can minimize the influence of Z when heparinized plasma is used as a test sample. Also, Inventive Examples 3, 4 and 5 illustratively show that this method is useful when Z is any one of the non-specific influence of contaminant in a test sample, the reaction temperature and the change in the activity of a signal substance generator.

In Inventive Example 6, usefulness of this method in the case of a whole blood sample was illustrated using the internal parameter Q. In each of these inventive Examples, a sandwich type specific binding reaction was employed using hCG as the substance to be assayed.

The function of parameters is not limited to the case of P and Q, and a combined function of P and Q can also minimize the influence of Z. For example, parameter $R = \dfrac{aI_1 - cI_2 + e}{bI_1 - dI_2 + f}$ wherein each of a, b, c, d, e and f is a constant, can be illustrated, and any function capable of reducing the influence of Z can be used as a parameter. There are many other useful arithmetic processing methods which can minimize influence of other factors than the concentration of a substance to be assayed upon assay results, using a plurality of detection results detected at a plurality of detection means arranged at different positions in the flow direction of a liquid sample. Since these arithmetic processing methods are different from one another in terms of the degree of minimization, a function most effective for the minimization may be used as the parameter. For example, degree of the minimization of influence of various factors, excluding concentration of a substance to be assayed, upon assay results can be improved by introducing a function which is more accurate than the aforementioned parameter R and the relation formula derived from R, like the case of a relation formula S which will be described later.

Concerning the signal intensities $I_1$ and $I_2$, current values at the detection means may be used, similar processing can also be made making use of current densities (current value/electrode area), instead of the current values, as shown in Inventive Examples 3, 4, 5, 6, 7 and 8.

It is particularly desirable that the thus obtained parameter and/or relation formula is incorporated in advance into the arithmetic processing mechanism of a measuring apparatus, or input it as a parameter in the measuring apparatus at the time of measurement and the amount of a substance to be assayed is processed and displayed after the measurement.

In order to correct difference between lots of the assay device, it is desirable to input assay device-specific constants in the parameter function incorporated in advance into the arithmetic processing mechanism of a measuring apparatus. That is, when a part or all of the constant portions of the aforementioned parameter function (for example, a, b, c, d, e and f in the case of the parameter R) are dependent upon each lot of the assay device, lot difference of the assay device can be corrected by setting these constant portions in the measuring apparatus prior to the commencement of the assay. Setting of these constant portions in the measuring apparatus can be effected by generally used input means which include for example setting using a hardware switch such as a ring switch, a dip switch or the like, input using an input apparatus such as a keyboard, a mouse, a pen or the like, reading of magnetic information using a magnetic tape, a magnetic card or the like, reading of electric information such as electric property value, IC memory or the like of a sensor portion and optical reading using a bar code or the like.

Next, a method for the determination of assay device lot-specific constant portions of a parameter function is described with reference to the competitive reaction assay of Inventive Example 7 in which estradiol in a whole blood sample is used as a substance to be assayed. In Inventive Example 7, Z is minimized using an parameter function S which is obtained by a logistic curve-based analysis carried out to minimize influence of Z in a whole blood sample. Also in Inventive Example 8, assay device lot-dependent constants contained in the relation formula are determined from a serum sample prepared for determining the lot-dependent constants. Since whole blood samples cannot be preserved stably for a prolonged period of time, this device lot-dependent constant determination method by the use of a serum sample for determining the lot-dependent constants can be standardized easily and handled simply, in comparison with a constant determination method in which a whole blood sample is used for determining the lot-dependent constants, and therefore is suitable for the device lot management at the time of the assay device production.

In Inventive Example 7, a hapten, namely estradiol, is used as the substance to be assayed and a competitive method is used as the specific binding reaction, so that a signal intensity $I_1$ at the first detection means against the concentration C of the substance to be assayed in a test sample fits to an S-shaped curve such as a logistic curve (formula 4).

$$I_1 = \dfrac{a1 - d1}{1+(C/c1)^{b1}} + d1 \qquad \text{formula 4}$$

Based on the measured results of test samples prepared by adding estradiol to various whole blood samples using the assay device of inventive Example 7, the present inventors have found that the influence of Z causes fluctuation of two coefficients a1 and d1, but does not cause large fluctuation of the other two coefficients b1 and c1. That is, b1 and c1 in the formula (4) are constants, but a1 and d1 are functions of Z which vary depending on each whole blood sample. In the assay device illustrated in Inventive Example 7, a signal intensity $I_2$ at the second detection means against the concentration C of the substance to be assayed in a test sample also fits to a logistic curve (formula 5).

$$I_2 = \frac{a2 - d2}{1 + (C/c2)^{b2}} + d2 \qquad \text{formula (5)}$$

In the assay device of Inventive Example 7, similar to the case of the first detection means, b2 and c2 in the formula (5) are constants, but a2 and d2 are functions of Z which vary depending on each whole blood sample. The present inventors have found also that approximation can be made as b1=b2=b (constant) and c1=c2=c (constant) in the assay device of inventive Example 7. Modification of the formulae (4) and (5) results in the following formulae (6) and (7).

$$C = c \times \text{Exp}\left( \frac{\ln\left(\frac{a1 - I_1}{I_1 - d1}\right)}{b} \right) \qquad \text{formula (6)}$$

$$C = c \times \text{Exp}\left( \frac{\ln\left(\frac{a2 - I_2}{I_2 - d2}\right)}{b} \right) \qquad \text{formula (7)}$$

Based on the measured results of various whole blood samples using the assay device of Inventive Example 7, the present inventors have also found the presence of a functional relationship between a1 and d1 which can be expressed as $d1=f_1(a1)$, a functional relationship between a2 and d2 which can be expressed as $d2=f_2(a2)$ and a functional relationship between a1 and a2 which can be expressed as $a2=g(a1)$. When these functional relation formulae are used, a function of $a1=h(I_1, I_2)$ can be obtained by eliminating a2, d1 and d2 from the formulae (6) and (7). As is evident from the aforementioned functional relationships, this means that all of the sample-dependent coefficients a1, d1, a2 and d2 can be obtained from $I_1$ and $I_2$. In consequence, a relation formula $C=S(I_1, I_2)$, by which C can be obtained from $I_1$ and $I_2$, can be derived by eliminating the sample-dependent coefficients a1, d1, a2 and d2 from the formula (6) or (7). The thus obtained relation formula $C=S(I_1, I_2)$ in a formula that has minimized non-specific influences in various whole blood samples. When the signal intensities $I_1$ and $I_2$ fit respectively S-shaped curve such as logistic curve, and at least b1=b2 and c1=c2, the sum of the signal intensities $(I_1+I_2)$ or the difference of the signal intensities $(I_1-I_2)$ also may fit S-shaped curve such as logistic curve. Therefore, when one of the $I_1$ and $I_2$ is replaced with $(I_1+I_2)$ or $(I_1-I_2)$ in the formulae (4), (5), (6) and (7), the relation formula C described above can also be derived in the same procedure. In Inventive Example 7, the relation formula is obtained by using $I_1$ and $I_1+I_2$.

In addition, the present inventors show in Inventive Example 8 that assay device lot-dependent constants contained in this relation formula for whole blood samples can be determined from serum samples for the testing instead of whole blood samples. This can be achieved in the following manner.

That is, the aforementioned dependency of coefficients a1, d1, a2 and d2 on whole blood samples means that a1, d1, a2 and d2 are changed by Z such as aforementioned contaminants in the sample, sample properties, assay environment, changes in sample component activities and the like. In this connection, the coefficients a1, d1, a2 and d2 respectively correspond to the positions of the lower and upper asymptotic lines of the S-shaped response curve of the first detection means and the lower and upper asymptotic lines of the S-shaped response curve of the second detection means. In other words, a1 can be regarded as a signal strength of the first detection means when concentration of a substance to be assayed in a test sample is sufficiently low, d1 can be regarded as a signal strength of the first detection means when concentration of a substance to be assayed is sufficiently high, a2 as a signal strength of the second detection means when concentration of a substance to be assayed is sufficiently low and d2 as a signal strength of the second detection means when concentration of a substance to be assayed is sufficiently high. In consequence, the presence of the aforementioned functional relationships among these coefficients, such as $d1=f1(a1)$, $d2=f2(a2)$ and $a2=g(a1)$, means that these positions of the asymptotic lines fluctuate having a regularity against Z. In general, these functional relationships can be explained as follows. The functional relationship $d1=f1(a1)$ indicates the presence of a tendency that the upper asymptotic line of the S-shaped response curve of the first detection means becomes high in the case of a whole blood sample in which the lower asymptotic line of the S-shaped response curve of the first detection means becomes high. The functional relationship $d2=f2(a2)$ indicates the presence of a tendency that the upper asymptotic line of the S-shaped response curve of the second detection means becomes high in the case of a whole blood sample in which the lower asymptotic line of the S-shaped response curve of the second detection means becomes high. Also, the functional relationship $a2=g(a1)$ indicates the presence of a tendency that the lower asymptotic line of the S-shaped response curve of the second detection means becomes high in the case of a whole blood sample in which the lower asymptotic line of the S-shaped response curve of the first detection means becomes high.

As described in the foregoing, these functional relationships can be found out when a plurality of whole blood samples are used, and a relation formula can be obtained from these relationships. Measurement of a plurality of whole blood samples means simply that a functional relationship which reflects the appearance of the influence of Z with a certain regularity in each coefficient is determined by measuring a plurality of test samples having different Z values. In other words, testing samples to be used in the derivation of such relation formula specific for the assay device lot are not limited to whole blood samples, and other samples having different Z values whose similarity to the behavior of whole blood samples are already known can also be used.

Such samples for testing use can be obtained for example by adding Z elements to standard serum or standard plasma samples. Examples of the Z elements to be added include contaminants, activities analogous to those of signal substance generators, factors which change sample properties and substances which inhibit signal substance generators or signal substances. Illustrative examples of preferred Z elements include enzymes such as peroxidase, catalase and the like, blood pigment components or hemolytic components such as hemoglobin and the like, oxidation-reduction compounds such as ascorbic acid, uric acid and the like, pH-fluctuating elements such as acidic or basic components, ionic strength-fluctuating elements such as salts and the like, cofactors such as metal ions, coenzymes and the like, enzyme inhibitors and viscous substances such as polysaccharides and the like. Examples of preferred Z elements which can be added to effect fluctuation of hematocrit values include latex particles, fine polymer particles and blood cell analogues such as fixed blood cells and the like, as well as a testing sample to which an electron mediator and/or enzyme-labeled substance is added in order to fluctuate concentration of the electron mediator or enzyme-labeled substance which is apt to receive influence of hematocrit values. In addition, the Z elements are not necessarily such added substances, and the testing may be carried out by changing the reaction temperature as an assay environment-fluctuating factor or after changing activities of reagent components contained in the assay device by treating them under a high temperature or high moisture condition. The testing means are not particularly limited to these examples, and any other means can be used provided that the relation formula can be determined thereby.

The description in Inventive Example 7 or in the above is based on a case in which the signal strength of the second detection means also responds depending on the concentration of a substance to be assayed. Since the first and second detection means are arranged at different positions in the liquid flow direction, responses of signal strengths of respective detection means to the concentration of a substance to be assayed do not become the same, so that the internal parameter relational formula can be derived. The first and second detection means can be arranged in such a manner that responses of signal strengths of respective detection means to the concentration of a substance to be assayed become completely different from each other. An example of such an arrangement is a case in which, in the electrode portion 60 shown in FIGS. 4A and 4B, position of the first detection means 76 is not changed but the inner and outer diameters of the second detection means 78 are positioned far enough from the sealing means 64a in the assay device of FIG. 2, and the resulting second detection means is arranged at the outside area of the sealing means 64a. In that case, signal strength of the second detection means does not depend substantially on the concentration of a substance to be assayed, but may be estimated to be dependent solely upon Z, and the current response $I_2$ of the second detection means against the concentration C of the substance to be assayed in a test sample fits to the following formula (8) instead of the aforementioned formula (5).

$$I_2 = d_2 \quad \text{formula (8)}$$

In this case, the parameter function $C=S(I_1, I_2)$ can also be derived from the response formula (4) or (6) of the first detection means, the formula (8) of the second detection means and the functional relation formulae $d1=f_1(a1)$ and $a2=g(a1)$. That is, when a plurality of detection means are arranged at different positions in the liquid flow direction and signal response of at least one of the detection means is dependent on the concentration of a substance to be assayed in a test sample, arithmetic processing can be made in such a manner that the influence of elements, excluding concentration of the substance to be assayed, on the detection results can be minimized. In consequence, the arrangement of a plurality of detection means at different positions in the liquid flow direction and the form of the assay device are not limited to the description in the following examples or the aforementioned illustrations.

EXAMPLES

The following examples are provided to further illustrate the present invention. It is to be understood, however, that the examples are for purpose of illustration only and are not intended as a definition of the limits of the invention.

[Preparation of electrode portion]

Various types of the electrode portion 60 shown in FIGS. 4A and 4B were prepared by subjecting the front and back sides of a transparent PET film having a thickness of 0.25 mm to screen printing using a conductive carbon ink (400-CT, manufactured by Asahi Kaken), a conductive silver paste (LS411N, manufactured by Asahi Kaken) and a resist (XB101G, manufactured by Fujikura Kasei).

Firstly, the front side of the PET film to be used as the insulating base 61 was subjected to screen printing using the carbon ink to form the counter electrode (reference electrode) 70 and the terminal 70a, followed by the formation of the insulating layer 74 using the insulating resist. The counter electrode 70 was further subjected to finish coat printing using the silver paste.

Next, on the back side of the PET film to be used as the insulating substrate 61 were formed the first working electrode 76, its terminal 76a, the second working electrode 78 and its terminal 78a in the same manner using the carbon ink, followed by the formation of the insulating layer 74 (that is, silver paste printing was not applied).

After formation of respective electrodes and insulating layers, the PET film was cut into a size of 50 mm in length and 20 mm in width, and the through hole 68 was formed by punching the central portion of the counter electrode 70 and the first working electrode 76. In this way, a total of 7 types of the electrode portion 60 shown in FIGS. 4A and 4B were prepared, each having different sizes of the first working electrode 76, the second working electrode 78, the through hole 68 and the like.

Data of each working electrode on the back side of the electrode portion 60 are shown in the following. In this case, data of counter (reference) electrodes from electrode portions 60a to 60f are omitted, because they are formed on the front side of the electrode portion 60 at the same position of the first working electrode 76, having completely the same size and shape. Since the counter electrode (reference electrode) of the electrode portion 60g has a different size, data of this counter (reference) electrode on the front side of the electrode portion 60 are also shown together with data of its working electrode on the back side.

<Electrode portion 60a>

Through hole 68 (inner diameter of the first working electrode 76), 3 mm; outer diameter of the first working electrode 76, 5 mm (that is, the first working electrode 76 has a width of 1 mm); gap between the first working electrode 76 and the second working electrode 78, 0.5 mm; and outer diameter of the second working electrode 78, 8 mm (that is, the second working electrode 78 has a width of 1 mm)

<Electrode portion 60b>

Through hole 68 (inner diameter of the first working electrode 76), 3 mm; outer diameter of the first working electrode 76, 6 mm (that is, the first working electrode 76 has a width of 1.5 mm); gap between the first working electrode 76 and the second working electrode 78, 1 mm; and outer diameter of the second working electrode 78, 11 mm (that is, the second working electrode 78 has a width of 1.5 mm)

<Electrode portion 60c>

Through hole 68 (inner diameter of the first working electrode 76), 3 mm; outer diameter of the first working electrode 76, 6 mm (that is, the first working electrode 76 has a width of 1.5 mm); gap between the first working electrode 76 and the second working electrode 78, 1.5 mm; and outer diameter of the second working electrode 78, 12 mm (that is, the second working electrode 78 has a width of 1.5 mm)

<Electrode portion 60d>

Through hole 68 (inner diameter of the first working electrode 76), 3 mm; outer diameter of the first working electrode 76, 5 mm (that is, the first working electrode 76 has a width of 1 mm); gap between the first working electrode 76 and the second working electrode 78, 2 mm; and outer diameter of the second working electrode 78, 11 mm (that is, the second working electrode 78 has a width of 1 mm)

<Electrode portion 60e>

Through hole 68 (inner diameter of the first working electrode 76), 2 mm; outer diameter of the first working electrode 76, 5 mm (that is, the first working electrode 76 has a width of 1.5 mm); gap between the first working electrode 76 and the second working electrode 78, 1 mm; and outer diameter of the second working electrode 78, 10 mm (that is, the second working electrode 78 has a width of 1.5 mm)

<Electrode portion 60f>

Through hole 68 (inner diameter of the first working electrode 76), 2 mm; outer diameter of the first working electrode 76, 5 mm (that is, the first working electrode 76 has a width of 1.5 mm); gap between the first working electrode 76 and the second working electrode 78, 1.5 mm; and outer diameter of the second working electrode 78, 11 mm (that is, the second working electrode 78 has a width of 1.5 mm)

<Electrode portion 60g>

Through hole 68 (inner diameter of the first working electrode 76), 2 mm; outer diameter of the first working electrode 76, 4 mm (that is, the first working electrode 76 has a width of 1 mm); gap between the first working electrode 76 and the second working electrode 78, 0.5 mm; outer diameter of the second working electrode 78, 6 mm (that is, the second working electrode 78 has a width of 0.5 mm); inner diameter of the counter electrode (reference electrode) on the front side, 2.5 mm; and outer diameter of the counter electrode (reference electrode), 6 mm It was confirmed in each of the thus prepared electrode portion 60 that the first working electrode 76, the second working electrode 78 and the counter electrode 70 are electrically independent from one another and their corresponding terminals 76a, 78a and 70a are electrically connected.

With regard to the counter electrode 70, the aforementioned silver paste electrode was used as such or after forming a silver chloride layer on the surface by carrying out 10 minutes of electrolysis in 0.1M sodium chloride aqueous solution (+1.0 V vs silver/silver chloride electrode).

[Inventive Example 1]

Current responses at a plurality of detection means in an hCG specific binding assay device <1> Preparation of a conjugate body (labeled antibody) of anti-hCGβ antibody and horseradish peroxidase Mouse monoclonal antibody HM81 (prepared by Mochida Pharmaceutical) which recognizes the β chain of hCG was dissolved in a buffer solution consisting of 100 mM sodium chloride, 1 mM EDTA and 60 mM triethanolamine (pH 8.0, to be referred to as "TEA buffer" hereinafter) to a final concentration of 7.7 mg/ml, and the resulting solution was dialyzed thoroughly against the TEA buffer which has been purged with nitrogen. A 143 μl portion of 50 mM 2-iminothiolane hydrochloride (manufactured by Pierce Chemical Company) solution in TEA buffer was added to 2.8 ml of the thus prepared antibody solution, and the mixture was stirred and then allowed to stand still for 1.5 hours at 4° C. in an atmosphere of nitrogen gas. Thereafter, the resulting solution was dialyzed against a buffer solution consisting of 100 mM sodium chloride, 1 mM EDTA and 100 mM phosphate (pH 6.0, to be referred to as "EDTA-PB" hereinafter) which has been purged with nitrogen. In this way, SH group-introduced anti-hCGβ antibody HE81 was obtained.

A 500 μl portion of horseradish peroxidase (to be referred to as "HRPO" hereinafter, manufactured by Toyobo) solution prepared by dissolving it in EDTA-PB to a concentration of 20 mg/ml was gently stirred and mixed with 500 μl of 50 mM sulfo-SMCC (manufactured by Pierce Chemical Company) in 100 mM phosphate buffer (pH 7.0). After 20 minutes of reaction at 30° C., the resulting reaction mixture was passed through a Sephadex G-25 (manufactured by Pharmacia) column (2.6φ×15 cm) which has been equilibrated in advance with nitrogen gas-purged EDTA-PB, thereby removing unreacted sulfo-SMCC, and then concentrated using CENTRIPREP-10 (manufactured by Amicon) to obtain maleimidated HRPO.

$3.66 \times 10^{-7}$ mole of the maleimidated HRPO solution was mixed with a 1/5 molar ratio of the SH group-introduced antibody HM81 solution, and the mixture was incubated at 4° C. for 12 hours in an atmosphere of nitrogen gas. After the reaction, 129 μl of 500 mM cysteamine solution in EDTA-PB was added to the reaction mixture, and the reaction was continued at 4° C. for 60 minutes in an atmosphere of nitrogen gas. Thereafter, the resulting reaction mixture was subjected to a gel filtration chromatography using ULTROGEL AcA34 (manufactured by IBF Biotechnics) column which has been equilibrated in advance with nitrogen gas-purged EDTA-PB.

Each of the thus eluted fractions were checked for its absorbaces at 280 nm and 403 nm, in order to collect and concentrate fractions containing the HM81/HRPO linked product but not containing free enzyme molecules. The thus concentrated conjugate preparation (to be referred to as "HRPO-HM81" hereinafter) was checked for its molecular weight by a Phast system electrophoresis (manufactured by Pharmacia) and its antibody and enzyme contents based on its absorbance and enzyme activity and used as a signal substance generator in measuring experiments.

<2> Preparation of a first impregnation portion 54 (signal substance generator-impregnated portion, namely a dried body impregnated with a horseradish peroxidase-labeled anti-hCGβ antibody)

A solution was prepared by diluting the horseradish peroxidase-labeled anti-hCGβ antibody prepared in the above step <1> with 0.1M phosphate buffer (pH 6.0) containing 0.1M NaCl further supplemented with 0.01% Amisoft LS-11 (manufactured by Ajinomoto), 5% normal rabbit serum (NRS) and 10% saccharose. Next, a 140 μl portion of the thus prepared solution was spotted on a circular filter paper of 12 mm in diameter obtained by punching a glass fiber filter paper (GA100, manufactured by Advantech Toyo), and the resulting filter paper was freeze-dried to obtain the first impregnation portion 54 (signal substance generator-impregnated portion).

<3> Preparation of a second impregnation portion 56 (electron mediator-impregnated portion, namely a dried body impregnated with N,N,N',N'-tetrakis-(2'-hydroxyethyl)-p-phenylenediamine dihydrochloride (to be referred to as "THEPD" hereinafter))

A 5.0 mM THEPD solution was prepared by dissolving it in 0.1M phosphate buffer (pH 6.0) containing 0.01% Tween 20 and 0.1M NaCl. Next, a 140 μl portion of the thus prepared solution was spotted on a circular filter paper of 12 mm in diameter obtained by punching a glass fiber filter paper (GA100, manufactured by Advantech Toyo), and the resulting filter paper was freeze-dried to obtain the second impregnation portion 56 (electron mediator-impregnated portion).

<4> Preparation of absorption means 64 (a dried body impregnated with hydrogen peroxide and urea)

Hydrogen peroxide and urea (both manufactured by Wako Pure Chemical Industries) were dissolved in distilled water to prepare a 3.0M hydrogen peroxide-3.0M urea solution. Next, a 120 μl portion of the thus prepared solution was spotted on a circular filter paper of 12 mm in diameter obtained by punching a chromatograph filter paper (17 Chr, manufactured by Whatman), and the resulting filter paper was freeze-dried to obtain the absorption means 64 (dried body impregnated with hydrogen peroxide and urea).

This absorption means, therefore, serves also as a holding portion of an enzyme substrate (hydrogen peroxide) which is a substance related to the generation of a signal substance.

<5> Preparation of channel 62 (an antibody-immobilized membrane, namely an anti-hCGβ antibody-immobilized porous cellulose ester mixture membrane)

A 200 ml portion of 1.0% (w/v) bovine γ-globulin (product code, G7516; manufactured by Sigma) solution in 0.076M phosphate buffer containing 0.45% sodium chloride (to be referred to as "PBS" hereinafter) was put into a beaker. A total of 200 pieces of a cellulose acetate/cellulose nitrate mixture ester porous membrane (catalog No. SCWP01300, manufactured by Nippon Millipore), in a circular form of 13 mm in diameter having a pore size of 8.0 μm, were added to the above solution and heated at 60° C. for 2 hours with gentle stirring.

The supernatant fluid was removed, and the still remaining liquid was removed by suction. The resulting pieces were washed by thoroughly stirring them in a sufficient volume of PBS and then removing the buffer solution. The washing step with PBS was repeated two more times, and the pieces were further washed 7 times with distilled water.

After completion of the washing, the resulting pieces were gently stirred in 200 ml of 1.0% glutaraldehyde aqueous solution to carry out 3 hours of reaction at 25° C. After the reaction, the thus treated porous membrane pieces were washed 10 times with distilled water and then dried by placing them one by one on a glass plate.

Mouse monoclonal antibody HM21 (manufactured by Mochida Pharmaceutical) which recognizes the α chain of hCG was dissolved in a 0.05M sodium bicarbonate-0.05M sodium chloride aqueous solution to a final concentration of 1.0 mg/ml. A 25 μl portion of the thus prepared antibody solution was spotted on the central portion of each of the above porous membrane pieces (13 mm φ) dried on a glass plate. After 1 hour of reaction at room temperature, 200 ml of a 0.2% bovine serum albumin (BSA)/PBS solution was added to the porous membrane to carry out 2 days of blocking reaction at 4° C. with shaking.

Thereafter, the thus treated pieces were washed three times with a 0.1% Tween 20/PBS solution and then 7 times with PBS. By soaking for 30 minutes in 4% mannitol-0.01% Tween 20/PBS at room temperature and drying on a Petri dish under a reduced pressure, the channel 62 (anti-hCGα antibody-immobilized porous cellulose ester mixture membrane) was obtained.

<6> Construction of specific binding assay device

Using the thus prepared respective parts and the previously prepared electrode portions 60a to 60f, various specific binding assay devices shown in FIGS. 2 and 3 were constructed in the following manner.

Firstly, the absorption means 64 (dried body impregnated with hydrogen peroxide and urea) was superposed on the acrylic base cover 66. A seal of 6 mm in diameter obtained by punching a mending tape (manufactured by Sumitomo 3M) was adhered on the center of the absorption means. Next, the channel 62 (anti-hCGα antibody-immobilized porous cellulose ester mixture membrane) was superposed on the water absorption means 64 having the sealing means 64a, by adjusting their centers at the same position.

On this was superposed the electrode portion 60 in such a manner that the center of the through hole 68 coincided with the center of the channel 62 and the working electrode portion became down side. A circular filter paper having a diameter of 2 or 3 mm was prepared by punching from a glass fiber filter paper (GA55, manufactured by Advantech Toyo), inserted into the through hole of the electrode and used as the communication means 58.

Next, the second impregnation portion 56 (electron mediator-impregnated portion) was superposed in such a manner that its center coincided with the center of the through hole of the electrode. On the center of the upper surface of the second impregnation portion 56 was adhered a seal of 6 mm in diameter obtained by punching a mending tape. On this was superposed the first impregnation portion 54 (signal substance generator-impregnated portion). On this was further superposed a circular member of 12 mm in diameter prepared by punching surfactant-treated ELTAS (catalog No. A05070, manufactured by Asahi Chemical Industry) to be used as the filter portion 52.

This was covered with the acrylic upper cover 50 having the sample-introducing hole 50a of 6 mm in diameter in such a manner that the center of the sample-introducing hole 50a coincided with the center of the through hole 68, and then the thus laminated members were fixed by screwing up the four corners of the upper cover 50 and the lower substrate 66. In this way, 6 types of the specific binding assay device shown in FIGS. 2 and 3 for use in the measurement of the concentration of hCG were constructed in which the electrode portions 60a to 60f were respectively used.

<7> Measurement of hCG using each assay device

Using the counter electrode 70 (silver paste circular electrode) as a counter/reference electrode, respective terminals of the first working electrode 76 (detection means 1), the second working electrode 78 (detection means 2) and the counter electrode 70 of each of the specific binding assay devices thus constructed were connected with Potentiostat HA-150 (manufactured by Hokuto Denko). The potentiostat was further connected with XY Recorder and Function Generator HB-104 (manufactured by Hokuto Denko) for use in the setting of electrode potentials, and the recorder was connected to a computer via a GPIB line to carry out measurement and data processing.

Authentic hCG sample was dissolved in a 0.1M phosphate buffer solution (pH 6.0) containing 0.1% bovine serum albumin and 0.1M NaCl, in order to prepare a sample solution containing 0 IU/L or 1,000 IU/L of hCG.

A 250 μl portion of each of the thus prepared sample solutions was introduced into each of the specific binding assay devices through the sample-introducing hole 50a of the upper cover 50. Thereafter, electrical potential of each working electrode was set to −150 mV against the counter/reference electrode, and current values were recorded.

<8> Results

Figure 7:
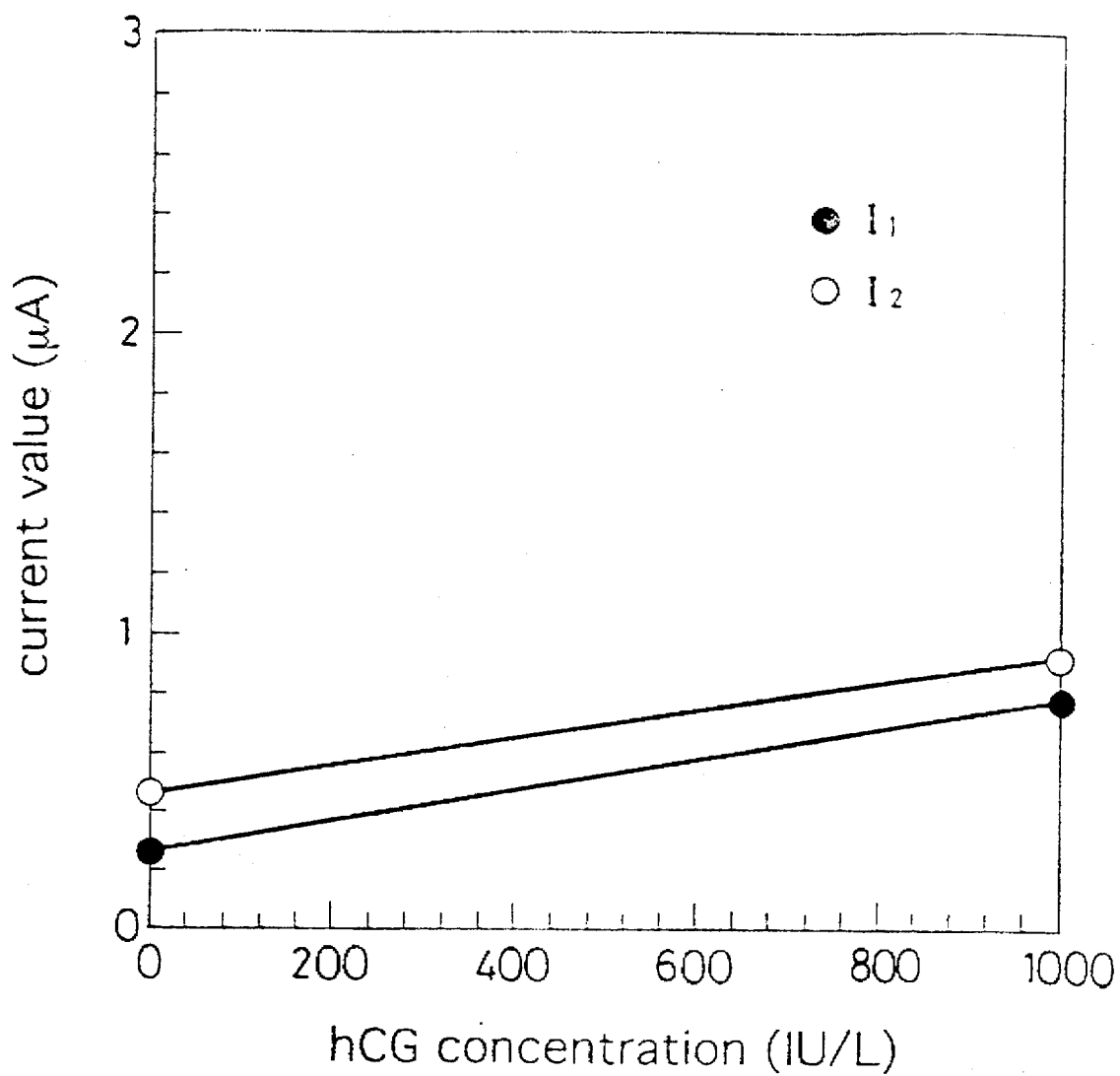
FIG. 7 is a graph showing a relationship between hCG concentrations and current values measured by a plurality of detection means.
Figure 8:
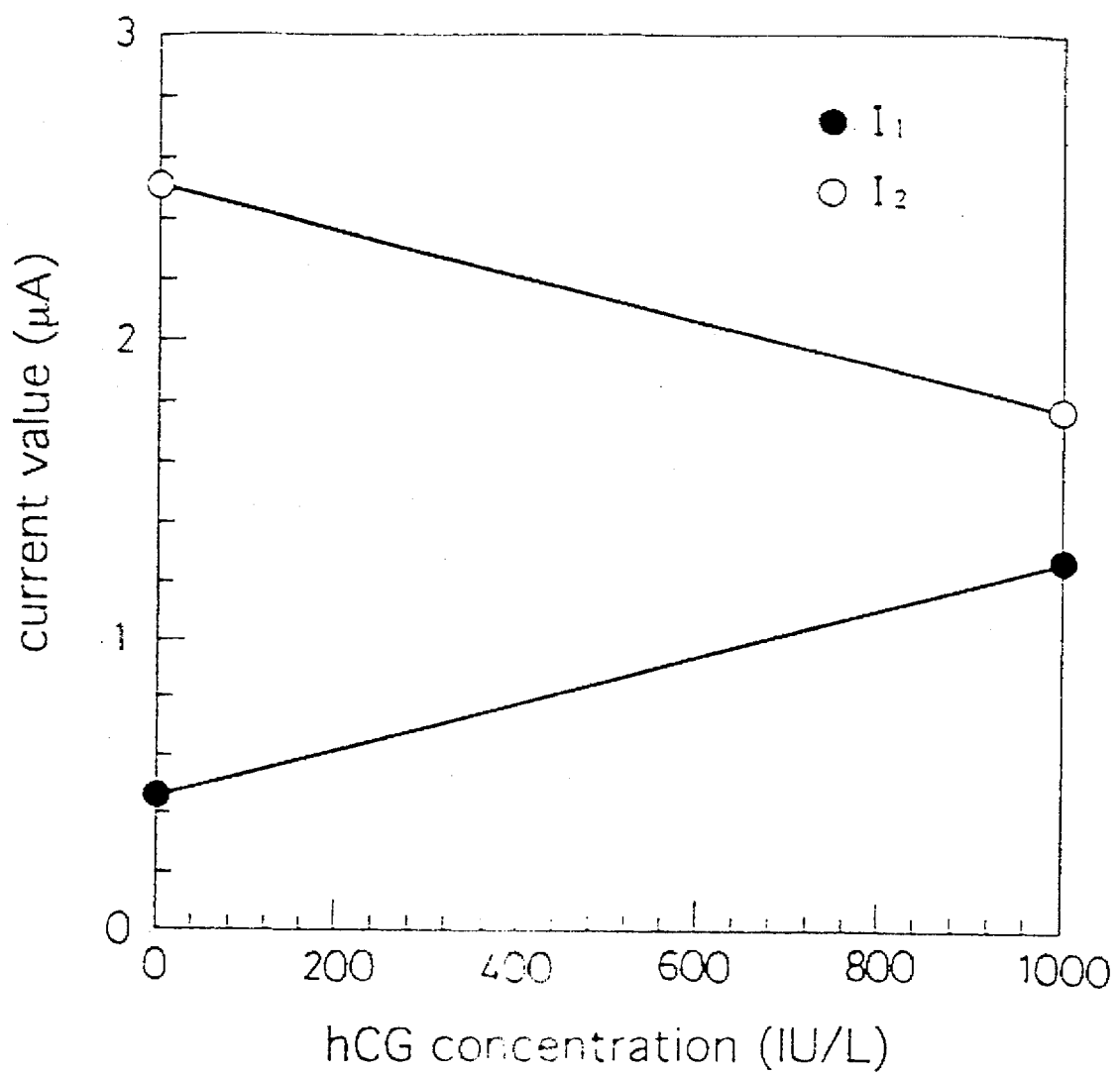
FIG. 8 is a graph showing a relationship between hCG concentrations and current values measured by a plurality of detection means.
Figure 9:
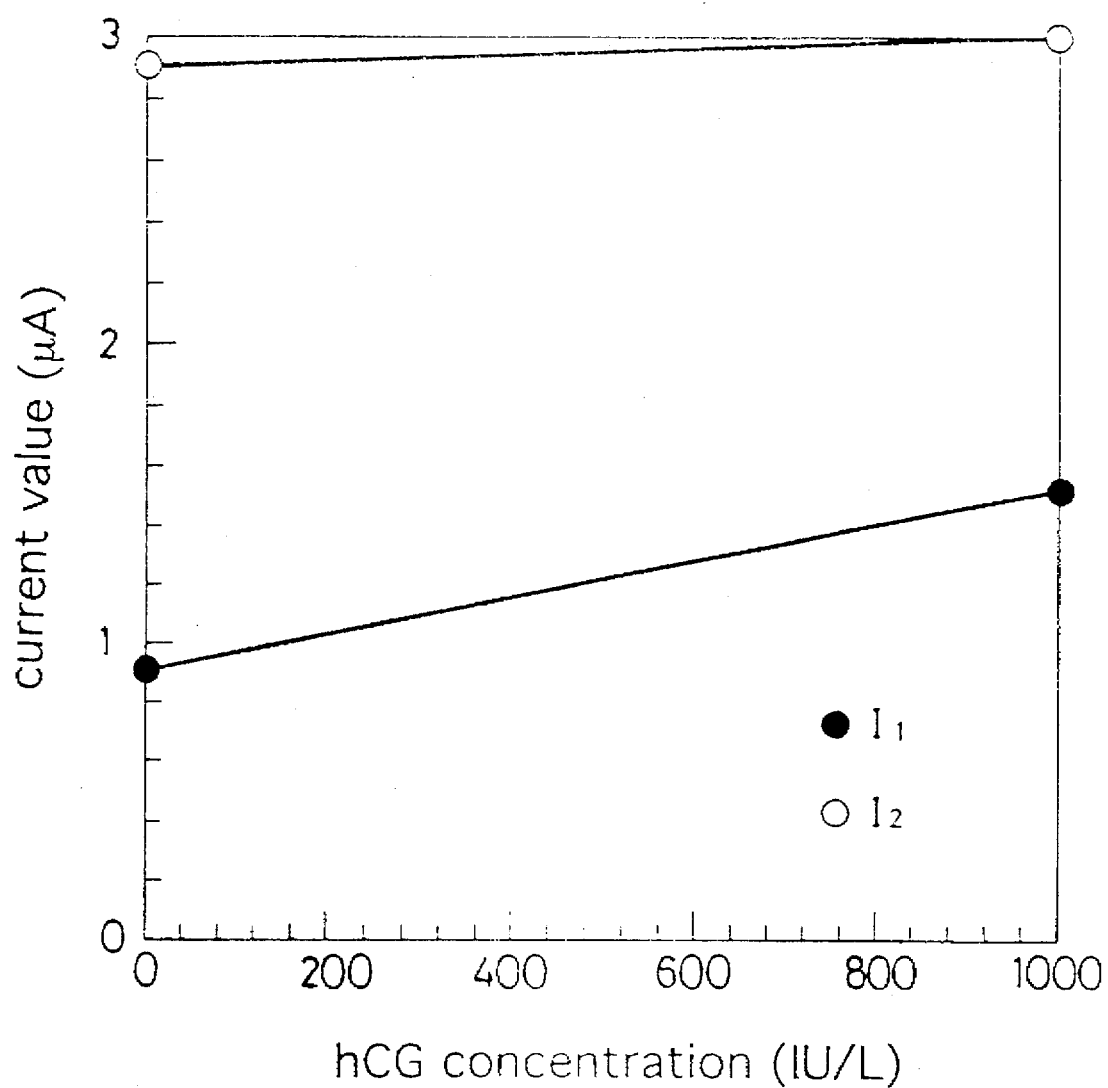
FIG. 9 is a graph showing a relationship between hCG concentrations and current values measured by a plurality of detection means.
Figure 10:
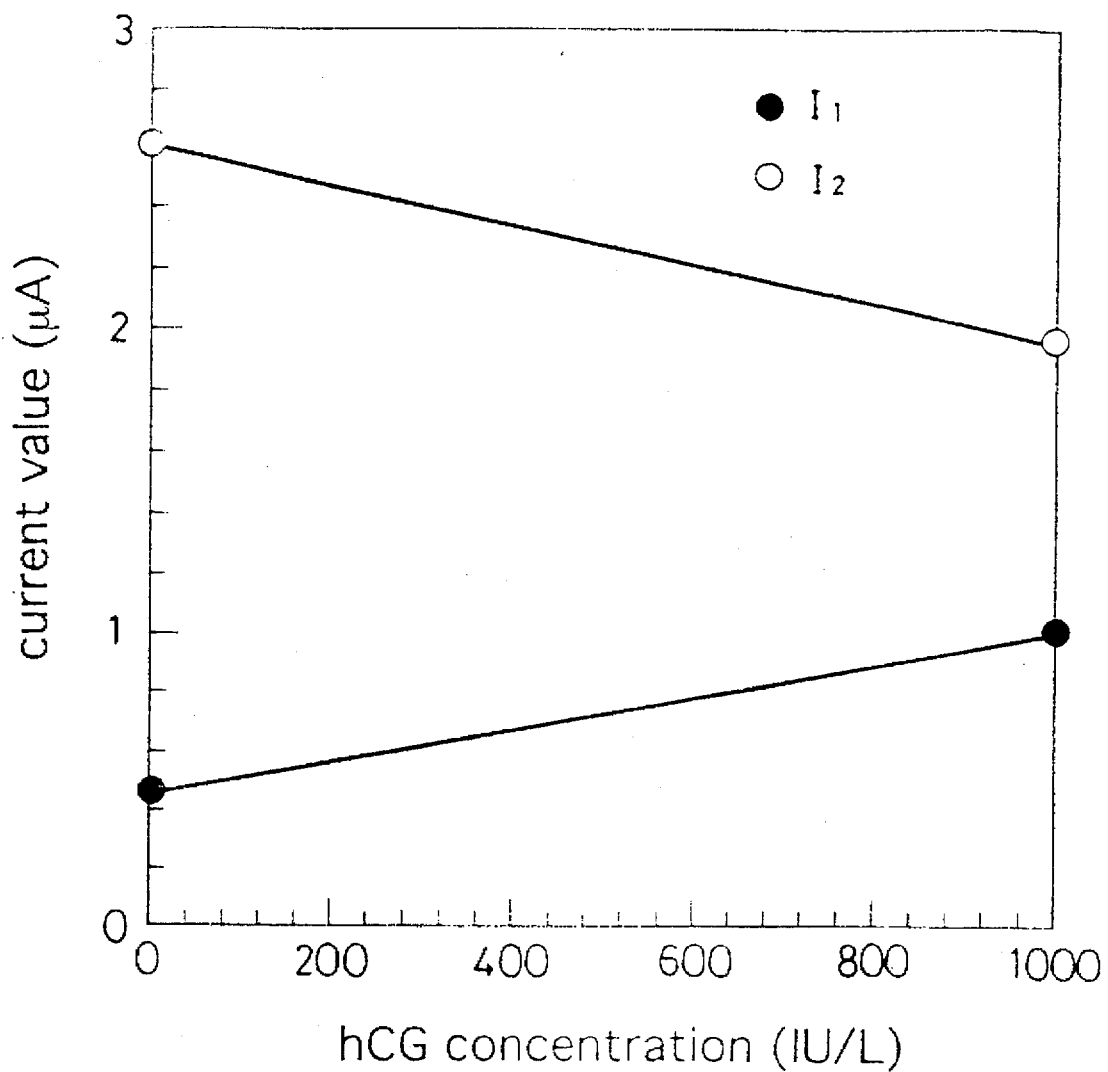
FIG. 10 is a graph showing a relationship between hCG concentrations and current values measured by a plurality of detection means.
Figure 11:
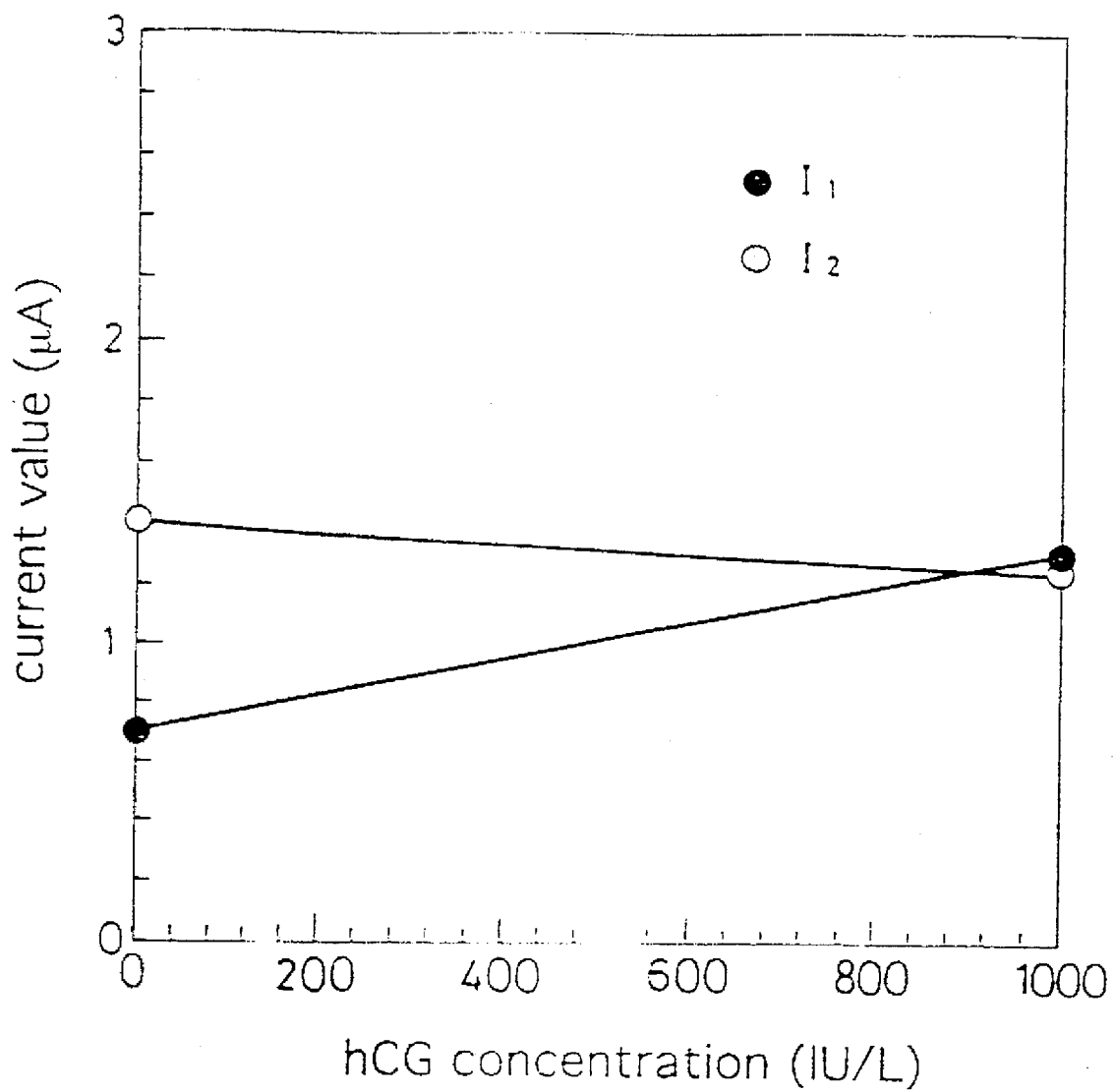
FIG. 11 is a graph showing a relationship between hCG concentrations and current values measured by a plurality of detection means.
Figure 12:
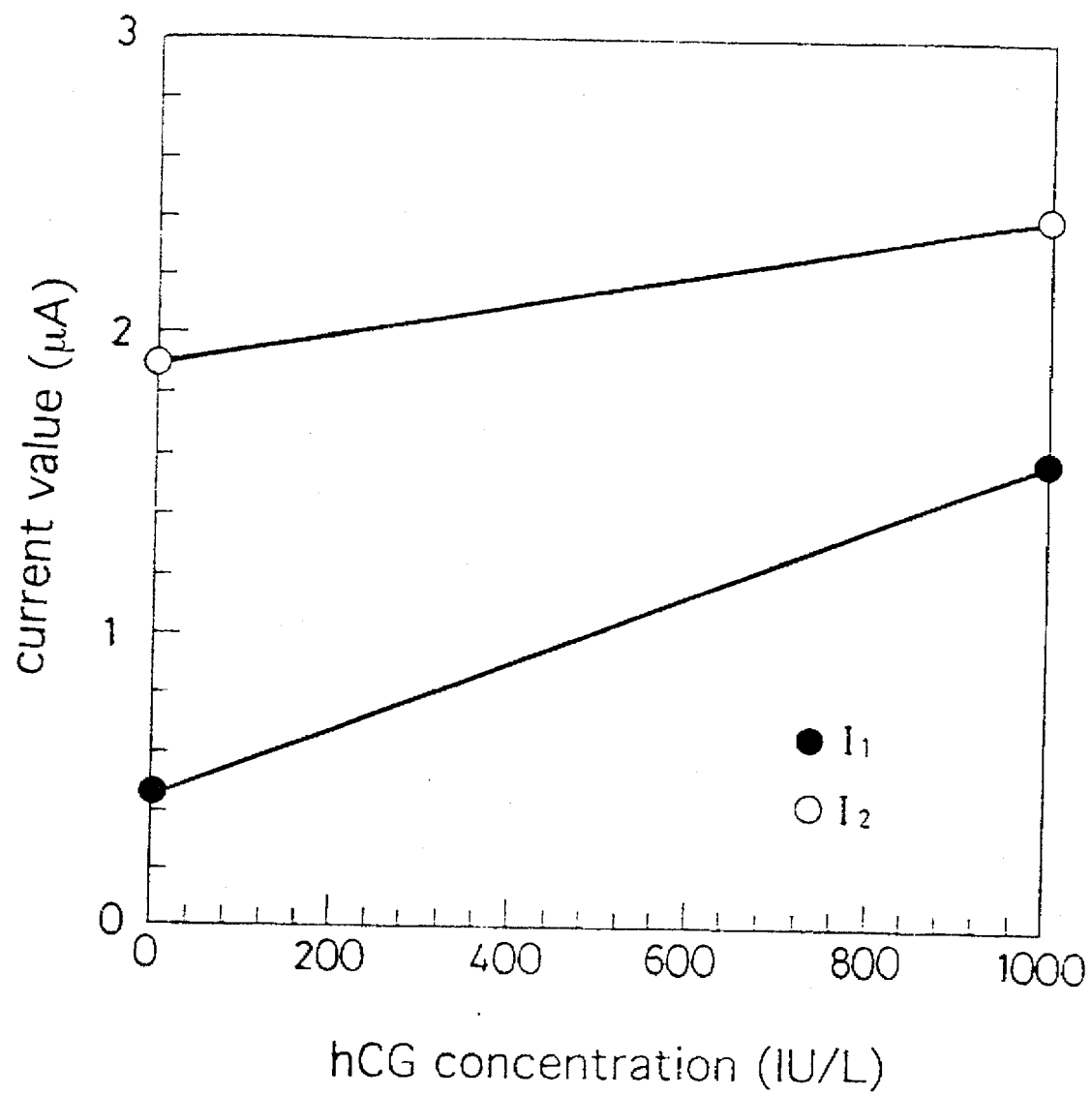
FIG. 12 is a graph showing a relationship between hCG concentrations and current values measured by a plurality of detection means.

Results of the measurement by a specific binding assay device constructed using the electrode portion 60a are shown in FIG. 7, and those using the electrode portion 60b are shown in FIG. 8, 60c in FIG. 9, 60d in FIG. 10, 60e in FIG. 11 and 60f in FIG. 12. All of these data are current values measured 4 minutes after the introduction of respective liquid samples, and the current values measured at the first and second working electrodes 76 and 78 are shown by $I_1$ and $I_2$, respectively.

As is evident from the results shown in FIGS. 7 to 12, the current value changes in response to the concentration of hCG in every device in which the electrode portion 60 having a plurality of working electrodes (detection means) is used, independent of the size of the first working electrode 76 and the second working electrode 78. This means that distribution of the signal substance generator (enzyme-labeled antibody) in the channel changes in response to the concentration of hCG used as a substance to be assayed, and that each detection means can detect changes in the distribution of signal substance generator as the current signal modulation which is rate-limited by diffusion of the signal substance.

[Inventive Example 2]

Measurement of hCG concentration using specific binding assay device.

<1> Preparation of surfactant (Tween 20)-treated glass fiber filter paper

A glass fiber filter paper (GA100, manufactured by Advantech Toyo) was soaked in a 0.2% aqueous solution of Tween 20 (manufactured by Wako Pure Chemical Industries) and allowed to stand overnight at room temperature. Thereafter, the filter paper was washed 10 times with distilled water and then dried in an oven (80° C.) to prepare the surfactant (Tween 20)-treated glass fiber filter paper.

<2> Preparation of a first impregnation portion 54 (signal substance generator-impregnated portion, namely a dried body impregnated with a horseradish peroxidase-labeled anti-hCGβ antibody)

A solution was prepared by diluting the horseradish peroxidase-labeled anti-hCGβ antibody prepared in the step <1> of Inventive Example 1 with 0.1M phosphate buffer (pH 6.0) containing 0.1M NaCl further supplemented with 5% normal rabbit serum (NRS) and 10% saccharose.

A 140 µl portion of the thus prepared solution was spotted on a circular filter paper of 12 mm in diameter obtained by punching the Tween 20-treated glass fiber filter paper prepared in the above step <1>, and the resulting filter paper was freeze-dried to obtain the first impregnation portion 54 (signal substance generator-impregnated portion).

<3> Preparation of a second impregnation portion 56 (electron mediator-impregnated portion, namely a dried body impregnated with N,N,N',N'-tetrakis-(2'-hydroxyethyl)-p-phenylenediamine dihydrochloride (THEPD)

A 5.0 mM THEPD solution was prepared by dissolving it in 0.1M phosphate buffer (pH 6.0) containing 0.1M NaCl.

A 140 µl portion of the thus prepared solution was spotted on a circular filter paper of 12 mm in diameter obtained by punching the Tween 20-treated glass fiber filter paper prepared in the above step <1>, and the resulting filter paper was freeze-dried to obtain the second impregnation portion 56 (electron mediator-impregnated portion).

<4> Preparation of absorption means 64 (a dried body impregnated with hydrogen peroxide and urea)

Hydrogen peroxide and urea (both manufactured by Wako Pure Chemical Industries) were dissolved in distilled water to prepare a 1.0M hydrogen peroxide-1.0M urea solution. Next, a 120 µl portion of the thus prepared solution was spotted on a circular filter paper of 12 mm in diameter obtained by punching a chromatograph filter paper (17 Chr, manufactured by Whatman), and the resulting filter paper was freeze-dried to obtain the absorption means 64 (dried body impregnated with hydrogen peroxide and urea).

<5> Preparation of channel 62 (an antibody-immobilized membrane, namely an anti-hCG antibody-immobilized porous nitrocellulose membrane)

According to the method described Inventive Example 1, <5>, a rabbit polyclonal antibody SE030 (prepared by Mochida Pharmaceutical) which recognizes hCG was immobilized on porous nitrocellulose membrane (manufactured by Advantec Toyo) having a 5 µm diameter pore size to obtain the channel 62.

<6> Construction of specific binding assay device

Using the thus prepared respective parts, various specific binding assay devices shown in FIGS. 2 and 3 were constructed in the following manner.

Firstly, the absorption means 64 (dried body impregnated with hydrogen peroxide and urea) was superposed on the acrylic base cover 66. A seal of 6 mm in diameter obtained by punching a mending tape (manufactured by Sumitomo 3M) was adhered on the center of the absorption means. Next, the channel 62 (anti-hCG antibody (SE030)-immobilized porous nitrocellulose membrane) was superposed on the water absorption filter paper having the sealing means 64a, by adjusting their centers at the same position.

On this was superposed the electrode portion 60a in such a manner that the center of the through hole 68 coincided with the center of the channel 62 and the working electrode portion became down side. A circular filter paper having a diameter of 3 mm was prepared by punching from a glass fiber filter paper (GA55, manufactured by Advantech Toyo), inserted into the through hole of the electrode and used as the communication means 58.

Next, the second impregnation portion 55 (electron mediator-impregnated portion) was superposed in such a manner that its center coincided with the center of the through hole of the electrode. On the center of the upper surface of the second impregnation portion 56 was adhered a seal of 6 mm in diameter obtained by punching a mending tape. On this was superposed the first impregnation portion 54 (signal substance generator-impregnated portion). On this was further superposed a circular member of 12 mm in diameter prepared by punching surfactant-treated ELTAS (catalog No. A05070, manufactured by Asahi Chemical Industry) to be used as the filter portion 52.

This was covered with the acrylic upper cover 50 having the sample-introducing hole 50a of 6 mm in diameter in such a manner that the center of the sample-introducing hole 50a coincided with the center of the through hole 68, and then the thus laminated members were fixed by screwing up the four corners of the upper cover 50 and the lower substrate 66. In this way, various types of the specific binding assay device shown in FIGS. 2 and 3 for use in the measurement of the concentration of hCG were constructed.

<7> Measurement of hCG in heparinized plasma

Using the counter electrode 70 of the electrode portion 60a of each of the thus constructed specific binding assay devices as a counter/reference electrode, its terminal 70a was connected to the counter electrode (reference electrode) terminal of µ-PGS10 Potentiostat/Galvanostat (manufactured by Teknologue) for 2 channel simultaneous measurement use, and the respective terminals 76a and 78a of the first working electrode 76 (detection means 1) and the second working electrode 78 (detection means 2) were connected with the channel 1 and channel 2 working electrode terminals of the instrument. The instrument was further connected to a computer via a GPIB line to carry out measurement and data processing.

Authentic hCG sample was added to 3 samples (A), (B) and (C) of heparinized healthy male plasma, in order to prepare heparinized plasma samples respectively containing 600 IU/L, 700 IU/L and 900 IU/L of hCG.

A 250 μl portion of each of the thus prepared hCG-containing heparinized plasma samples was introduced into the specific binding assay device through the sample-introducing hole 50a of the upper cover 50.

Thereafter, electrical potential of each working electrode was set to −150 mV against the counter/reference electrode, and current values were recorded.

Figure 13:
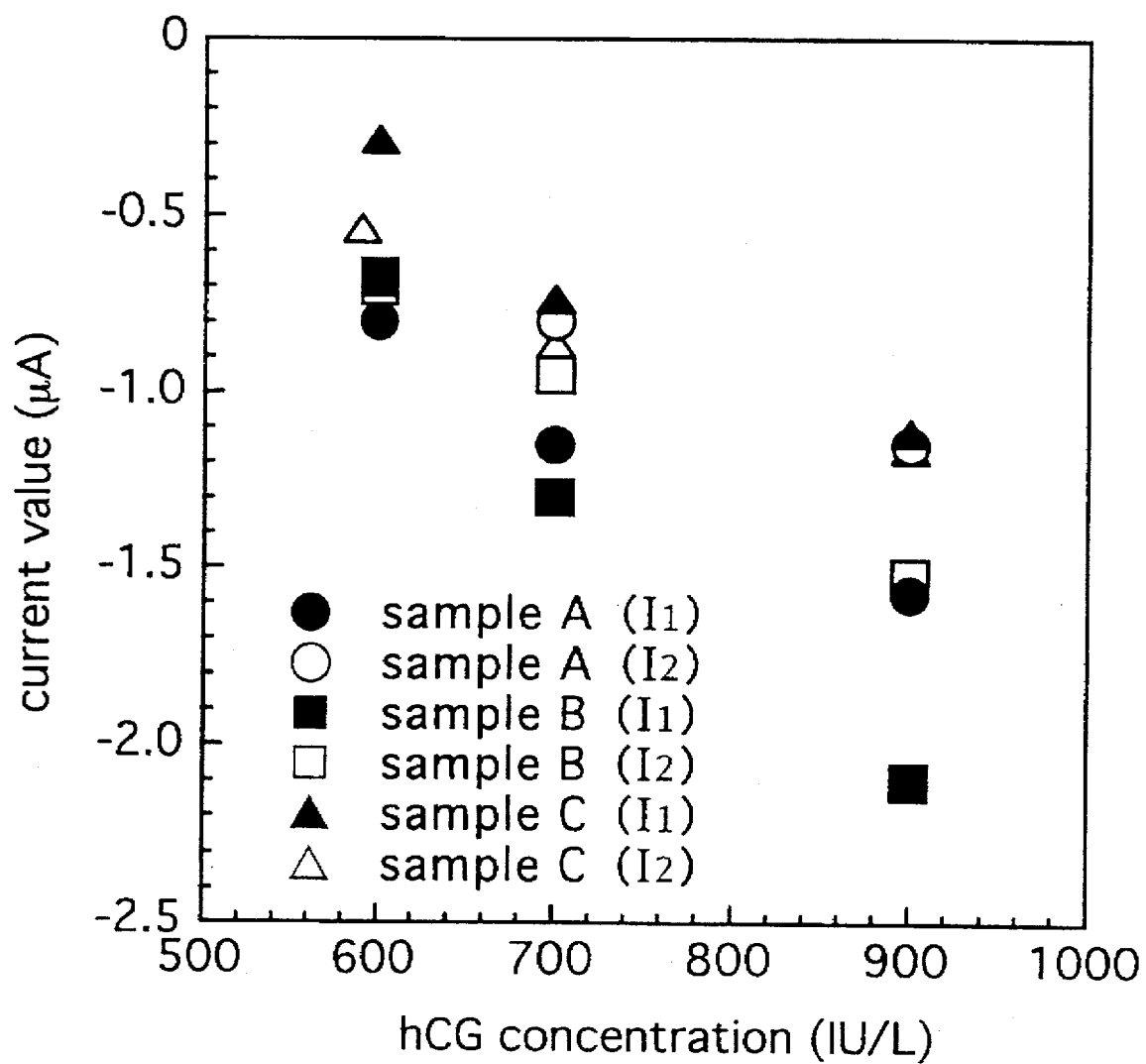
FIG. 13 is a graph showing a relationship between hCG concentrations and current values.

<8> Result-1 Derivation of an expression for use in the enumeration of hCG concentration from current values of plural detection means FIG. 13 shows average values of currents measured at the first and second working electrodes 76 and 78 ($I_1$ and $I_2$, respectively) for 6 to 8 minutes after introduction of each of the hCG solutions having different concentrations prepared using 3 heparinized plasma samples (A), (B) and (C).

Figure 14:
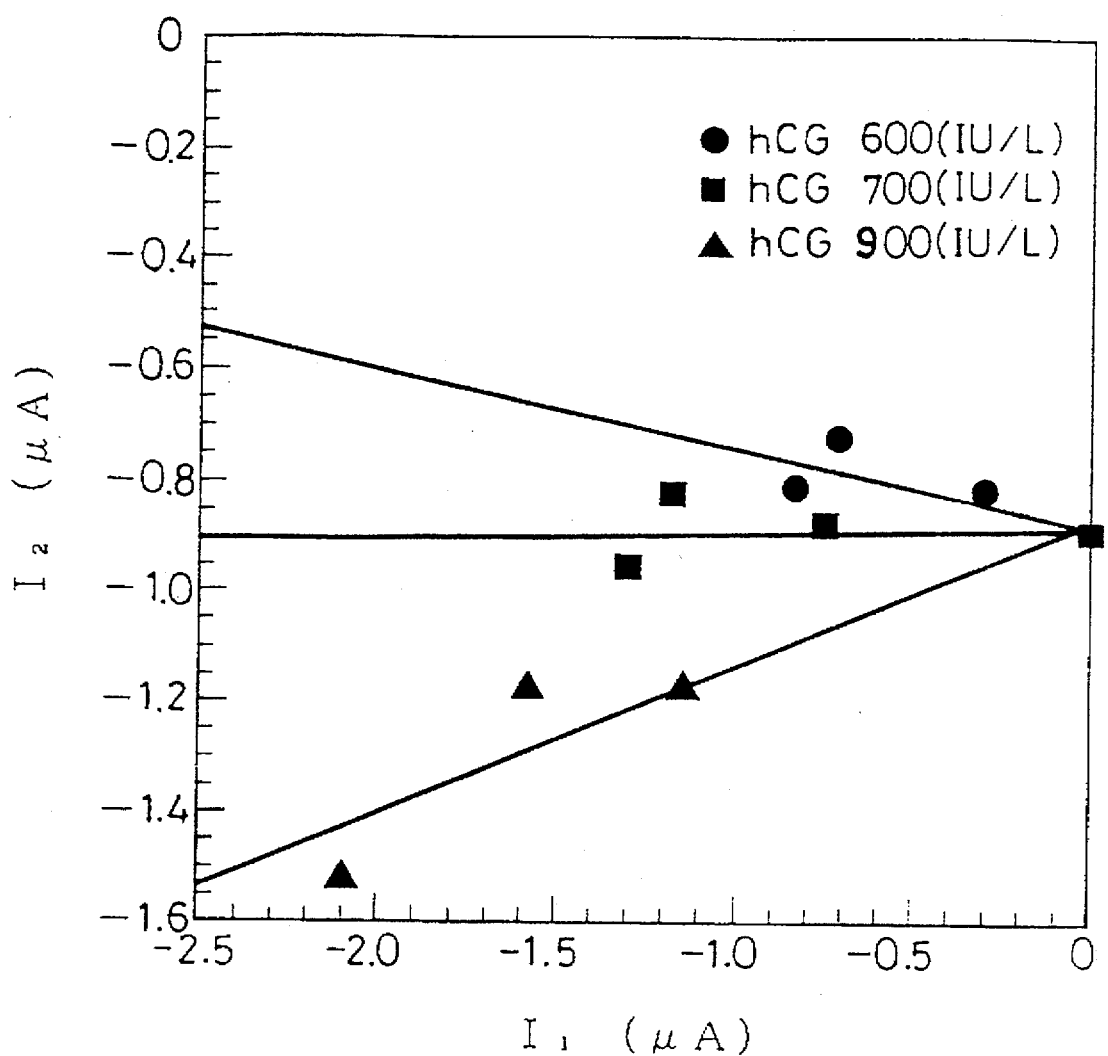
FIG. 14 is a graph showing a relationship between current values measured at detection means 1 and 2.

A relation of $I_2$ to $I_1$ at each hCG concentration is shown in FIG. 14. Since a linear relation of $I_2$ to $I_1$ was found at each hCG concentration as shown in FIG. 14, its linear regression expression was calculated among plasma samples, with the results shown in Table 4.

TABLE 4

| Concentration of hCG (IU/L) | Linear regression expression |
| --- | --- |
| 600 | $I_2 = -1.40 \times 10^{-1} I_1 - 8.82 \times 10^{-1}$ |
| 700 | $I_2 = 6.57 \times 10^{-3} I_1 - 8.89 \times 10^{-1}$ |
| 900 | $I_2 = 2.66 \times 10^{-1} I_1 - 8.71 \times 10^{-1}$ |

In this case, the intercept was almost independent of the hCG concentration (approximately $-8.8 \times 10^{-1}$), while the slope was dependent on the hCG concentration.

The relation of $I_2$ to $I_1$ is expressed by the following formula 1 in which S represents the slope of the above table and is the function of hCG concentration.

$$I_2 = SI_1 - 8.8 \times 10^{-1} \quad \text{formula 1}$$

Figure 15:
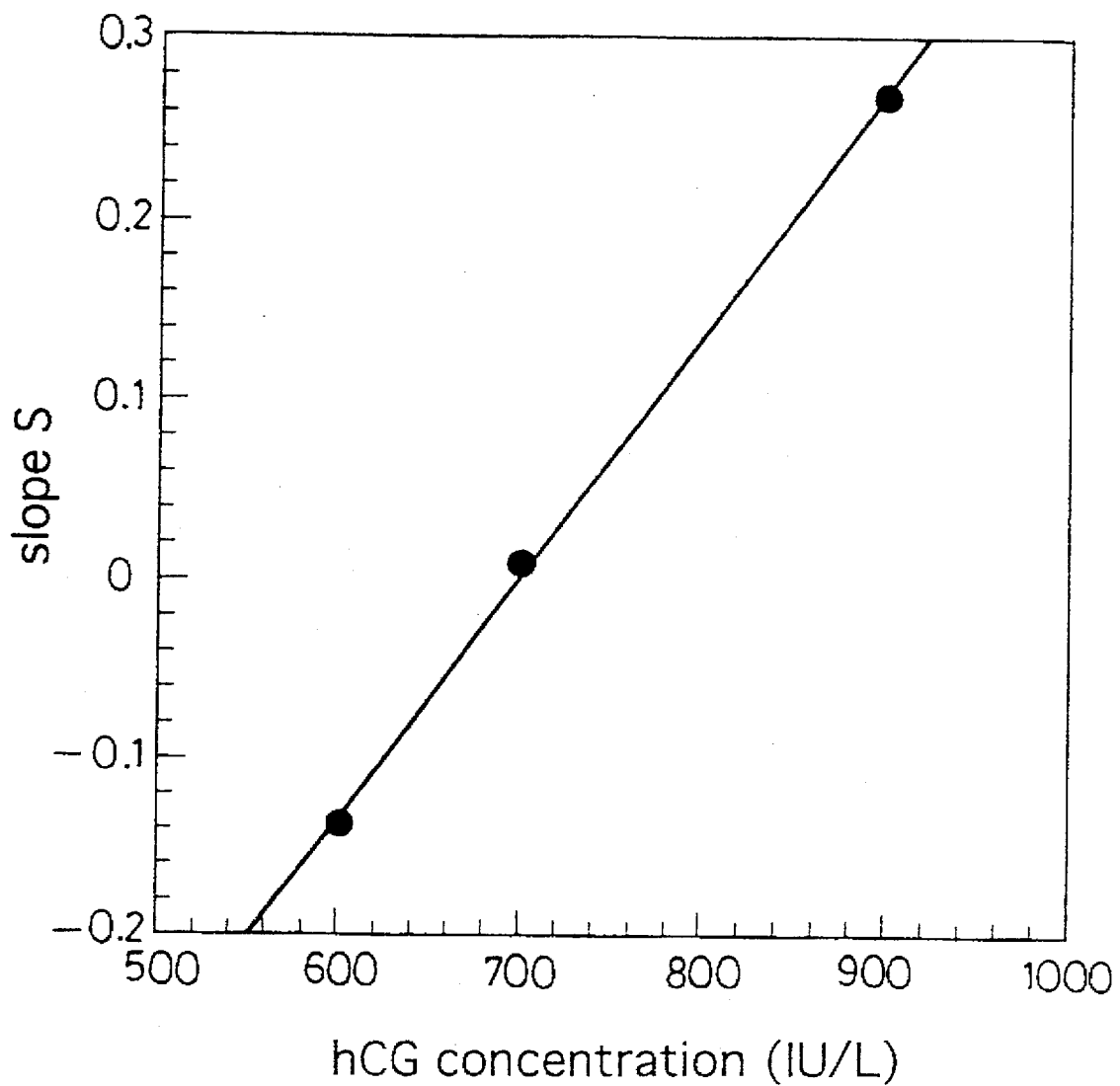
FIG. 15 is a graph showing a relationship between hCG concentrations and slopes.

On the basis of the above results, a linear relation between the hCG concentration C and the slope S of the formula 1 was assumed as shown in FIG. 15, and its linear regression expression (the following formula 2) was obtained to derive a relation of the slope (S) to the hCG concentration (C).

$$S = 1.36 \times 10^{3} C - 0.95 \quad \text{formula 2}$$

A relation formula (formula 3) for use in the enumeration of the hCG concentration from the current values $I_1$ and $I_2$ of the plural detection means was derived by substituting the formula 2 (relation of C and S) for S in the formula 1 (relation of $I_1$ and $I_2$).

$$C = \frac{I_2 + 0.88}{1.36 \times 10^{-3} I_1} + 6.99 \quad \text{formula 3}$$

<9> Result-2 Derivation of an expression for use in the enumeration of hCG concentration from current values of a single detection means (control experiment)

Figure 16:
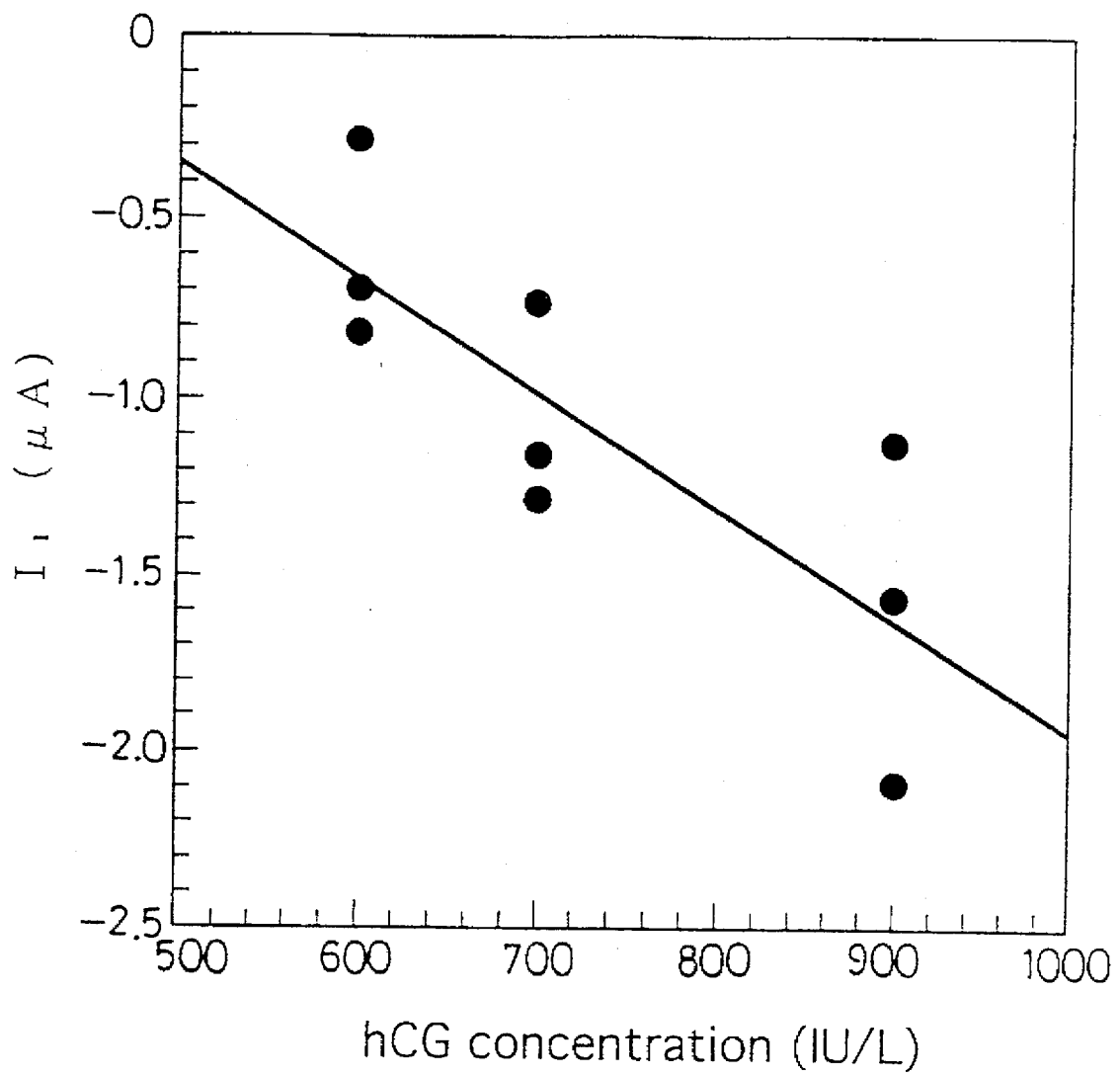
FIG. 16 is a graph showing a relationship between hCG concentrations and measured current values by the detection means 1.

Concentration of hCG in each test sample was calculated in the case of a single working electrode system, namely when the hCG concentration was determined by measuring distribution of the specific binding reaction in the anti-hCG antibody-immobilized porous nitrocellulose membrane by only one of the detection means. When the hCG concentration was determined only by $I_1$, a linear relation of $I_1$ to the hCG concentration was found as shown in FIG. 16. In consequence, a linear expression was obtained by linear regression, and a relation formula (the following formula 4) for use in the enumeration of hCG concentration from the current value $I_1$ of the single detection means was derived using the linear expression.

$$C = \frac{I_1 + 1.26}{3.22 \times 10^{-3}} \quad \text{formula 4}$$

<10> Result-3 Comparison of the Results 1 and 2

Concentrations of hCG were calculated and compared by substituting each of the current values for corresponding value in the relation formulae (aforementioned formulae 3 and 4) derived from the plural detection means measurement and the single detection means measurement. The results are shown in Table 5.

TABLE 5

| Sample | hCG (IU/L) | Assay results by plural detection means measured values (IU/L) | Assay results by single detection means measured values (IU/L) |
| --- | --- | --- | --- |
| A | 600 | 644 | 392 |
|   | 700 | 669 | 757 |
|   | 900 | 836 | 882 |
| B | 600 | 543 | 612 |
|   | 700 | 746 | 795 |
|   | 900 | 923 | 1044 |
| C | 600 | 564 | 484 |
|   | 700 | 703 | 624 |
|   | 900 | 890 | 747 |

Based on these results, average and CV values (coefficient of variation) of each hCG concentration between both measurements were compared, with the results shown in Table 6.

TABLE 6

| hCG (IU/L) | Measurement by plural detection means | | Measurement by single detection means | |
| --- | --- | --- | --- | --- |
| | average (IU/L) | CV (%) | average (IU/L) | CV (%) |
| 600 | 594 | 12.0 | 496 | 22.3 |
| 700 | 706 | 5.5 | 725 | 12.4 |
| 900 | 883 | 5.0 | 891 | 16.7 |

As shown in the above table, when the hCG concentration was determined using only $I_1$ values obtained by the single detection means measurement, the CV values became large due to influence of contaminants in the test samples.

On the contrary, when the hCG concentration was determined using $I_1$ and $I_2$ values obtained by the plural detection means measurement, the CV values were 12% or less which clearly indicated the correction effect on measuring error factors in the test samples.

In consequence, it was confirmed that the measuring accuracy is considerably improved when assayed using a plurality of detection means in comparison with the case of the use of a single detection means, even in the same assay process.

[Inventive Example 3]

Measurement of hCG concentration using specific binding assay device

<1> Preparation of a first impregnation portion 54 (signal substance generator- and electron mediator-impregnated portion, namely a dried body impregnated with horseradish peroxidase-labeled anti-hCGβ antibody and N,N,N',N'-tetrakis-(2'-hydroxyethyl)-p-phenylenediamine dihydrochloride (THEPD))

The horseradish peroxidase-labeled anti-hCGβ antibody prepared in the step <1> of Inventive Example 1 and THEPD (final concentration, 5 mM) were dissolved in 0.1M phosphate buffer (pH 6.0) containing 5% normal rabbit serum (NRS), 10% saccharose and 0.1M NaCl.

A 140 μl portion of the thus prepared solution was spotted on a circular filter paper of 12 mm in diameter obtained by punching the Tween 20-treated glass fiber filter paper prepared in the step <1> of Inventive Example 2, and the resulting filter paper was freeze-dried to obtain the first impregnation portion 54 (signal substance generator- and electron mediator-impregnated portion).

<2> Preparation of absorption means 64 (a dried body impregnated with hydrogen peroxide and urea)

A 100 μl portion of the 1.0M hydrogen peroxide-1.0M urea solution prepared in the step <4> of Inventive Example 2 was spotted on a circular filter paper of 12 mm in diameter obtained by punching a chromatograph filter paper (17 Chr, manufactured by Whatman), and the resulting filter paper was freeze-dried to obtain a dried body impregnated with hydrogen peroxide and urea.

<3> Construction of specific binding assay device

Using the thus prepared respective parts, various specific binding assay devices shown in FIGS. 2 and 3 were constructed in the following manner.

Firstly, the absorption means 64 (dried body impregnated with hydrogen peroxide and urea) was superposed on the acrylic base cover 66. A seal of 6 mm in diameter obtained by punching a mending tape (manufactured by Sumitomo 3M) was adhered on the center of the absorption means. Next, the channel 62 (anti-hCG antibody (SE030)-immobilized porous nitrocellulose membrane) prepared in the step <5> of inventive Example 2 was superposed on the water absorption filter paper having the sealing means 64a, by adjusting their centers at the same position.

On this was superposed the electrode portion 60a prepared in the aforementioned column [Preparation of electrode portion] in such a manner that the center of the through hole 68 coincided with the center of the channel 62 and the working electrode portion became down side. A circular filter paper having a diameter of 3 mm was prepared by punching from a glass fiber filter paper (GA55, manufactured by Advantech Toyo), inserted into the through hole of the electrode and used as the communication means 58.

Next, the surfactant (Tween 20)-treated glass fiber filter paper prepared in the step <1> of inventive Example 2 was used as the second impregnation portion 56 and superposed in such a manner that its center coincided with the center of the through hole of the electrode. On the center of the upper surface of the second impregnation portion 56 was adhered a seal of 6 mm in diameter obtained by punching a mending tape. On this was superposed the first impregnation portion 54 (signal substance generator- and electron mediator-impregnated portion). On this was further superposed a circular member of 12 mm in diameter prepared by punching surfactant-treated ELTAS (catalog No. A05070, manufactured by Asahi Chemical Industry) to be used as the filter portion 52.

This was covered with the acrylic upper cover 50 having the sample-introducing hole 50a of 6 mm in diameter in such a manner that the center of the sample-introducing hole 50a coincided with the center of the through hole 68, and then the thus laminated members were fixed by screwing up the four corners of the upper cover 50 and the base cover 66. In this way, various types of the specific binding assay device shown in FIGS. 2 and 3 for use in the measurement of the concentration of hCG were constructed.

<4> Measurement of hCG in heparinized plasma

The counter electrode 70 of the electrode portion 60a of each of the thus constructed specific binding assay devices was connected as a counter/reference electrode to the reference electrode terminal and counter electrode (reference electrode) terminal of μ-PGS10 Potentiostat/Galvanostat (manufactured by Teknologue) for 2 channel simultaneous measurement use, and the respective terminals 76a and 78a of the first working electrode 76 (detection means 1) and the second working electrode 78 (detection means 2) were connected with the channel 1 and channel 2 working electrode terminals of the instrument. The instrument was further connected to a computer via a GPIB line to carry out measurement and data processing.

Separately from this, authentic hCG sample was added to 3 samples (A), (B) and (C) of heparinized healthy male plasma, in order to prepare heparinized plasma samples respectively containing 50 IU/L, 100 IU/L and 200 IU/L of hCG.

A 250 μl portion of each of the thus prepared hCG-containing heparinized plasma samples was introduced into the specific binding assay device through the sample-introducing hole 50a of the upper cover 50.

Thereafter, electrical potential of each working electrode was set to −150 mV against the counter/reference electrode, and current values were recorded.

<5> Result-1 Derivation of an expression for use in the enumeration of hCG concentration from plural detection means-1

Figure 17:
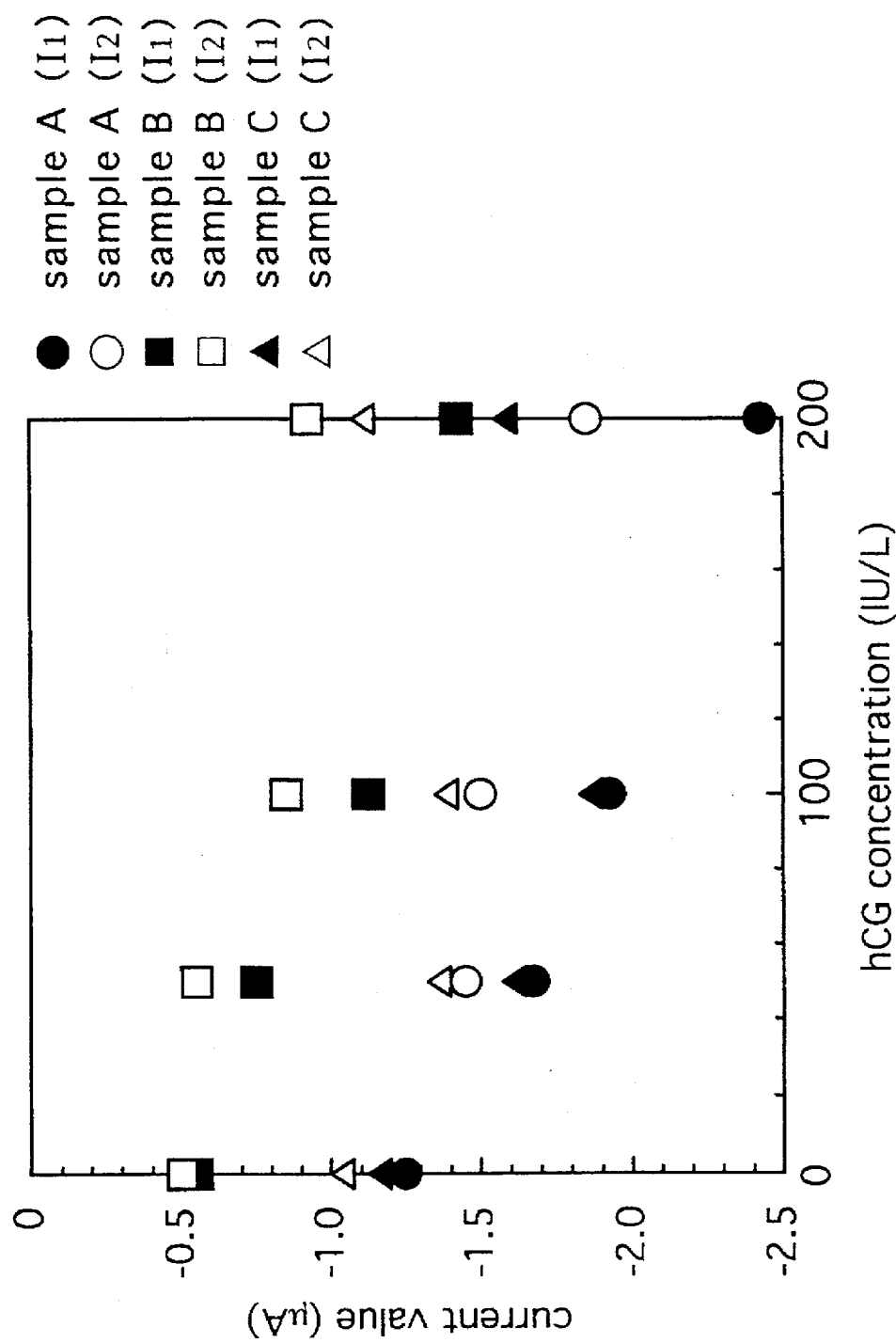
FIG. 17 is a graph showing a relationship between hCG concentrations and current values.
Figure 18:
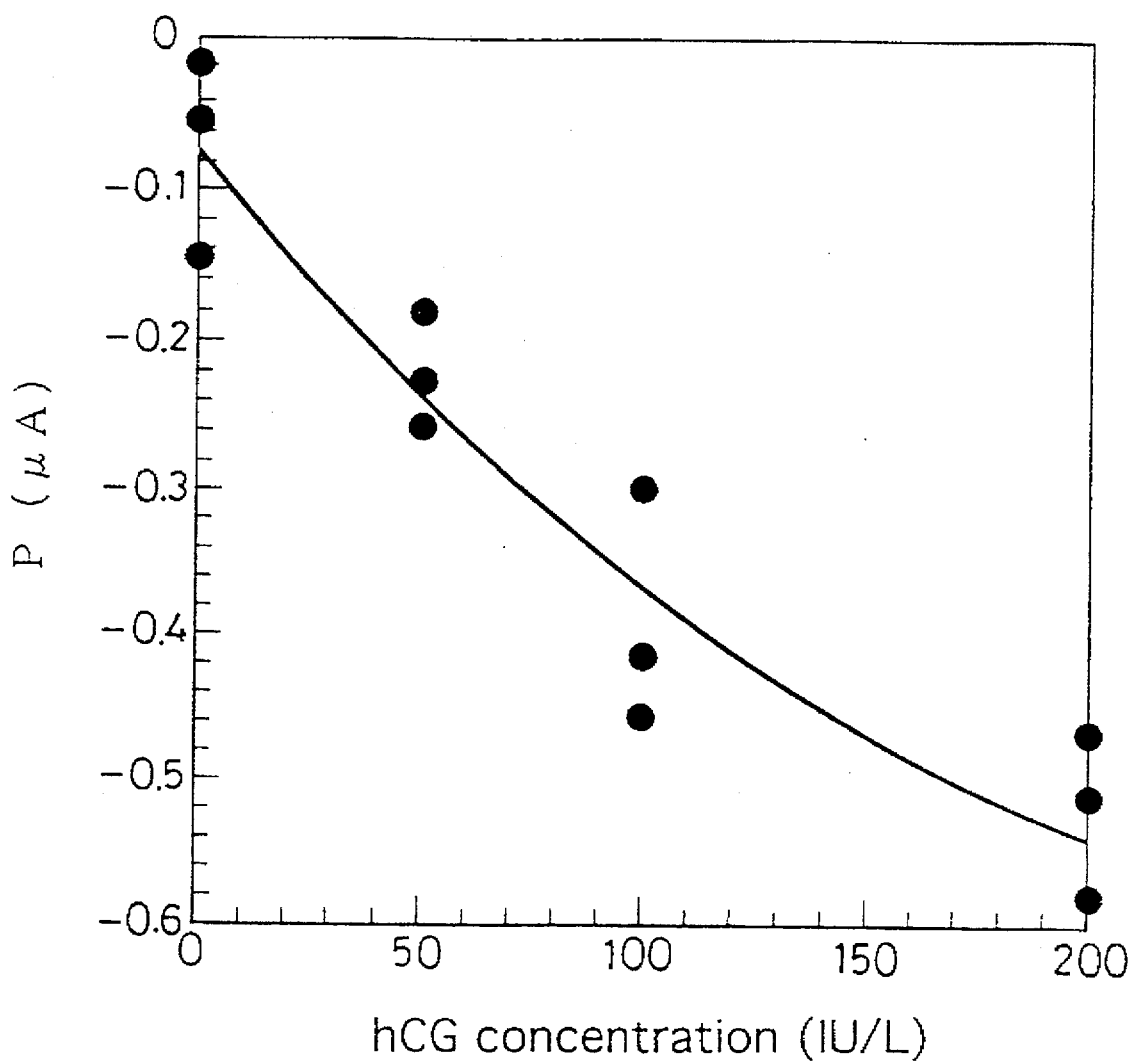
FIG. 18 is a graph showing a relationship between hCG concentrations and parameter P.

FIG. 17 shows average values of currents measured at the first and second working electrodes 76 and 78 ($I_1$ and $I_2$) for 8 to 10 minutes after introduction of each of the hCG solutions having different concentrations prepared using 3 heparinized plasma samples (A), (B) and (C). A relation of parameter ($P=I_1-I_2$) obtained by subtracting $I_2$ from $I_1$ at each hCG concentration is shown in FIG. 18.

A relational formula between the parameter P and the hCG concentration C was obtained from the correlation of P to each hCG concentration C in each test sample (formula 5).

$$P=5.99 \cdot 10^{-6}C^2 - 3.52 \times 10^{-3}C - 7.59 \times 10^{-2} \qquad \text{formula 5}$$

A relation formula (formula 6) for use in the enumeration of the hCG concentration (C) was derived from the formula 5.

$$C = \frac{3.52 \times 10^{-3} - (1.42 \times 10^{-5} + 2.40 \times 10^{-5} \times P)^{1/2}}{1.2 \times 10^{-5}} \qquad \text{formula 6}$$

<6> Result-2 Derivation of a relation formula for use in the enumeration of hCG concentration from current values of a single detection means (control experiment)-1

Concentration (C) of hCG in each test sample was calculated in the case of a single working electrode system, namely when the hCG concentration was determined by measuring distribution of the specific binding reaction in the channel 62 (in the anti-hCG antibody-immobilized porous nitrocellulose membrane) by only $I_1$ or $I_2$.

Figure 19:
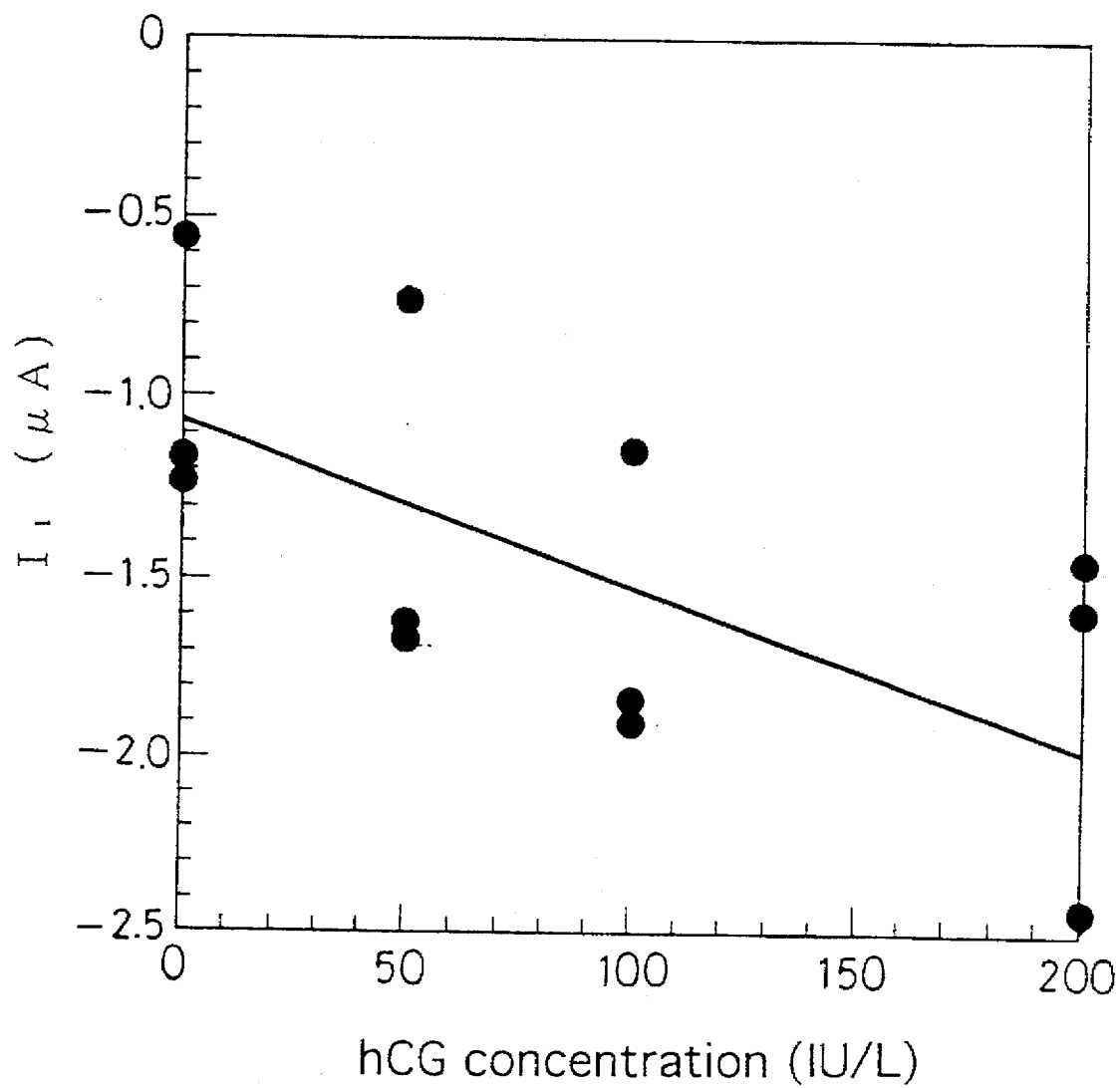
FIG. 19 is a graph showing a relationship between hCG concentrations and current values measured by the detection means 1.
Figure 20:
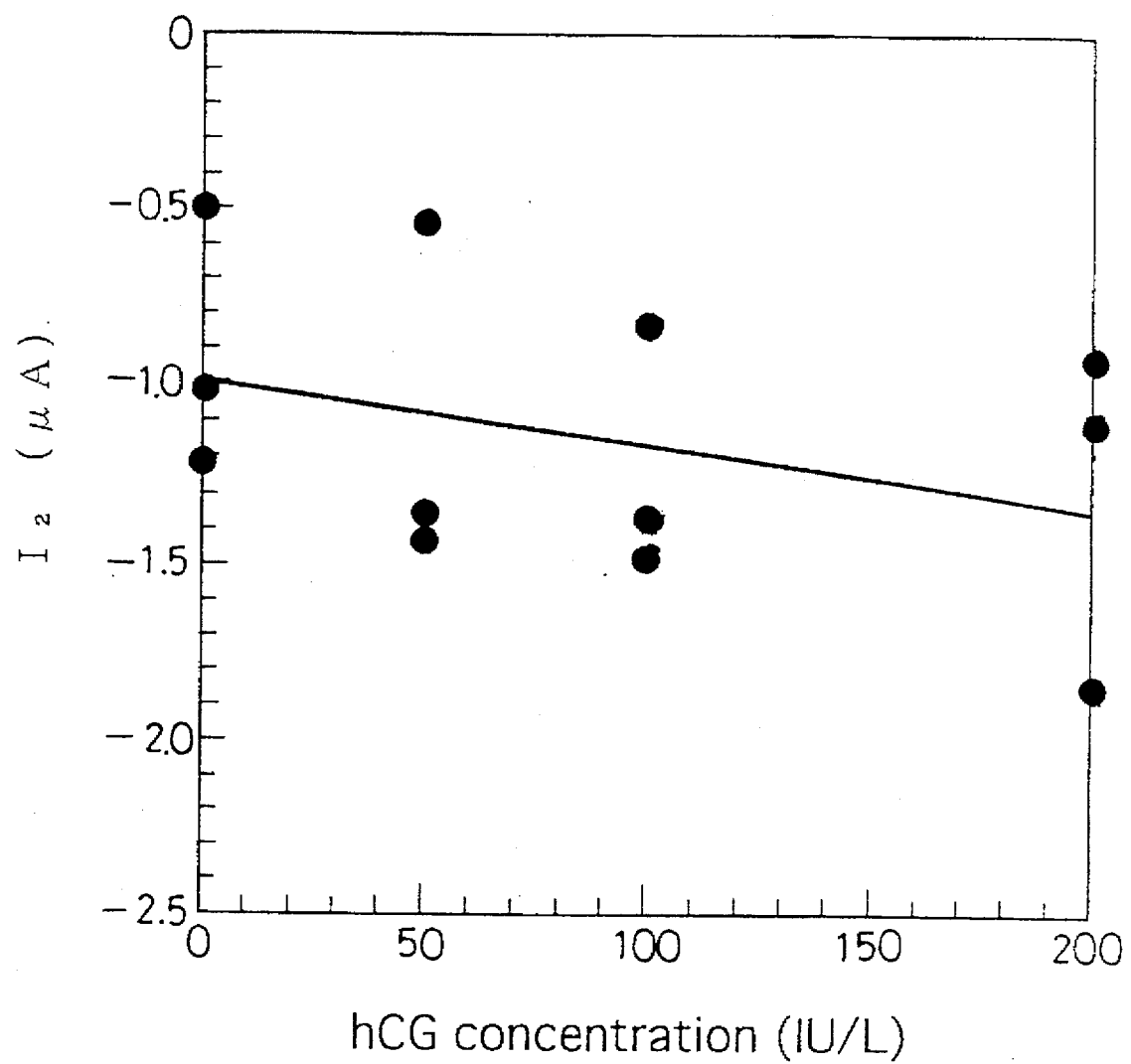
FIG. 20 is a graph showing a relationship between hCG concentrations and current values measured by the detection means 2.

Relation formulae (formulae 7 and 8) were obtained for use in the enumeration of hCG concentration (C) from a correlation of $I_1$ to the hCG concentration (FIG. 19) when hCG is determined by only $I_1$ or from a correlation of $I_2$ to the hCG concentration (FIG. 20) when hCG is determined by only $I_2$.

Determination of hCG by only $I_1$ $$C = \frac{I_1 + 1.10}{-4.05 \times 10^{-3}} \quad \text{formula 7}$$

Determination of hCG by only $I_2$ $$C = \frac{I_2 + 9.91 \times 10^{-1}}{-1.82 \times 10^{-3}} \quad \text{formula 8}$$

Concentrations of hCG were calculated by substituting each of the current values for corresponding value in the relation formulae (formulae 6, 7 and 8) derived from the plural detection means measurement and the single detection means measurement, in order to compare average hCG concentration and CV value of each measurement. The results are shown in Table 7.

TABLE 7

| hCG (IU/L) | Plural detection means | | Single detection means ($I_1$) | | Single detection means ($I_2$) | |
|---|---|---|---|---|---|---|
| | average (IU/L) | CV (%) | average (IU/L) | CV (%) | average (IU/L) | CV (%) |
| 50 | 47 | 28 | 62 | 210 | 73 | 371 |
| 100 | 113 | 32 | 133 | 78 | 140 | 135 |
| 200 | 196 | 27 | 181 | 73 | 174 | 152 |

As shown in the table 7, when the hCG concentration was determined using only $I_1$ or $I_2$ values obtained by the single detection means measurement, the CV values were considerably large, and dispersion among test samples was not able to be corrected, thus completely failing in providing reliability of the assay results.

On the contrary, when the hCG concentration was determined using $I_1$ and $I_2$ values obtained by the plural detection means measurement, the CV value at each hCG concentration was markedly small which indicated sufficient correction effect.

<7> Result-3 Derivation of an expression for use in the enumeration of hCG concentration from plural detection means-2

Average values $D_1$ and $D_2$ of the current density (current value/each electrode area, μA/cm$^2$) were calculated from the average values of currents measured at the first and second working electrodes 76 and 78 ($I_1$ and $I_2$) for 8 to 10 minutes in the aforementioned assay of each of the hCG solutions having different concentrations prepared using 3 heparinized plasma samples (A), (B) and (C).

A value obtained by subtracting a background (−1.5 μA/cm$^2$) from the $D_1$ value at each hCG concentration was divided by another value obtained by subtracting a background (−0.2 μA/cm$^2$) from the $D_2$ value, and a constant 1.3 was subtracted from the divided value to obtain a parameter Q. A relationship between the parameter Q and the hCG concentration is shown in FIG. 21.

Figure 21:
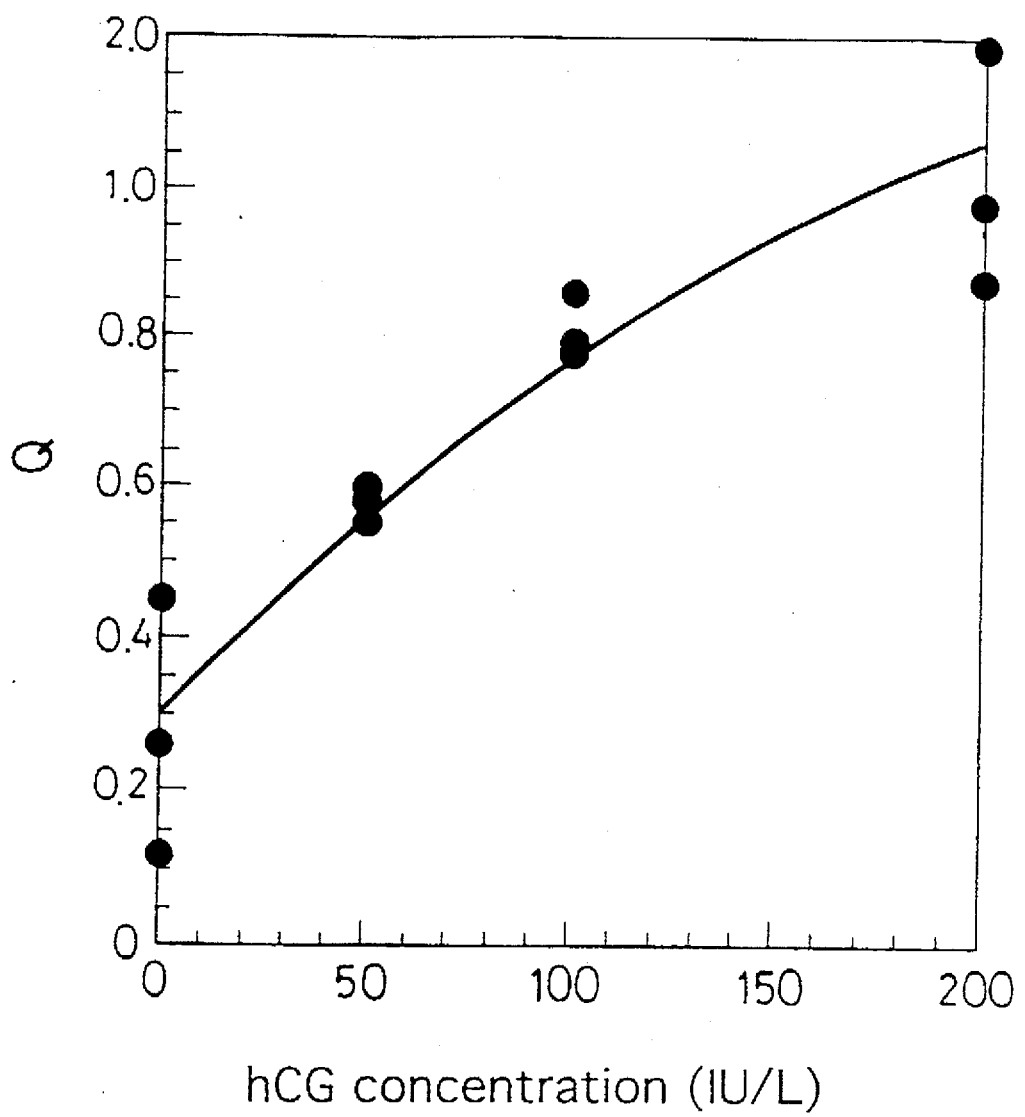
FIG. 21 is a graph showing a relationship between hCG concentrations and parameter Q.

Using the correlation of $Q=[(D_1+1.5)/(D_2+0.2)]-1.3$ to each hCG concentration (C) shown in FIG. 21, a relation expression (formula 9) for use in the enumeration of the hCG concentration was obtained.

$$C = \frac{5.50 \times 10^{-3} - (4.07 \times 10^{-5} - 3.43 \times 10^{-5} Q)^{1/2}}{1.71 \times 10^{-5}} \quad \text{formula 9}$$

<8> Result-4 Derivation of an expression for use in the enumeration of hCG concentration from a single detection means-2

Concentration (C) of hCG in each test sample was calculated in the case of a single detection means, namely when the hCG concentration was determined based on only $D_1$ or $D_2$.

Relation formulae (formulae 10 and 11) were obtained for use in the enumeration of hCG concentration (C) from a correlation of $D_1$ to the hCG concentration when determined by only $D_1$ or from a correlation of $D_2$ to the hCG concentration when determined by only $D_2$.

Determination of hCG by only $D_1$ $$C = \frac{D_1 + 8.73}{-3.23 \times 10^{-2}} \quad \text{formula 10}$$

Determination of hCG by only $D_2$ $$C = \frac{D_2 + 4.51}{-8.28 \times 10^{-3}} \quad \text{formula 11}$$

Concentrations of hCG were calculated by substituting each of the current densities for corresponding value in the relation formulae (formulae 9, 10 and 11) derived from the plural detection means measurement and the single detection means measurement, in order to compare average hCG concentration and CV value of each measurement. The results are shown in Table 8.

TABLE 8

| hCG (IU/L) | Plural detection means | | Single detection means ($I_1$) | | Single detection means ($I_2$) | |
|---|---|---|---|---|---|---|
| | average (IU/L) | CV (%) | average (IU/L) | CV (%) | average (IU/L) | CV (%) |
| 50 | 55 | 9 | 61 | 210 | 73 | 372 |
| 100 | 110 | 11 | 132 | 78 | 139 | 136 |
| 200 | 196 | 45 | 180 | 72 | 173 | 153 |

As shown in the table 8, determination of hCG making use of the relation formula 9 showed the correction effect clearly, similar to the case of the use of the relation formula 6, thus confirming that the influences of contaminants in a test sample can be offset by these formulae.

[Inventive Example 4]

The procedure of Inventive Example 3 was repeated except for the use of 3 types (A), (B) and (C) of the first impregnation portion 54 (signal substance generator- and electron mediator-impregnated portion) containing different inactivation degrees of horseradish peroxidase-labeled anti-hCGβ antibody. Using 3 types of the resulting specific binding assay device (to be referred to as "specific binding assay devices (A), (B) and (C)" hereinafter), hCG in heparinized plasma samples (hCG contents, 200 IU/L and 400 IU/L) were measured in the same manner as described in Inventive Example 3.

<Results>

From the results of the measurement by the specific binding assay devices (A), (B) and (C) using the first impregnation portion 54 impregnated with horseradish peroxidase-labeled anti-hCGβ antibodies having different inactivation degrees, average values $D_1$ and $D_2$ of current densities for 4 to 5 minutes were obtained and substituted for corresponding values in a relation formula derived from a plural detection means measurement or from a single detection means measurement ($D_1$) to calculate hCG concentrations in the same manner as described in the steps <7> and <8> of Inventive Example 3. The results are shown in Table 9.

TABLE 9

| Labeled antibody | Assay by plural detection means (IU/L) | Assay by single detection means (IU/L) |
| --- | --- | --- |
| Determined hCG concentration in 200 hCG IU/L sample | | |
| (A) | 210 | 30 |
| (B) | 240 | 40 |
| (C) | 170 | not determinable |
| Determined hCG concentration in 400 hCG IU/L sample | | |
| (A) | 370 | 280 |
| (B) | 370 | 310 |
| (C) | 420 | 180 |

As shown in the above table, inactivation of the enzyme in the enzyme-labeled antibody was successfully corrected by the use of the relation formula derived from the plural detection means measurement.

[Inventive Example 5]

The specific binding assay device of Inventive Example 3 was constructed, and hCG content in a heparinized plasma sample (hCG 400 IU/L) was measured at 25° C. and 40° C. in Constant Temperature Testing Chambers model IV21 (manufactured by Yamato Kagaku).

In the same manner as described in the steps <7> and <8> of Inventive Example 3, average values $D_1$ and $D_2$ of current densities for 4 to 5 minutes were obtained and substituted for corresponding values in a relation formula derived from a plural detection means measurement or for a relation formula derived from a single detection means measurement ($D_1$) to calculate hCG concentrations. The results are shown in Table 10.

TABLE 10

| Temperature (°C.) | Assay by plural detection means (IU/L) | Assay by single detection means (IU/L) |
| --- | --- | --- |
| 25 | 400 | 400 |
| 40 | 400 | 550 |

As shown in the above table, influence of temperature was successfully corrected by the use of the relation formula derived from the plural detection means measurement.

[Inventive Example 6]

Measurement of hCG concentration in whole blood using specific binding assay device
<1> Preparation of a first impregnation portion 54 (signal substance generator- and electron mediator-impregnated portion, namely a dried body impregnated with horseradish peroxidase-labeled anti-hCGβ antibody and N,N,N',N'-tetrakis-(2'-hydroxyethyl)-p-phenylenediamine dihydrochloride (THEPD))

The horseradish peroxidase-labeled anti-hCGβ antibody prepared in the step <1> of Inventive Example 1 and THEPD (final concentration, 2 mM) were dissolved in 0.1M phosphate buffer (pH 6.0) containing 5% normal rabbit serum (NRS), 10% saccharose and 0.1M NaCl.

A 140 μl portion of the thus prepared solution was spotted on a circular filter paper of 12 mm in diameter obtained by punching the Tween 20-treated glass fiber filter paper prepared in the step <1> of Inventive Example 2, and the resulting filter paper was freeze-dried to obtain the first impregnation portion 54 (signal substance generator- and electron mediator-impregnated portion).

<2> Preparation of a second impregnation portion 56 (buffer solution component-impregnated portion, namely a dried body impregnated with 0.1M phosphate buffer (pH 6.0) containing 0.1M NaCl)

A 140 μl portion of 0.1M phosphate buffer (pH 6.0) containing 0.1M NaCl was spotted on a circular filter paper of 12 mm in diameter obtained by punching the Tween 20-treated glass fiber filter paper prepared in the step <1> of Inventive Example 2, and the resulting filter paper was freeze-dried to obtain a dried body impregnated with the buffer component.

<3> Preparation of channel 62 (antibody-immobilized membrane, namely an anti-hCG antibody-immobilized porous cellulose ester mixture membrane)

A rabbit polyclonal antibody SE030 (prepared by Mochida Pharmaceutical) which recognizes hCG was dissolved in PBS containing ethanol (final concentration, 20%) to prepare an antibody solution of 6.4 mg/ml. On a Petri dish, a 30 μl portion of the solution was spotted on the center of a circular porous membrane of 16 mm in diameter obtained by punching a cellulose mixture ester porous membrane having a pore size of 8.0 μm (catalog No. SCWP0190R, manufactured by Nippon Millipore). After 2 hours of drying in a desiccator at room temperature, the circular membrane was further punched into a diameter of 13 mm to obtain the channel 62 (anti-hCG antibody (SE030)-immobilized porous cellulose ester mixture membrane).
<4> Construction of specific binding assay device Using the thus prepared respective parts, various specific binding assay devices shown in FIGS. 2 and 3 were constructed in the following manner.

Firstly, the absorption means 64 (dried body impregnated with hydrogen peroxide and urea) prepared in Inventive Example 3 was superposed on the acrylic lower substrate 66. A seal of 8 mm in diameter obtained by punching a mending tape (manufactured by Sumitomo 3M) was adhered on the center of the absorption means. Next, the channel 62 (anti-hCG antibody (SE030)-immobilized porous nitrocellulose membrane) was superposed on the water absorption filter paper having the sealing means 64a, by adjusting their centers at the same position.

On this was superposed the electrode portion 60a in such a manner that the center of the through hole 68 coincided with the center of the channel 62 and the working electrode portion became down side. A circular filter paper having a diameter of 3 mm was prepared by punching from a glass fiber filter paper (GA55, manufactured by Advantec Toyo), inserted into the through hole of the electrode and used as the communication means 58.

Next, the second impregnation portion 56 (buffer solution component-impregnated portion) was superposed in such a manner that its center coincided with the center of the through hole of the electrode. On the center of the upper surface of the second impregnation portion 56 was adhered a seal of 6 mm in diameter obtained by punching a mending tape. On this was superposed the first impregnation portion 54 (signal substance generator- and electron mediator-impregnated portion). On this was further superposed a circular member of 12 mm in diameter prepared by punching surfactant-treated ELTAS (catalog No. A05070, manufactured by Asahi Chemical industry) to be used as the filter portion 52.

This was covered with the acrylic upper cover 50 having the sample-introducing hole 50a of 6 mm in diameter in such a manner that the center of the sample-introducing hole 50a coincided with the center of the through hole 68, and then the thus laminated members were fixed by screwing up the four corners of the upper cover 50 and the base cover 66. In this way, various types of the specific binding assay device shown in FIGS. 2 and 3 for use in the measurement of the concentration of hCG were constructed.

<5> Measurement of hCG in heparinized whole blood

The counter electrode 70 of the electrode portion 60a of each of the thus constructed specific binding assay devices was connected as a counter/reference electrode to the counter electrode (reference electrode) terminal of a current measuring circuit, and the respective terminals 76a and 78a of the first working electrode 76 (detection means 1) and the second working electrode 78 (detection means 2) were connected with the channel 1 and channel 2 working electrode terminals of the circuit. The circuit was further connected to a computer via a data gathering board AT-MIO-16X (manufactured by National instruments) to carry out data processing.

Separately from this, 4 heparinized healthy male whole blood samples (A), (B), (C) and (D) were collected using a Venoject II vacuum blood collection tube (manufactured by Terumo Corp.), and authentic hCG was added in an amount of 50 IU/L or 100 IU/L to the sample (A), 25 IU/L, 50 IU/L or 75 IU/L to the samples (B) and (C) and 50 IU/L to the sample (D).

A 250 µl portion of each of the thus prepared hCG-containing heparinized whole blood samples was introduced into the specific binding assay device through the sample-introducing hole 50a of the upper cover 50.

Thereafter, electrical potential of each working electrode was set to −150 mV against the counter/reference electrode, and current values were recorded.

<6> Measurement of hCG concentration in each blood sample by enzyme immunoassay using microtiterplate When hCG is added to whole blood, the added amount does not reflect its actual concentration because of the dissolution of hCG in plasma component, so that it is necessary to carry out correction of the concentration by hematocrit value.

In consequence, a whole blood sample prepared by adding hCG to whole blood was subjected to plasma separation, and hCG contained in the plasma was determined by an enzyme immunoassay using microtiter plate in the following manner to be used as the hCG actual concentration.

A rabbit polyclonal antibody SE030 which recognizes hCG was dissolved in PBS in an amount of 10 µg/ml, and a 50 µl portion of the solution was added to NUNC-IMMUNO PLATE (manufactured by NUNC) and incubated at 56° C. for 30 minutes. After washing with deionized water, 100 µl of 0.5% BSA solution in PBS was added to the plate and incubated at room temperature for 1.5 hours to effect blocking.

After removing the BSA solution, to the resulting plate was added 50 µl of an authentic hCG sample diluted to 0, 10, 20, 50, 100 or 200 IU/L or a heparinized plasma sample obtained from an hCG-added whole blood sample by centrifugation, followed by 1 hour of reaction at room temperature. After washing five times with a washing solution and twice with deionized water in that order, to the resulting plate was added 50 µl of a horseradish peroxidase-labeled anti-hCGβ antibody (HRPO-HM81) which has been diluted with 0.1M phosphate buffer (pH 6.0) containing 0.1% BSA and 0.1M NaCl, followed by 1 hour of reaction at room temperature. After washing the resulting plate five times with a washing solution and twice with deionized water in that order, 50 µl of TMB Soluble Reagent (manufactured by Scy Tck) was added thereto and 15 minutes of the coloring enzyme reaction was carried out. The enzyme reaction was stopped by adding 100 µl of TMB Stop Buffer (manufactured by Scy Tck).

Thereafter, absorbance of the color was measured using a spectrophotometer ETY96 (manufactured by Toyo Sokki) to calculate the hCG actual concentration in each heparinized plasma sample from the standard curve of authentic hCG.

Figure 22:
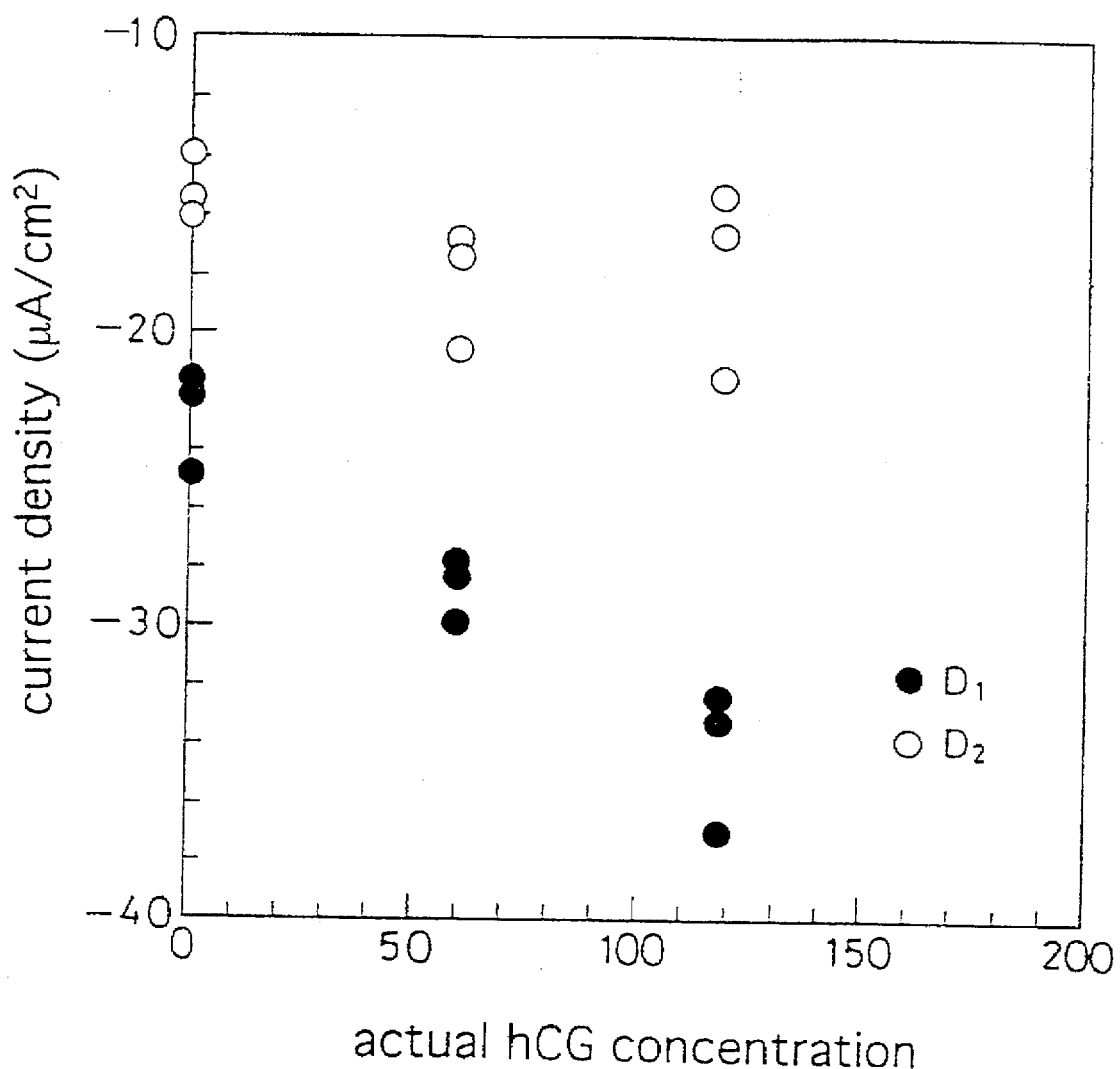
FIG. 22 is a graph showing a relationship between hCG concentrations and current densities.

<7> Result Derivation of an expression for use in the enumeration of hCG concentration from plural detection means Average current density values ($D_1$ and $D_2$) were calculated from the average current values $I_1$ and $I_2$ measured for 10 to 12 minutes at the first and second working electrodes 76 and 78 after application of each of the hCG solutions having different concentrations prepared using the heparinized whole blood sample (A). A relationship between the hCG actual concentration and the current density is shown in FIG. 22.

A value obtained by subtracting a background (−23 µA/cm$^2$) from the $D_1$ value at each hCG actual concentration was divided by the $D_2$ value to obtain a parameter Q. A relationship between the hCG actual concentration and the parameter Q is shown in FIG. 23.

Figure 23:
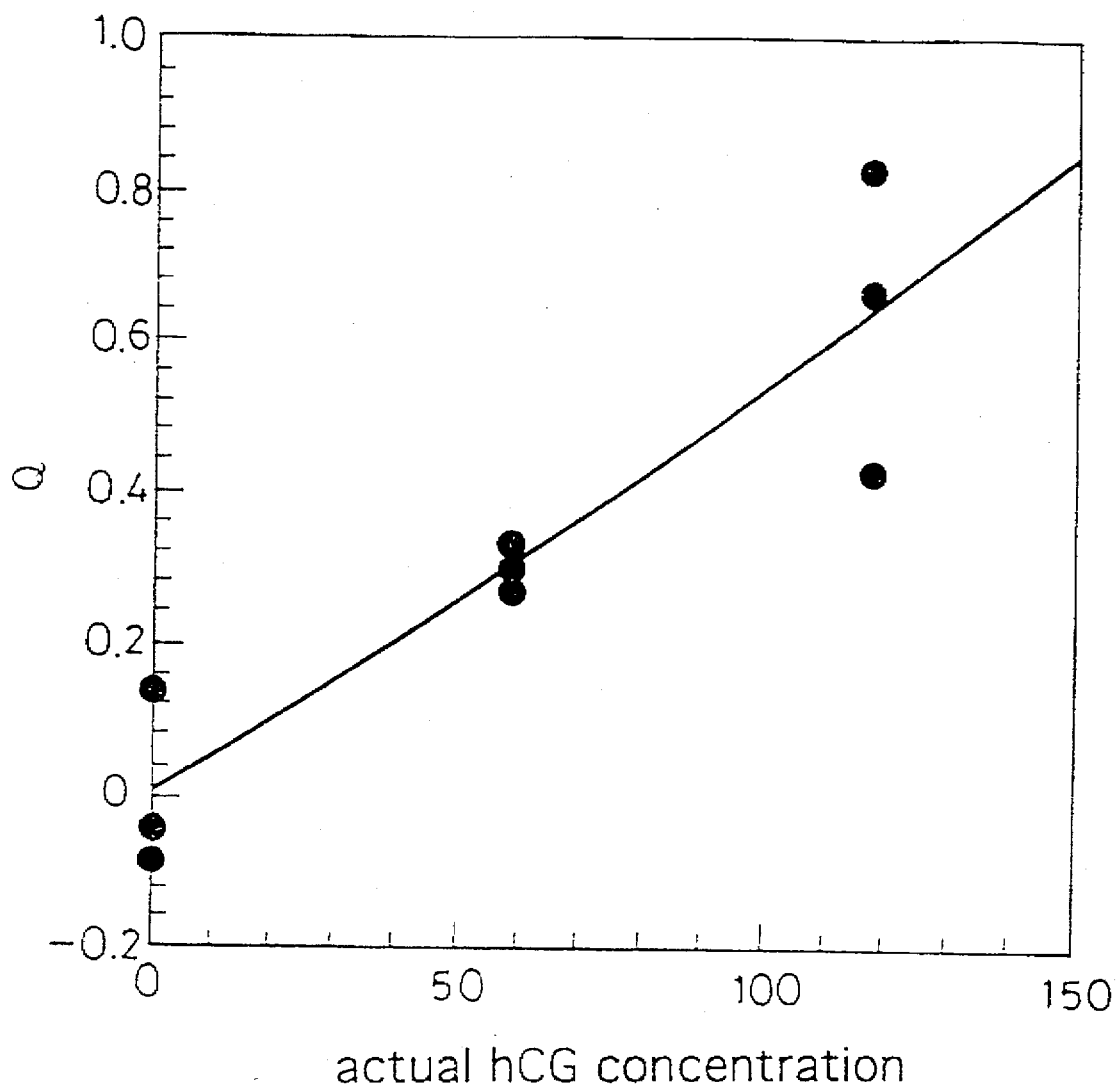
FIG. 23 is a graph showing a relationship between hCG concentrations and parameter Q.

Using the correlation of $Q=(D_1+23)/D_2$ to each hCG actual concentration (C) shown in FIG. 23, a relation formula (formula 12) for use in the enumeration of the hCG concentration was obtained.

$$C = \frac{-4.83 \times 10^{-3} + (2.28 \times 10^{-5} + 2.21 \times 10^{-5} \times Q)^{1/2}}{1.10 \times 10^{-5}} \quad \text{formula 12}$$

Next, each of the Q values of the heparinized whole blood hCG samples (B), (C) and (D) was substituted for Q in the formula 12 to calculate the hCG concentration and find its correlation to the whole blood hCG actual concentration measured by the enzyme immunoassay of the aforementioned step <6>.

Figure 24:
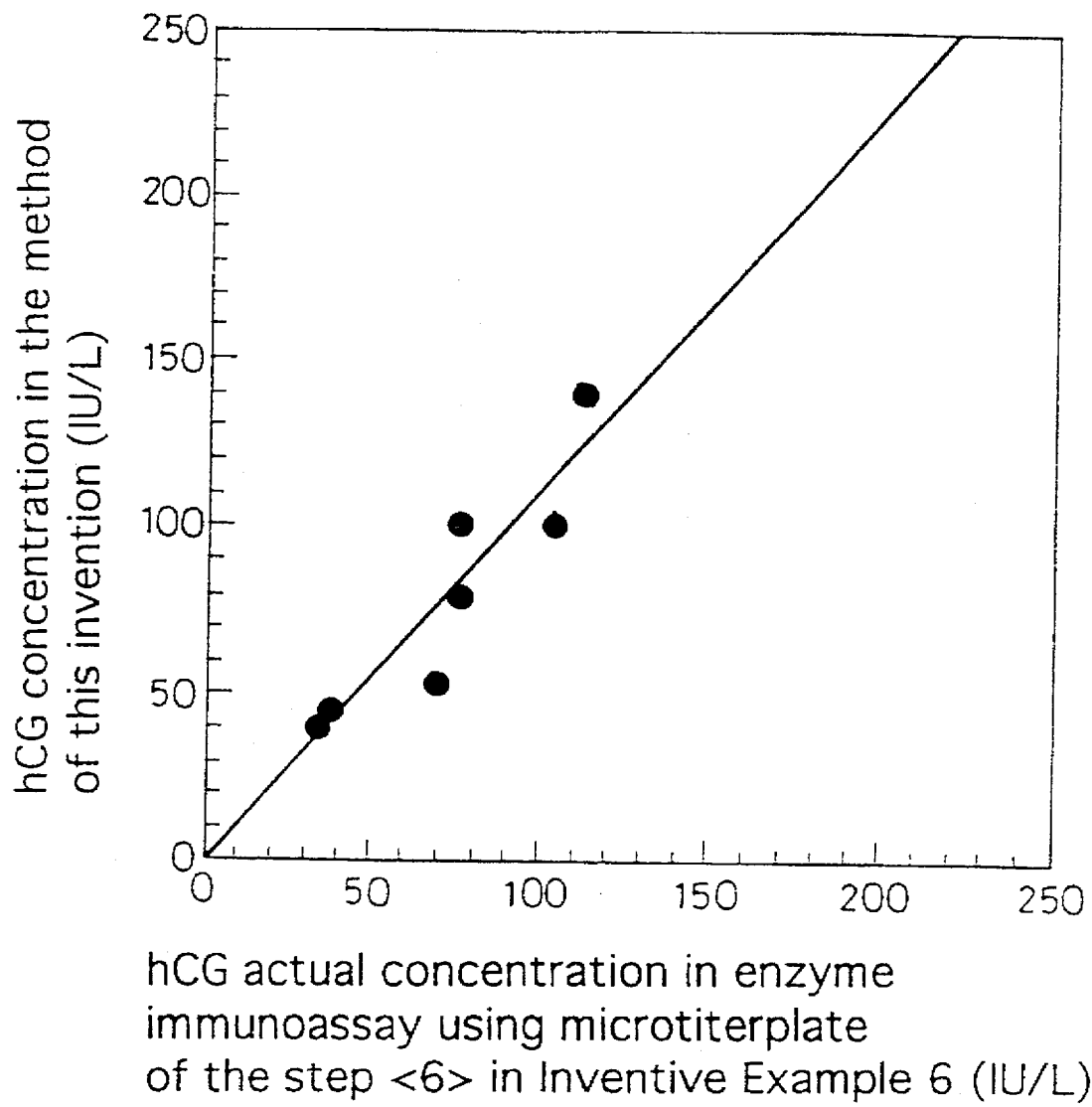
FIG. 24 is a graph showing a relationship between hCG concentrations measured by the specific binding assay (device) of the present invention and those measured by enzyme immunoassay using microtiterplate.

As shown in FIG. 24, the results showed excellent correlation between them, thus confirming significant correction effect of the plural detection means.

[Inventive Example 7]

Measurement of E2 concentration in whole blood samples by competitive assay method using specific binding assay device <1> Preparation of a conjugate (signal substance generator) of anti-E2 antibody and horseradish peroxidase Mouse monoclonal antibody F815 (prepared by Mochida Pharmaceutical) which recognizes E2 was dissolved in a buffer solution consisting of 100 mM sodium chloride, 1 mM EDTA and 60 mM triethanolamine (pH 8.0, to be referred to as "TEA buffer" hereinafter) to a final concentration of 5.3 mg/ml, and the resulting solution was dialyzed thoroughly against the TEA buffer which has been purged with nitrogen.

A 70 µl portion of 50 mM 2-iminothiolane hydrochloride (manufactured by Pierce Chemical Company) solution in TEA buffer was added to 2.2 ml of the thus prepared antibody solution, and the mixture was stirred and then allowed to stand still for 1.5 hours at 4° C. in an atmosphere of nitrogen gas. Thereafter, the resulting solution was thoroughly dialyzed against a buffer solution consisting of 100 mM sodium chloride, 1 mM EDTA and 100 mM phosphate (pH 6.0, to be referred to as "EDTA-PB" hereinafter) which has been pureged with nitrogen. In this way, SH group-introduced anti-E2 antibody was obtained.

A 3.1 ml portion of horseradish peroxidase (to be referred to as "HRPO" hereinafter, manufactured by Toyobo) solution prepared by dissolving it in 100 mM phosphate buffer (pH 6.0) containing 100 mM sodium chloride (to be referred to as "PB" hereinafter) to a concentration of 20 mg/ml was gently stirred and mixed with 3.1 ml of 50 mM sulfo-SMCC (manufactured by Pierce Chemical Company). After 20 minutes of reaction at 30° C., the resulting reaction mixture was passed through a Sephadex G-25 (manufactured by Pharmacia) colunm (2.5 $\phi \times 14.5$ cm) which has been equilibrated in advance with nitrogen gas-pureged PB, thereby removing unreacted sulfo-SMCC, and then concentrated using CENTRIPREP-10 (manufactured by Amicon) to obtain maleimidated HRPO.

Concentration of the thus obtained maleimidated HRPO was calculated from its absorbance at 403 mm.

$3.3 \times 10^{-7}$ mole of the maleimidated HRPO solution was mixed with a 1/5 molar ratio of the SH group-introduced antibody F815 solution, and the mixture was incubated at 4° C. for 16 hours in an atmosphere of nitrogen gas. After the reaction, 96 µl of 500 mM cysteamine solution in EDTA-PB was added to the reaction mixture, and the reaction was continued at 4° C. for 60 minutes in an atmosphere of nitrogen gas. Thereafter, the resulting reaction mixture was subjected to a gel filtration chromatography using ULTRO-GEL AcA34 (manufactured by IBF Biotechnics) column which has been equilibrated in advance with nitrogen gas-purged PB.

Each of the thus eluted fractions were checked for its absorbances at 280 nm and 403 nm, in order to collect and concentrate fractions containing the F815/HRPO linked product but not containing free enzyme molecules.

The thus concentrated preparation (to be referred to as "HRPO-F815 antibody" hereinafter) was checked for its molecular weight by a Phast system electrophoresis (manufactured by Pharmacia) and its antibody and enzyme contents based on its absorbance and enzyme activity and used as a signal substance generator in measuring experiments.

<2> Preparation of 6-ketoestradiol 6-(O-carboxymethyl) oxime-bovine γ-globulin (to be referred to as "E2-6CMO-γG" hereinafter)

A 6.6 mg portion of E2-6CMO (manufactured by Sigma) was dissolved in 0.66 ml of dioxane, and the solution was mixed with 4.62 µl of tri-n-butylamine (manufactured by Wako Pure Chemical Industries) and 4.62 µl of isobutyl chloroformate (manufactured by Nakalai Tesque) and stirred at 10° C. for 30 minutes. This solution was added to 30.32 ml of a solution of bovine γ-globulin (manufactured by Sigma) which has been adjusted in advance to a concentration of 5 mg/ml with 50% dioxane aqueous solution. Thereafter, the reaction solution was stirred at 10° C. for 4 hours while controlling its pH value at 8.0 to 8.5 with 0.1N sodium hydroxide.

After dialysis against distilled water for 20 hours at 4° C., the reaction solution was mixed with the same volume of diethyl ether and thoroughly shaken and then the ether layer was removed. After repeating this extraction step twice to remove unreacted E2-6CMO in the solution completely, the resulting water layer was dialyzed against PB to obtain E2-6CMO-γG.

<3> Preparation of a first impregnation portion 54 (signal substance generator- and electron mediator-impregnated portion, namely a dried body impregnated with horseradish peroxidase-labeled anti-E2-antibody and N,N,N',N'-tetrakis-(2'-hydroxyethyl)-p-phenylenediamine dihydrochloride (THEPD))

The horseradish peroxidase-labeled anti-E2-antibody (HRPO-F815 antibody) obtained in the above step <1> and THEPD (final concentration, 2 mM) were dissolved in 0.01M phosphate buffer (pH 7.4) containing 5% normal rabbit serum (NRS), 10% lactose and 0.1M NaCl.

Next, a 90 µl portion of the thus prepared solution was spotted on a circular filter paper of 10 mm in diameter obtained by punching the Tween 20-treated glass fiber filter paper prepared in the step <1> of Inventive Example 2, and the resulting filter paper was freeze-dried to obtain the first impregnation portion 54 (signal substance generator- and electron mediator-impregnated portion).

<4> Preparation of a second impregnation portion 56 (buffer solution component-impregnated portion, namely a dried body impregnated with 0.01M phosphate buffer (pH 7.4) containing 0.1M NaCl)

A 90 µl portion of 0.1M NaCl-containing 0.01M phosphate buffer solution (pH 7.4) was spotted on a circular filter paper of 10 mm in diameter obtained by punching the Tween 20-treated glass fiber filter paper prepared in the step <1> of inventive Example 2, and the resulting filter paper was freeze-dried to obtain a dried body impregnated with the buffer solution component.

<5> Preparation of channel 62 (hapten-immobilized membrane)

The E2-6CMO-γG prepared in the above step <2> was dissolved in PBS to a concentration of 2.0 mg/ml. A total of 1,000 circular porous membrane pieces, each having a diameter of 11 mm, were obtained by punching a sheet of a cellulose mixture ester porous membrane (manufactured by Nippon Millipore) having a pore size of 8.0 µm, soaked in 100 ml of the thus prepared solution and shaken at 25° C. for 30 minutes.

Thereafter, the thus treated porous membrane pieces were put on a filter paper to remove moisture and then dried overnight in vacuo to obtain the channel 62 (hapten-immobilized membrane).

<6> Preparation of absorption means 64 (a dried body impregnated with hydrogen peroxide and urea)

A 30 µl portion of a 2.0M hydrogen peroxide-4.0M urea solution prepared in the same manner as described in the step <4> of inventive Example 2 was spotted on a circular filter paper of 10 mm in diameter obtained by punching a chromatograph filter paper (31 ET, manufactured by Whatman), and the resulting filter paper was freeze-dried to obtain a dried body impregnated with hydrogen peroxide and urea.

<7> Construction of specific binding assay device

Using the thus prepared respective parts, various specific binding assay devices shown in FIGS. 2 and 3 were constructed in the following manner.

Firstly, the absorption means 64 (dried body impregnated with hydrogen peroxide and urea) was superposed on the acrylic base cover 66. A seal of 8 mm in diameter obtained by punching a mending tape (manufactured by Sumitomo 3M) was adhered on the center of the absorption means 64. Next, the channel 62 (hapten-immobilized membrane) was superposed on the water absorption filter paper portion having the sealing means 64a, by adjusting their centers at the same position.

On this was superposed the electrode portion 60g in such a manner that the center of the through hole 68 coincided with the center of the channel 62 and the working electrode portion became down side.

Next, the second impregnation portion 56 (buffer solution component-impregnated portion) was superposed in such a manner that its center coincided with the center of the through hole of the electrode. On the center of the upper surface of the second impregnation portion 56 was adhered a seal of 8 mm in diameter obtained by punching a mending tape. On this was superposed the first impregnation portion 54 (signal substance generator- and electron mediator-impregnated portion). On this was further superposed a circular member of 10 mm in diameter prepared by punching surfactant-treated AXTAR (catalog No. B50401, manufactured by Toray Industries) to be used as the filter portion 52.

This was covered with the acrylic upper cover 50 having the sample-introducing hole 50a of 6 mm in diameter in such a manner that the center of the sample-introducing hole 50a coincided with the center of the through hole 68, and then the thus laminated members were fixed by screwing up the four corners of the upper cover 50 and the lower substrate 66. In this way, various types of the specific binding assay device shown in FIGS. 2 and 3 for use in the measurement of the concentration of estradiol were constructed.

<8> Measurement of E2 in heparinized whole blood

The counter electrode 70 of the electrode portion 60g of each of the thus constructed specific binding assay devices was connected as a counter/reference electrode to the counter electrode (reference electrode) terminal of a current measuring circuit, and the respective terminals 76a and 78a of the first working electrode 76 (detection means 1) and the second working electrode 78 (detection means 2) were connected with the channel 1 and channel 2 working electrode terminals of the circuit. The circuit was further connected to a computer via a data gathering board AT-MIO-16X (manufactured by National Instruments) to carry out data processing.

Separately from this, to a heparinized healthy male whole blood sample (A) collected using a Venoject II vacuum blood collection tube (manufactured by Terumo Corp.) was added authentic E2 in an amount of 1 ng/ml, 3 ng/ml, 10 ng/ml, 30 ng/ml or 100 ng/ml to be used in the assay. Other assay samples were also prepared by adding varied amounts of E2 to whole blood samples (B) and (C) collected in the same manner. A 150 µl portion of each of the thus prepared E2-containing heparinized whole blood samples was introduced into the specific binding assay device through the sample-introducing hole of the acrylic upper cover.

Thereafter, electrical potential of each working electrode was set to −150 mV against the counter/reference electrode, and periodical current values were recorded.

<9> Measurement of E2 concentration in each blood sample by enzyme immunoassay

E2 concentration in plasma separated from each whole blood samples were determined using a commercially available E2 measuring kit Enzymun-Test Estradiol (manufactured by Boehringer-Mannheim Corp.). And these E2 concentration were considered as the E2 actual concentrations in the whole blood samples.

Figure 25:
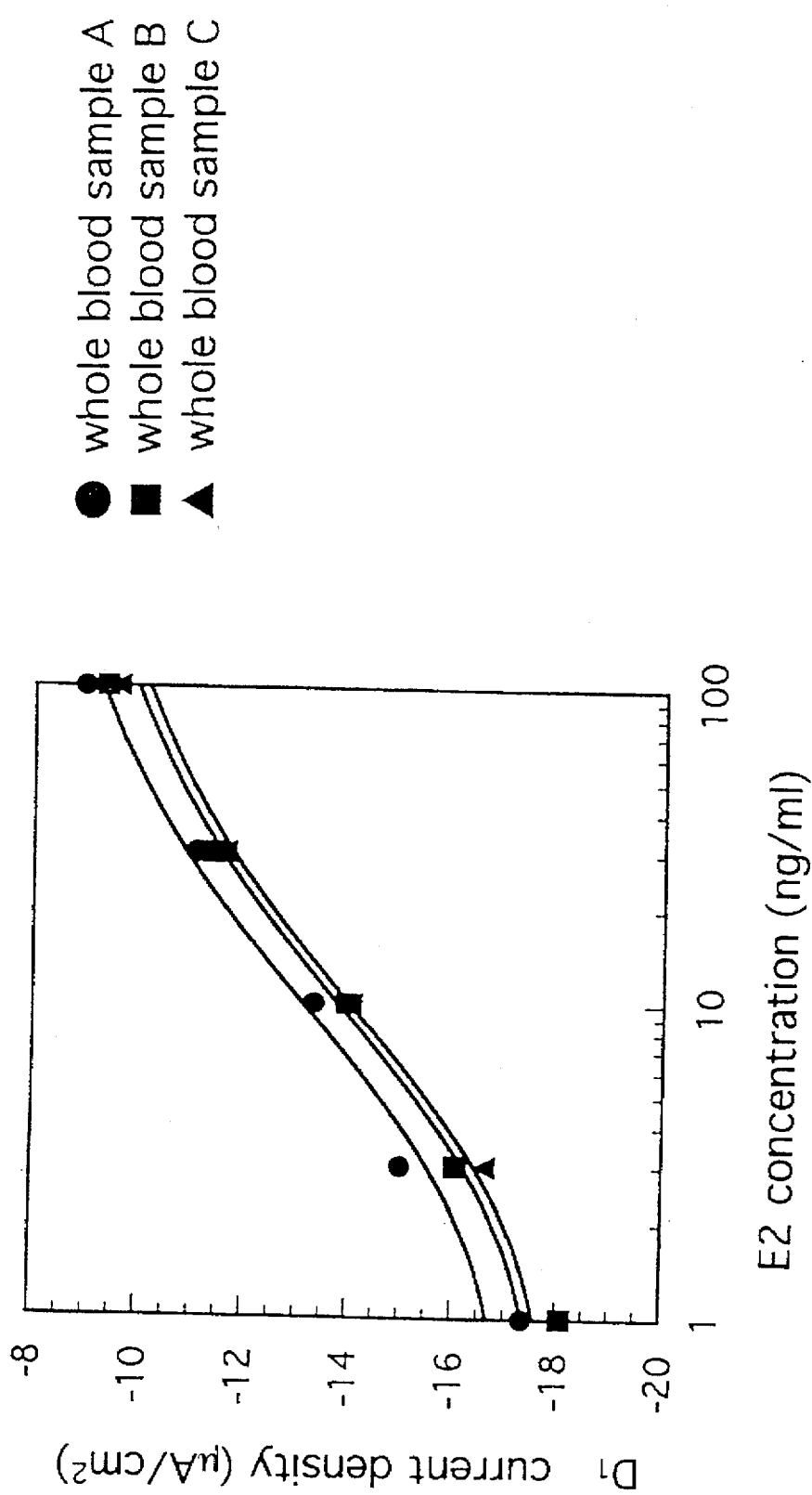
FIG. 25 is a graph showing a relationship between E2 concentrations and current densities ($D_1$).

<10> Result-1 Derivation of a relation expression for use in the enumeration of E2 concentration from plural detection means Average current density values ($D_1$ and $D_2$) were calculated from the average current values $I_1$ and $I_2$ measured for 8 to 10 minutes at the first and second working electrodes 76 and 78 after application of each of the E2 solutions having different concentrations prepared using the heparinized whole blood samples (A), (B) and (C). In this inventive example, one approximate equation for response curve was estimated between the E2 actual concentration and $D_1$ (FIG. 25). Another approximate equation for response curve was estimated between the E2 actual concentration and $D_1+D_2$ instead of $D_2$ only (FIG. 26).

Figure 26:
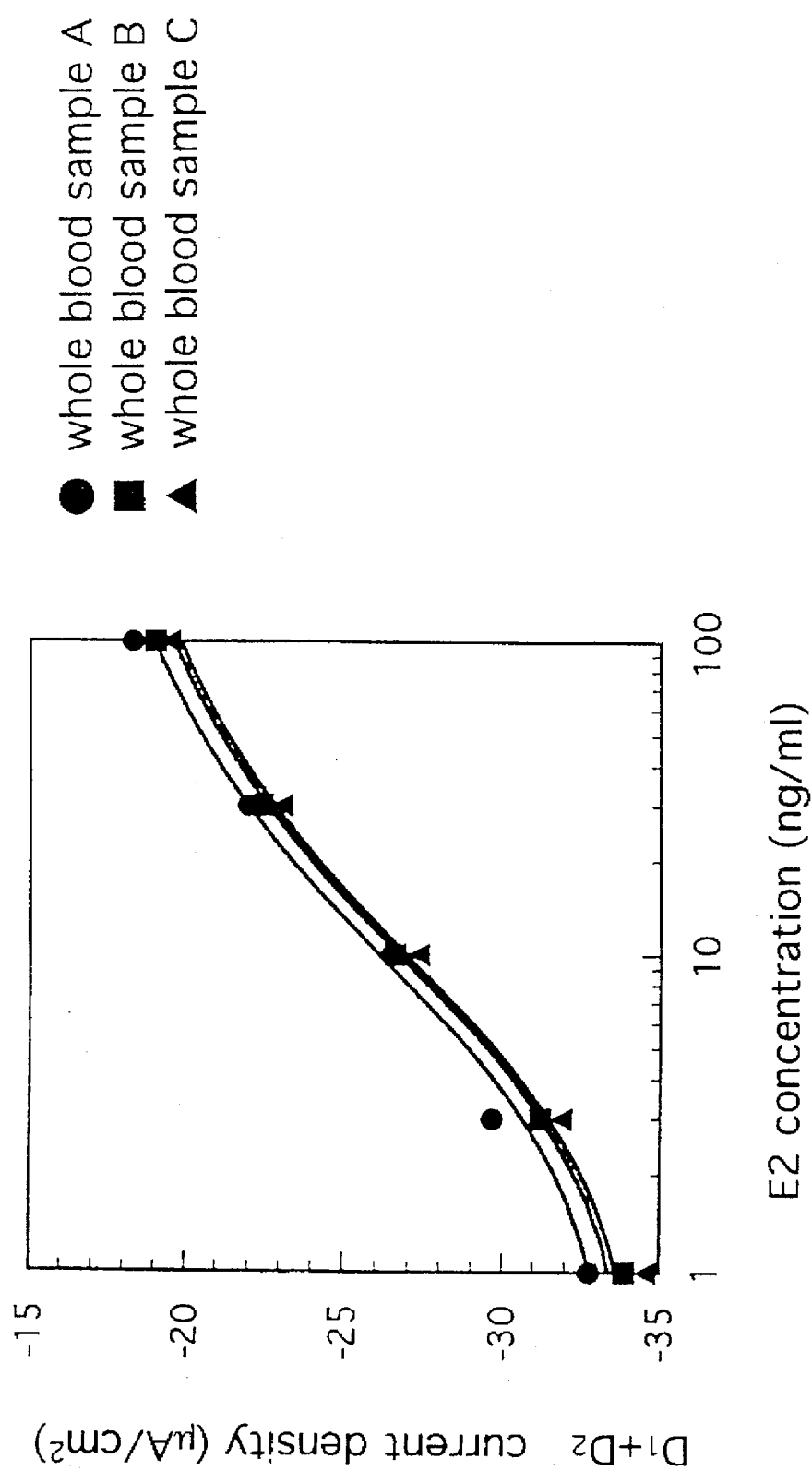
FIG. 26 is a graph showing a relationship between E2 concentrations and current densities ($D_1+D_2$).

As shown in FIGS. 25 and 26, responses of $D_1$ and $D_1+D_2$ to the logarithmic value (log C) of E2 concentration in each whole blood sample fitted to logistic curves of the following formulae 13 and 14. It is noted that the concentration of E2 is expressed in $10^{-1}$ ng/ml unit in formulae 13, 14 and 18.

$$D_1 = \frac{a1 - d1}{1 + (1/c1 \cdot \log C)^{b1}} + d1 \qquad \text{formula 13}$$

$$D_1 + D_2 = \frac{a2 - d2}{1 + (1/c2 \cdot \log C)^{b2}} + d1 \qquad \text{formula 14}$$

Being compared the constants b1, b2, c1 and c2 in the thus calibrated formulae 13 and 14 for three respective whole blood samples (A), (B) and (C), the following approximations were estimated;

$$b1=b2=4.4 \text{ and } c1=c2=2.2$$

Then, the relations of the constants (a1, d1), (a2, d2) and (a1, a2) are summarized in the following formulae 15, 16 and 17.

$$d1=a1+9.7 \qquad \text{formula 15}$$

$$d2=a2+18 \qquad \text{formula 16}$$

$$a2=1.1 \times a1-15 \qquad \text{formula 17}$$

By eliminating sample-dependent coefficients a1, d1, a2 and d2 based on the above formulae (formulae 13, 14, 15, 16 and 17), a relation formula $C=S(D_1, D_1+D_2)$ (formula 18) can be derived.

$$C = 10^{\left( 2.2 \times \mathrm{Exp} \frac{\ln \frac{0.07 D_1 - 1.2 D_2 - 19}{-0.07 D_1 + 1.2 D_2 + 9.3}}{4.4} \right)} \qquad \text{formula 18}$$

<11> Result-2 Derivation of an expression for use in the enumeration of E2 concentration from a single detection means Similar assay was carried out using a single detection means, and the E2 concentration (C) in each sample having different concentrations prepared using the heparinized whole blood samples (A), (B) and (C) described in <10> was calculated when E2 was determined by only $D_1$.

In this case, an expression (formula 19) for use in the enumeration of E2 concentration (C) was obtained from the correlation of $D_1$ to the E2 concentration in whole blood sample (A). It is noted that the concentration of C of E2 is expressed in $10^{-1}$ ng/ml unit in formula 19.

$$C = 10^{\left( 2.2 \times \mathrm{Exp} \frac{\ln \frac{-17 - D_1}{D_1 + 7.3}}{4.4} \right)} \qquad \text{formula 19}$$

The detected current densities of sample (B) and (C) were put in the formula 18 and 19 respectively, and concentrations C of E2 of sample (B) and (C) were calculated, respectively. The calculated C values as well as the average thereof are shown in Table 11.

TABLE 11

| | $E_2$ 3 ng/ml | | $E_2$ 10 ng/ml | | $E_2$ 30 ng/ml | |
|---|---|---|---|---|---|---|
| Sample | Plural detection means (ng/ml) | Single detection means (ng/ml) | Plural detection means (ng/ml) | Single detection means (ng/ml) | Plural detection means (ng/ml) | Single detection means (ng/ml) |
| B | 3 | 2 | 13 | 7 | 32 | 23 |
| C | 3 | 1 | 9 | 7 | 24 | 20 |
| average value | 3 | 2 | 11 | 7 | 28 | 22 |

As is evident from the table 11, determination of E2 making use of the relation formula 18 (the expression on plural detection means) shows clear correction effect compared with the relation formula 19 (the expression on single detection means), thus confirming that the influences of contaminants and the like in a test sample can be offset by this formula. The concentrations C of E2 calculated from the formula 18 and the concentrations of E2 measured by the enzyme immunoassay described in <9> show excellent correlation between them.

[Inventive Example 8]

Determination of relation formula for whole blood assay use, making use of the serum samples.

<1> Construction of specific binding assay device

The following assay was carried out using the same lot of the specific binding assay device constructed in Inventive Example 7.

<2> Measurement of E2 in serum samples for determining the lot-dependent constants To each of a steroid-free serum (manufactured by Scantibodies) sample (serum sample A for determining the lot-dependent constants) (corresponding to the whole blood with low non-specific factor), a steroid-free serum sample containing $5 \times 10^{-10}$M of the aforementioned horseradish peroxidase-labeled anti-E2 antibody and $1 \times 10^{-4}$M of THEPD (serum sample B for determining the lot-dependent constants) (corresponding to the whole blood with high non-specific factor) and a steroid-free serum sample containing $5 \times 10^{-11}$M of the horseradish peroxidase-labeled anti-E2 antibody and $1 \times 10^{-4}$M of THEPD (serum sample C for determining the lot-dependent constants) (corresponding to the whole blood with middle non-specific factor) was added authentic E2 in an amount of 1 ng/ml, 3 ng/ml, 10 ng/ml, 30 ng/ml or 100 ng/ml. A 150 µl portion of each of the thus prepared E2-containing serum samples for testing use was introduced into the aforementioned specific binding assay device through the sample-introducing hole of the acrylic upper cover.

Thereafter, electrical potential of each working electrode was set to −150 mV against the counter/reference electrode, and periodical current values were recorded.

<3> Result-1 Derivation of an expression for use in the enumeration of E2 concentration from serum samples for determining the lot-dependent constants Average current density values ($D_1$ and $D_2$) were calculated from the average current values $I_1$ and $I_2$ measured for 5.5 to 7.5 minutes corresponding to 8 to 10 minutes in whole blood sample at the first and second working electrodes 76 and 78 after application of each of the E2 solutions having different concentrations prepared using the serum samples for determining the lot-dependent constants (A), (B) and (C).

Similar to the case of the whole blood samples described in the foregoing, responses of $D_1$ and $D_1+D_2$ to the logarithmic value (log C) of E2 concentration in each serum sample fitted to the aforementioned logistic curves of formulae 13 and 14. It is noted that when the concentration C of E2 is expressed in $10^{-1}$ ng/ml unit in formula 13, 14 and 23.

Being compared the constants b1, b2, c1 and c2 in the formulae 13 and 14 for three respective serum samples (A), (B) and (C) for determining the lot-dependent constants, the following approximations were estimated;

b1=b2=4.4 and c1=c2=2.2

Then, the relations of the constants (a1, d1), (a2, d2) and (a1, a2) are summarized in the following formulae 20, 21 and 22.

$d1 = a1 + 9.7$     formula 20

$d2 = a2 + 18$     formula 21

$a2 = 1.1 \times a1 - 15$     formula 22

By eliminating sample-dependent coefficients a1, d1, a2 and d2 based on the above formulae (formulae 13, 14, 20, 21 and 22), a relation formula $C = T(D_1, D_1+D_2)$ (formula 23) can be derived.

$$C = 10 \left( 2.2 \times \mathrm{Exp} \frac{\ln \frac{0.07D_1 - 1.2D_2 - 19}{-0.07D_1 + 1.2D_2 + 9.3}}{4.4} \right) \quad \text{formula 23}$$

The relation formula 23 derived from the serum samples for determining the lot-dependent constants coincided with the relation formula 18 derived from the whole blood samples.

Enumeration of E2 concentration in whole blood samples can be accomplished by using the relation formula derived from the serum samples for determining the lot-dependent constants.

Thus, it is apparent that there has been provided, in accordance with the present invention, a specific binding assay method which does not require a step for the separation of unreacted substances (washing step), is excellent in general purpose applicability and can perform highly accurate and quick measurement effected by the exclusion of various factors that decrease reliability of the measured values, such factors including influence of contaminants, non-specific influence of test samples upon the measurement, assay conditions such as reaction temperature and the like and changes in the activity of reagents used in the assay caused for example by their inactivation, as well as a specific binding assay device suitable for the practice of the specific binding assay method.

What is claimed is:

1. A method of determining the amount of a substance in a liquid sample comprising flowing a signal substance generator and a liquid sample through a predetermined channel in a predetermined direction, such that a specific binding reaction takes place with at least said substance and said signal substance generator thereby causing the formation of a specific distribution of the signal substance generator in said channel which is dependent on the concentration of said substance, said specific distribution formed by an affinity chromatographic, a molecular sieve chromatographic, or an immunoprecipitation process;

generating a signal substance from said signal substance generator specifically distributed in said channel;

allowing dispersion of unreacted signal substance generator throughout the channel;

allowing diffusion of said signal substance to a plurality of detection means arranged in different positions in said flow direction;

detecting said signal substance with said plurality of detection means; and determining the concentration of said substance from the relative signal detected at the detection means.

2. A specific binding assay device useful in practicing the specific binding assay method of claim 1, which comprises (1) a liquid sample-introducing means, (2) a liquid sample-flowing channel connected thereto, wherein said channel is capable of forming a specific distribution of signal substance generator through said specific binding reaction, a change of a particle size or a molecular weight being accompanied with said specific binding reaction, or a formation of a precipitation complex being accompanied with said specific binding reaction, and (3) a plurality of detection means arranged at different positions in the liquid flow direction of said channel for use in the detection of a distribution of a signal substance generator, formed in said channel by a specific binding reaction of a substance to be assayed with a specific binding substance capable of binding specifically thereto, as a signal strength which is rate-limited by diffusion mass transfer of a signal substance generated from said signal substance generator.

3. The specific binding assay device according to claim 2 wherein said plurality of detection means are spaced apart from each other by a distance of 10 µm or more in the flow direction.

4. The specific binding assay method according to claim 1 wherein said plural detection means are electrochemical electrodes.

5. A method of determining the amount of a substance in liquid sample according to claim 1, wherein the plurality of detection means comprises two or more working electrodes and a counter (reference) electrode.

6. A method of determining the amount of a substance in a liquid sample according to claim 1 wherein, the plurality of detection means are arranged in different positions in said flow direction at a distance in said flow direction of at least 10 µm.

7. A method of determining the amount of a substance in a liquid sample according to claim 1 wherein, the determination of the concentration of said substance from the relative signal detected at the detection means is processed in an arithmetic processing unit by a preliminarily determined arithmetic processing method.

8. A method of determining the amount of a substance in a liquid sample according to claim 1 wherein the following non-specific factors in the measurement can be minimized,
   (a) contaminants in and properties of test samples including sample-derived activities analogous to a signal substance generator,
   (b) sample properties
   (c) assay environments
   (d) changing degrees of reagent component activities, caused by inactivation:
      changes in the activity of a signal substance generator,
      changes in the activity of a substance related to the generation of a signal substance and
      changes in the activity of a substance related to the generation of a signal.

9. A method of determining the amount of a substance in a liquid sample according to claim 1 wherein said arithmetic processing method is capable of minimizing additive influences and proportional influences in the measurement.

* * * * *

UNITED STATES PATENT AND TRADEMARK OFFICE
CERTIFICATE OF CORRECTION

PATENT NO.   : 5,723,345
DATED        : March 3, 1998
INVENTOR(S)  : Tadakazu YAMAUCHI and Hideyuki TERASAWA It is certified that error appears in the above-identified patent and that said Letters Patent is hereby corrected as shown below:

On the title page:
Item 75, delete "Saitama" and insert --Tokyo--.

Signed and Sealed this

Twenty-fourth Day of November, 1998

Attest:

BRUCE LEHMAN

Attesting Officer

Commissioner of Patents and Trademarks